(12) United States Patent
Wang

(10) Patent No.: US 9,102,752 B2
(45) Date of Patent: Aug. 11, 2015

(54) PEPTIDE VACCINE FOR PREVENTION AND IMMUNOTHERAPY OF DEMENTIA OF THE ALZHEIMER'S TYPE

(71) Applicant: United Biomedical, Inc., Hauppauge, NY (US)

(72) Inventor: Chang Yi Wang, Cold Spring Harbor, NY (US)

(73) Assignee: UNITED BIOMEDICAL, INC., Hauppauge, NY (US)

( * ) Notice: Subject to any disclaimer, the term of this patent is extended or adjusted under 35 U.S.C. 154(b) by 0 days.

(21) Appl. No.: 13/843,883

(22) Filed: Mar. 15, 2013

(65) Prior Publication Data
US 2014/0271690 A1 Sep. 18, 2014

(51) Int. Cl.
| | |
|---|---|
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *A61K 38/00* | (2006.01) |
| *A61K 49/00* | (2006.01) |
| *C07K 14/47* | (2006.01) |

(52) U.S. Cl.
CPC .................. *C07K 14/4711* (2013.01)

(58) Field of Classification Search
CPC .................. G01N 33/6896; G01N 2333/4709; G01N 2800/2821; A61K 2039/55555; A61K 39/0005; A61K 2039/55561; A61K 38/00; A61K 9/1271; C07K 14/47; C07K 14/4711
See application file for complete search history.

(56) References Cited

U.S. PATENT DOCUMENTS

| | | | |
|---|---|---|---|
| 5,750,349 A | 5/1998 | Suzuki et al. | |
| 5,753,624 A | 5/1998 | McMichael et al. | |
| 5,759,551 A | 6/1998 | Ladd et al. | |
| 5,843,446 A | 12/1998 | Ladd et al. | |
| 5,955,317 A | 9/1999 | Suzuki et al. | |
| 6,025,468 A | 2/2000 | Wang | |
| 6,228,987 B1 | 5/2001 | Wang | |
| 6,713,301 B1 | 3/2004 | Wang | |
| 6,750,324 B1 | 6/2004 | Schenk et al. | |
| 6,787,138 B1 | 9/2004 | Schenk | |
| 6,906,169 B2 | 6/2005 | Wang | |
| 7,951,909 B2 | 5/2011 | Wang | |
| 8,034,348 B2 | 10/2011 | Schenk et al. | |
| 8,084,015 B2 | 12/2011 | Sokoll | |
| 8,232,373 B2 | 7/2012 | Wang | |
| 2003/0165481 A1 | 9/2003 | Hersh | |
| 2004/0009897 A1 | 1/2004 | Sokoll | |
| 2004/0247612 A1 | 12/2004 | Wang | |
| 2006/0088548 A1 | 4/2006 | Chain | |
| 2011/0171243 A1 | 7/2011 | Mandler et al. | |

FOREIGN PATENT DOCUMENTS

| | | |
|---|---|---|
| EP | 0 526 511 B1 | 5/1997 |
| WO | 94/28412 A1 | 12/1994 |
| WO | 95/11998 A1 | 5/1995 |
| WO | 99/27944 A1 | 6/1999 |
| WO | 99/66952 A1 | 12/1999 |
| WO | 99/66957 A2 | 12/1999 |
| WO | 00/72880 A2 | 12/2000 |
| WO | 01/18169 A2 | 3/2001 |
| WO | 01/42306 A2 | 6/2001 |

OTHER PUBLICATIONS

Li et al. Neurosci. Lett. 2011, 505: 128-133.*
Subramanian et al. Neurosci. Lett 2008, 436: 219-222.*
Partidos, et al., "Immune Responses in Mice Following Immunization with Chimeric Synthetic Peptides Representing B and T Cell Epitopes of Measles Virus Proteins", J. Gen. Virol., 72:1293 (1991).
International Search Report as issued in International Application No. PCT/US02/10293, dated Sep. 30, 2004.
International Preliminary Examination Report as issued in International Application No. PCT/US02/10293, dated Apr. 18, 2005.
International Search Report as issued in related International Application No. PCT/US13/037865, dated Nov. 1, 2013.
Written Opinion of the International Searching Authority as issued in related International Application No. PCT/US13/037865, dated Nov. 1, 2013.
Peet, et al. "The effect of low-profile serine substitutions in the V3-loop of HIV-1 gp120 IIIB/LAI on the immunogenicity of the envelope protein." Virology, 251:59-70 (1998).
Rockenstein, et al. "Levels and alternative splicing of amyloid beta protein precursor (APP) transcripts in brains of APP transgenic mice and humans with Alzheimer's disease." Journal of Biological Chemistry. 270(47):28257-28267 (1995).
Rockenstein, et al. "Early formation of mature amyloid-beta protein deposits in a mutant APP transgenic model depends on levels of A-beta(1-42)." Journal of Neuroscience Research, 66(4):573-582 (2001).
Schenk, et al., "Immunization with Amyloid-β Attenuates Alzheimer-disease-like Pathology in the PDAPP mouse", Nature, 400:173-177 (1999).
Schenk, et al., "β-Peptide Immunization—A Possible New Treatment for Alzheimer Disease", Archives of Neurology, 57:934-936 (2000).
Selkoe, "Amyloid β-Protein and the Genetics of Alzheimer's Disease", J. Biol. Chem., 271:18295-18298 (1996).
Seubert, "Isolation and Quantification of Soluble Alzheimer's β-peptide from Biological Fluids", Nature, 359:325-327 (1992).

(Continued)

*Primary Examiner* — Chang-Yu Wang
(74) *Attorney, Agent, or Firm* — Locke Lord, LLP

(57) ABSTRACT

The present disclosure is directed to individual Aβ peptide immunogen constructs, peptide compositions comprising these Aβ peptide immunogen constructs and mixtures thereof, pharmaceutical compositions including vaccine formulations comprising these Aβ peptide immunogen constructs, with the individual Aβ peptide immunogen constructs having the N-terminus of the Aβ peptide as the B cell (B) epitopes linked through spacer residue(s) to heterologous T helper cell (Th) epitopes derived from pathogen proteins that act together to stimulate the generation of highly specific antibodies directed against the N-terminus of the Aβ peptide offering protective immune responses to patients at risk for, or with, Alzheimer's Disease.

20 Claims, 26 Drawing Sheets

(56) References Cited

OTHER PUBLICATIONS

Skolnick, et al. "From genes to protein structure and function: novel applications of computational approaches in the genomic era." Trends in Biotech, 18:34-39 (2000).
Soloman, et al., "Monoclonal Antibodies Inhibit In Vitro Fibrillar Aggregation of the Alzheimer β-amyloid Peptide", Proc. Natl. Acad. Sci. USA, 93:452-455 (1996).
Soloman, et al., "Disaggregation of Alzheimer β-amyloid by Site-Directed mAb", Proc. Natl. Acad. Sci. USA, 94:4109-4112 (1997).
Solomon, et al. The Amino Terminus Of Beta-Amyloid Peptide Contains An Essential Epitope For Maintaining Its Solubility. Progress in Alzheimer's and Parkinson's Diseases. Ed. by Fisher et al., Plenum Press, (New York, NY), pp. 205-211 (1998).
Stagg, et al., "Primary Human T-cell Responses to the Major Outer Membrane Protein of *Chlamydia trachomatis*", Immunology, 79:1-9 (1993).
Stodel, et al. "Transmembrane structures for Alzheimer's Aβ1-42 Oligomers", J. Am. Chem. Soc. 132:13300-13312 (2010).
Su, et al. "Intravascular infusions of soluble beta-amyloid compromise the blood-brain barrier, activate CNS glial cells and induce peripheral hemorrhage." Brain Res, 818:105-117. (1999).
Tabira, "Immunization therapy for Alzheimer disease: a comprehensive review of active immunization strategies." Tohoku Journal of Experimental Medicine, 220(2):95-106 (2010).
Terry, et al., "The Neuropathology of Alzheimer Disease and the Structural Basis of its Cognitive Alterations", In Alzheimer Disease, 187-206 (1999).
Thomas, et al., "β-Amyloid-mediated Vasoactivity and Vascular Endothelial Damage", Nature, 380:168-171 (1996).
Traggiai, et al. "An efficient method to make human monoclonal antibodies from memory B cells." Nature Medicine 10(8): 871-875 (2004).
Vickers JC. "A vaccine against Alzheimer's disease." Drugs Aging., 19(7):487-494 (2002).
Wang, et al., "Long-Term High-Titer Neutralizing Activity Induced by Octameric Synthetic HIV-1 Antigen", Science, 254:285-288 (1991).
Wang, et al. "Long-term high-titer neutralizing activity induced by octameric synthetic HIV-1 antigen." Science, 254 (5029):285-288 (1991).
Wang, et al. "Site-specific peptide vaccines for immunotherapy and immunization against chronic diseases, cancer, infectious diseases, and for veterinary applications." Vaccine, 23(17-19):2049-2056 (2005).
Wikipedia Contributors, "Beta amyloid," Wikipedia, The Free Encyclopedia, http://en.wikipedia.org/w/index.php?title=Beta_amyloid&oldid=537444164, accessed Apr. 28, 2014, (revision date Feb. 9, 2013).
Wong, et al. "Neuritic plaques and cerebrovascular amyloid in Alzheimer disease are antigenically related", Proc. Natl. Acad. Sci. USA, 82:8729-8732 (1985).
Yankner, et al., "Neurotrophic and Neurotoxic Effects of Amyloid β Protein: Reversal by Tachykinin Neuropeptides", Science, 250:279-282 (1990).
Young E. "Alzheimer's vaccine trial suspended," New Scientist, 14:50 (2002).
Anderton, "Progress in molecular pathology", Nature, 325:658-659 (1987).
Araujo, et al. "β-Amyloid stimulates glial cells in vitro to produce growth factors that accumulate in senile plaques in Alzheimer's disease", Brain Res., 569:141-145 (1992).
Arispe, et al., "Alzheimer disease amyloid β protein forms calcium channels in bilayer membranes: Blockade by tromethamine and aluminum", Proc. Natl. Acad. Sci. USA, 90:567-571 (1993).
Babbitt, et al., "Binding of immunogenic peptides to Ia histocompatibility molecules", Nature, 317:359 (1985).
Bard, et al., "Peripherally administered antibodies against amyloid β-peptide enter the central nervous system and reduce pathology in a mouse model of Alzheimer disease", Nature Medicine, 6:916-919 (2000).

Barnes, "Defect in Alzheimer's Is on Chromosome 21", Science, 235:846-847 (1987).
Behl, et al., "Hydrogen Peroxide Mediates Amyloid β Protein Toxicity", Cell, 77:817-827 (1994).
Behrouz, et al. "Antiserum To The N-Terminal Subsequence Of The Alzheimer Amyloid Beta Protein Does Not React With Neurofibrillary Tangles." Journal Gerontology. vol. 44, No. 6, pp. B156-B159 (1998).
Busciglio, et al., "β-Amyloid Fibrils Induce Tau Phosphorylation and Loss of Microtubule Binding", Neuron, 14:879-888 (1995).
Cease, et al., "Helper T-cell antigenic site identification in the acquired immunodeficiency syndrome virus gp120 envelope protein and induction of immunity in mice to the native protein using a 16-residue synthetic peptide", Proc. Natl. Acad. Sci. USA, 84:4249-4253 (1987).
Chapman, "Model behaviour—Trials in mice of a possible vaccine for Alzheimer's disease show that it reduces the behavioural defects and the brain damage seen in the desease. As promising as these results are, a human vaccine remains a long way off", Nature, 408:915-916 (1992).
Citron, et al, "Mutation of the β-amyloid precursor protein in familial Alzheimer's disease increases β-protein production", Nature, 360:672-674 (1992).
Eldridge et al., "Biodegradable Microspheres as a vaccine delivery system", Molec. Immunol., 28-287-294 (1991).
European Search Report as issued in related European Application No. 02731223, dated Jun. 27, 2005.
Supplemental European Search Report as issued in related European Application No. 02731223, dated Oct. 4, 2005.
European Search Report as issued in related European Application No. 09168110.6, dated Oct. 6, 2009.
Ferrari, et al, J. "Identification of Immunodominant T Cell Epitopes of the Hepatitis B Virus Nucleocapsid Antigen", Clin. Invest., 88:214-222 (1991).
Fields, et al., "Principles and Practice of Solid-Phase Peptide Synthesis", in: Synthetic Peptides: A Users Guide. Grant GA, ed. New York: WH Freeman and Company: Chapter 3, pp. 77-183 (1992).
Frenkel, et al., "Immunization against Alzheimer's β-amyloid plaques via EFRH phage administration", Proc. Natl. Acad. Sci. USA, 97:11455-11459 (2000).
Frenkel, et al., "Generation of auto-antibodies towards Alzheimer's disease vaccination", Vaccine, 19:2615-2619 (2001).
Gaskin, et al., "Autoantibodies to Neurofibrillary Tangles and Brain Tissue in Alzheimer's Disease", JEM, 165:245 (1987).
Glenner, et al., "Alzheimer's Disease: Initial Report of the Purification and Characterization of a Novel Cerebrovascular Amyloid Protein", Biochem Biophys Res Comm, 120-885-890 (1984).
Glenner, et al., "Alzheimer's Disease and Down's Syndrome: Sharing of a Unique Cerebrovascular Amyloid Fibril Protein", Biochem Biophys Res Comm, 122:1131-1135 (1984).
Goate, et al., "Segregation of a missense mutation in the amyloid precursor protein gene with familial Alzheimer's disease", Nature, 349:704-706 (1991).
Green, et al., "Effect of tarenflurbil on cognitive decline and activities of daily living in patients with mild Alzheimer Disease: A randomized controlled trial", JAMA, 302(23):2557-2564 (2009).
Grubeck-Loebenstein, et al., "Immunization with beta-amyloid: could T-cell activation have a harmful effect?", Trends in Neuroscience, 23:114 (2000).
Hanan, E., et al. "Inhibitory Effect Of Monoclonal Antibodies On Alzheimer's Beta-Amylod Peptide Aggregation." Int. J. Exp. Clin. Invest. vol. 3, pp. 130-133 (1996).
Hardy, J. "Amyloid, the presenilins and Alzheimer's disease", Trends Neurosci. 20:154-159 (1997).
Hartman, et al. "Distinct sites of intracellular production for Alzheimer's disease Aβ40/42 amyloid peptides", 3 (9):1016-1020 (1997).
Janus, et al., "Aβ Peptide Immunization Reduces Behavioural Impairment and Plaques In A Model of Alzheimer's Disease", Nature, 408:979-982 (2000).
Jobling, et al. Analysis Of Structure And Function Of The B Subunit Of Cholera Toxin By The Use Of Site-Directed Mutagenesis. Mol. Microbiol., 5(7):1755-1767 (1991).

(56) References Cited

OTHER PUBLICATIONS

Johnson-Wood, et al., "Amyloid Precursor Protein Processing and Aβ42 Deposition in a Transgenic Mouse Model of Alzheimer Disease", Proc. Natl. Acad. Sci. USA, 94:1550-1555 (1997).

Kang, et al., "The precursor of Alzheimer's Disease Amyloid A4 protein Resembles a Cell-Surface Receptor", Nature, 1987; 325:733-737 (1987).

Katial, et al. "Cytokine production in cell culture by peripheral blood mononuclear cells from immunocompetent hosts", Clin. Diagn. Lab. Immunol. 5 (1):78-81 (1998).

King, et al. "Structure-immunogenicity relationship of melittin and its N-terminal truncated analogs." Biochemistry, 32:3506-3510 (1993).

Klein, et al., "Targeting Small Aβ Oligomers: The Solution to an Alzheimer's Disease Conundrum?", Trends in Neurosciences, 24:219-224 (2001).

Kumar, et al. "Relative sensitivity of undifferentiated and cyclic adenosine 3', 5'-monophosphate-induced differentiated neuroblastoma cells to cyclosporin A: Potential role of β-amyloid and ubiquitin in neurotoxicity" In Vitro Cellular & Developmental Biology—Animal. vol. 36, No. 2, pp. 81-87 (2000).

Lacor, PN. "Advances on the understanding of the origins of synaptic pathology in Alzheimer's disease." Current Genomics, 8(8):486-508 (2007).

Lemere, et al., "Nasal Aβ Treatment Induces Anti-Aβ Antibody Production and Decreases Cerebral Amyloid Burden in PD-APP Mice", Annals of the New York Academy of Sciences, 920:328-332 (2000).

de Lustig ES, et al. "Peripheral markers and diagnostic criteria in Alzheimer's disease: Critical evaluations." Rev in Neurosciences, 5:213-224 (1994).

Majocha, et al. "Development Of A Monoclonal Antibody Specific For Beta/A4 Amyloid In Alzheimer's Disease Brain For Application In In Vivo Imaging Of Amyloid Angiopathy", J. Nuc. Med. vol. 33, No. 12, pp. 2184-2189 (1992).

Masters, et al., "Amyloid Plaque Core Protein in Alzheimer Disease and Down Syndrome", Proc. Natl. Acad. Sci. USA, 82:4245-4249 (1985).

Meister, et al., "Two Novel T Cell Epitope Prediction Algorithms Based on MHC-Binding Motifs; Comparison of Predicted and Published Epitopes from *Mycrobacterium tuberculosis* and HIV Protein Sequences", Vaccine, 13:581-591 (1995).

Moore, et al. "Peptide design considerations", in: Synthetic Peptides: A Users Guide. Grant GA, ed. New York: WH Freeman and Company: Chapter 2, pp. 63-67 (1992).

Morgan, et al., "Aβ Peptide Vaccination Prevents Memory Loss in an Animal Model of Alzheimer's Disease", Nature, 408:982-985 (2000).

Morgan, D. "Immunotherapy for Alzheimer's Disease." Journal of Internal Medicine 269(1):54-63 (2011).

Mullan, et al., "A Pathogenic Mutation for Probable Alzheimer's Disease in the APP Gene at the N-Terminus of β-amyloid", Nature Genetics, 1:345-347 (1992).

Munch, et al. "Potential neurotoxic inflammatory responses to Abeta vaccination in humans." J. Neural Transm., 109:1081-1087 (2002).

O'Hagan, et al., "Controlled Release Microparticles for Vaccine Development", Vaccine, 9:768-771 (1991).

Orgogozo, et al. "Subacute meningoencephalitis in a subset of patients with AD after Aβ42 immunization." Neurology, 61:45-54 (2003).

\* cited by examiner

```
                        SEQUENCE LISTING

<160> NUMBER OF SEQ ID NOS: 67

<210> SEQ ID NO 1
<211> LENGTH: 42
<212> TYPE: PRT
<213> ORGANISM: Homo sapiens
```

```
<220> FEATURE:
<221> NAME/KEY: PEPTIDE
<222> LOCATION: (1)..(42)
<223> OTHER INFORMATION: Abeta 1-42 or APP 770(D672-A713)

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: Abeta 1-40 or APP770(D672-V711)

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 28
<212> TYPE: PRT
<213> ORGANISM: Homo sapiens
<220> FEATURE:
<221> NAME/KEY: PEPTIDE
<222> LOCATION: (1)..(28)
<223> OTHER INFORMATION: Abeta 1-28 or AP770(D672-K699)

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14 or APP770(D672-H685)

<400> SEQUENCE: 4

Asp Ala Glu Phe Arg His Asp Ser Gly Tyr Glu Val His His
1               5                   10

<210> SEQ ID NO 5
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Abeta 1-12 or APP 770(D672-V683)
```

```
<400> SEQUENCE: 5

Asp Ala Glu Phe Arg His Asp Ser Gly Tyr Glu Val
1               5                   10

<210> SEQ ID NO 6
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 1-10 or APP 770(D672-Y681)

<400> SEQUENCE: 6

Asp Ala Glu Phe Arg His Asp Ser Gly Tyr
1               5                   10

<210> SEQ ID NO 7
<211> LENGTH: 28
<212> TYPE: PRT
<213> ORGANISM: Homo sapiens
<220> FEATURE:
<221> NAME/KEY: PEPTIDE
<222> LOCATION: (1)..(28)
<223> OTHER INFORMATION: Abeta 15-42 or APP 770(Q686-A711)

<400> SEQUENCE: 7

Gln Lys Leu Val Phe Phe Ala Glu Asp Val Gly Ser Asn Lys Gly Ala
1               5                   10                  15

Ile Ile Gly Leu Met Val Gly Gly Val Val Ile Ala
            20                  25

<210> SEQ ID NO 8
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -9-1 or APP 770(T663-D672)

<400> SEQUENCE: 8

Thr Glu Glu Ile Ser Glu Val Lys Met Asp
1               5                   10

<210> SEQ ID NO 9
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -8-2 or APP 770(E664-A673)

<400> SEQUENCE: 9

Glu Glu Ile Ser Glu Val Lys Met Asp Ala
1               5                   10

<210> SEQ ID NO 10
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -7-3 or APP 770(E665-E674)
```

```
<400> SEQUENCE: 10

Glu Ile Ser Glu Val Lys Met Asp Ala Glu
1               5                   10

<210> SEQ ID NO 11
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -6-4 or APP 770(I666-F675)

<400> SEQUENCE: 11

Ile Ser Glu Val Lys Met Asp Ala Glu Phe
1               5                   10

<210> SEQ ID NO 12
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -5-5 or APP 770(S667-R676)

<400> SEQUENCE: 12

Ser Glu Val Lys Met Asp Ala Glu Phe Arg
1               5                   10

<210> SEQ ID NO 13
<211> LENGTH: 10
<212> TYPE: PRT
<213> ORGANISM: Homo sapiens
<220> FEATURE:
<221> NAME/KEY: PROPEP
<222> LOCATION: (1)..(10)
<223> OTHER INFORMATION: Abeta -4-6 or APP 770(E668-H677)

<400> SEQUENCE: 13

Glu Val Lys Met Asp Ala Glu Phe Arg His
1               5                   10

<210> SEQ ID NO 14
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -3-7 or APP 770(V669-D678)

<400> SEQUENCE: 14

Val Lys Met Asp Ala Glu Phe Arg His Asp
1               5                   10

<210> SEQ ID NO 15
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -2-8 or APP 770(K670-S679)

<400> SEQUENCE: 15

Lys Met Asp Ala Glu Phe Arg His Asp Ser
1               5                   10
```

```
<210> SEQ ID NO 16
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta -1-9 or APP 770(M671-G680)

<400> SEQUENCE: 16

Met Asp Ala Glu Phe Arg His Asp Ser Gly
1               5                   10

<210> SEQ ID NO 17
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 2-11 or APP 770(A673-E682)

<400> SEQUENCE: 17

Ala Glu Phe Arg His Asp Ser Gly Tyr Glu
1               5                   10

<210> SEQ ID NO 18
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 3-12 or APP 770(E674-V683)

<400> SEQUENCE: 18

Glu Phe Arg His Asp Ser Gly Tyr Glu Val
1               5                   10

<210> SEQ ID NO 19
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 4-13 or  APP 770(F675-H684)

<400> SEQUENCE: 19

Phe Arg His Asp Ser Gly Tyr Glu Val His
1               5                   10

<210> SEQ ID NO 20
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 5-14 or APP 770(R676-H685)

<400> SEQUENCE: 20

Arg His Asp Ser Gly Tyr Glu Val His His
1               5                   10

<210> SEQ ID NO 21
<211> LENGTH: 10
```

```
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 6-15 or APP 770(H677-Q686)

<400> SEQUENCE: 21

His Asp Ser Gly Tyr Glu Val His His Gln
1               5                   10

<210> SEQ ID NO 22
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 7-16 or APP 770(D678-K687)

<400> SEQUENCE: 22

Asp Ser Gly Tyr Glu Val His His Gln Lys
1               5                   10

<210> SEQ ID NO 23
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 8-17 or APP 770(S679-L688)

<400> SEQUENCE: 23

Ser Gly Tyr Glu Val His His Gln Lys Leu
1               5                   10

<210> SEQ ID NO 24
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 9-18 or APP 770(G680-V689)

<400> SEQUENCE: 24

Gly Tyr Glu Val His His Gln Lys Leu Val
1               5                   10

<210> SEQ ID NO 25
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 10-19 or APP 770(Y681-F690)

<400> SEQUENCE: 25

Tyr Glu Val His His Gln Lys Leu Val Phe
1               5                   10

<210> SEQ ID NO 26
<211> LENGTH: 10
<212> TYPE: PRT
<213> ORGANISM: Homo sapiens
<220> FEATURE:
<221> NAME/KEY: PEPTIDE
```

```
<222> LOCATION: (1)..(10)
<223> OTHER INFORMATION: Abeta 11-20 or APP 770(E682-F691)

<400> SEQUENCE: 26

Glu Val His His Gln Lys Leu Val Phe Phe
1               5                   10

<210> SEQ ID NO 27
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 12-21 or APP 770(V683-A692)

<400> SEQUENCE: 27

Val His His Gln Lys Leu Val Phe Phe Ala
1               5                   10

<210> SEQ ID NO 28
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 13-22 or APP 770(H684-E693)

<400> SEQUENCE: 28

His His Gln Lys Leu Val Phe Phe Ala Glu
1               5                   10

<210> SEQ ID NO 29
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 14-23 or APP 770(H685-D694)

<400> SEQUENCE: 29

His Gln Lys Leu Val Phe Phe Ala Glu Asp
1               5                   10

<210> SEQ ID NO 30
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 15-24 or APP 770(Q686-V695)

<400> SEQUENCE: 30

Gln Lys Leu Val Phe Phe Ala Glu Asp Val
1               5                   10

<210> SEQ ID NO 31
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<223> OTHER INFORMATION: Abeta 16-22 or APP 770(K687-E693)

<400> SEQUENCE: 31
```

```
Lys Leu Val Phe Phe Ala Glu
1               5

<210> SEQ ID NO 32
<211> LENGTH: 4
<212> TYPE: PRT
<213> ORGANISM: Homo sapiens
<220> FEATURE:
<221> NAME/KEY: PEPTIDE
<222> LOCATION: (1)..(1)
<223> OTHER INFORMATION: epsilon K
<220> FEATURE:
<221> NAME/KEY: PEPTIDE
<222> LOCATION: (1)..(4)
<223> OTHER INFORMATION: spacer A

<400> SEQUENCE: 32

Lys Lys Lys Lys
1

<210> SEQ ID NO 33
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 1 Th

<400> SEQUENCE: 33

Lys Lys Gln Tyr Ile Lys Ala Asn Ser Lys Phe Ile Gly Ile Thr Glu
1               5                   10                  15

Leu

<210> SEQ ID NO 34
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF1 Th

<400> SEQUENCE: 34

Leu Ser Glu Ile Lys Gly Val Ile Val His Arg Leu Glu Gly Val
1               5                   10                  15

<210> SEQ ID NO 35
<211> LENGTH: 24
<212> TYPE: PRT
<213> ORGANISM: Bordetella pertussis
<220> FEATURE:
<221> NAME/KEY: PEPTIDE
<222> LOCATION: (1)..(24)
<223> OTHER INFORMATION: Bordetella pertussis Th

<400> SEQUENCE: 35

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 36
<211> LENGTH: 17
<212> TYPE: PRT
<213> ORGANISM: Clostridium tetani
<220> FEATURE:
```

```
<221> NAME/KEY: PEPTIDE
<222> LOCATION: (1)..(17)
<223> OTHER INFORMATION: Clostridium tetani 2 Th

<400> SEQUENCE: 36

Trp Val Arg Asp Ile Ile Asp Asp Phe Thr Asn Glu Ser Ser Gln Lys
1               5                   10                  15

Thr

<210> SEQ ID NO 37
<211> LENGTH: 23
<212> TYPE: PRT
<213> ORGANISM: diphtheria bacilli
<220> FEATURE:
<221> NAME/KEY: PEPTIDE
<222> LOCATION: (1)..(23)
<223> OTHER INFORMATION: Diphtheria Th

<400> SEQUENCE: 37

Asp Ser Glu Thr Ala Asp Asn Leu Glu Lys Thr Val Ala Ala Leu Ser
1               5                   10                  15

Ile Leu Pro Gly His Gly Cys
            20

<210> SEQ ID NO 38
<211> LENGTH: 21
<212> TYPE: PRT
<213> ORGANISM: Plasmodium falciparum
<220> FEATURE:
<221> NAME/KEY: PEPTIDE
<222> LOCATION: (1)..(21)
<223> OTHER INFORMATION: Plasmodium falciparum Th

<400> SEQUENCE: 38

Asp His Glu Lys Lys His Ala Lys Met Glu Lys Ala Ser Ser Val Phe
1               5                   10                  15

Asn Val Val Asn Ser
            20

<210> SEQ ID NO 39
<211> LENGTH: 17
<212> TYPE: PRT
<213> ORGANISM: Schistosoma mansoni
<220> FEATURE:
<221> NAME/KEY: PEPTIDE
<222> LOCATION: (1)..(17)
<223> OTHER INFORMATION: Schistosoma mansoni Th

<400> SEQUENCE: 39

Lys Trp Phe Lys Thr Asn Ala Pro Asn Gly Val Asp Glu Lys His Arg
1               5                   10                  15

His

<210> SEQ ID NO 40
<211> LENGTH: 25
<212> TYPE: PRT
<213> ORGANISM: Cholera Toxin
<220> FEATURE:
<221> NAME/KEY: PEPTIDE
<222> LOCATION: (1)..(25)
<223> OTHER INFORMATION: Cholera Toxin Th

<400> SEQUENCE: 40

Ala Leu Asn Ile Trp Asp Arg Phe Asp Val Phe Cys Thr Leu Gly Ala
1               5                   10                  15
```

```
Thr Thr Gly Tyr Leu Lys Gly Asn Ser
            20                  25

<210> SEQ ID NO 41
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF 2 Th

<400> SEQUENCE: 41

Ile Ser Glu Ile Lys Gly Val Ile Val His Lys Ile Glu Gly Ile
1               5                   10                  15

<210> SEQ ID NO 42
<211> LENGTH: 22
<212> TYPE: PRT
<213> ORGANISM: Measles virus
<220> FEATURE:
<221> NAME/KEY: PEPTIDE
<222> LOCATION: (1)..(22)
<223> OTHER INFORMATION: KKKMvF 3 Th
<220> FEATURE:
<221> NAME/KEY: MISC_FEATURE
<222> LOCATION: (7)..(7)
<223> OTHER INFORMATION: S or T
<220> FEATURE:
<221> NAME/KEY: MISC_FEATURE
<222> LOCATION: (10)..(10)
<223> OTHER INFORMATION: K or R
<220> FEATURE:
<221> NAME/KEY: MISC_FEATURE
<222> LOCATION: (11)..(11)
<223> OTHER INFORMATION: G or T
<220> FEATURE:
<221> NAME/KEY: MISC_FEATURE
<222> LOCATION: (15)..(15)
<223> OTHER INFORMATION: H or T
<220> FEATURE:
<221> NAME/KEY: MISC_FEATURE
<222> LOCATION: (16)..(16)
<223> OTHER INFORMATION: K or R
<220> FEATURE:
<221> NAME/KEY: MISC_FEATURE
<222> LOCATION: (19)..(19)
<223> OTHER INFORMATION: G or T

<400> SEQUENCE: 42

Lys Lys Lys Ile Ser Ile Xaa Glu Ile Xaa Xaa Val Ile Val Xaa Xaa
1               5                   10                  15

Ile Glu Xaa Ile Leu Phe
            20

<210> SEQ ID NO 43
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 1 Th
<220> FEATURE:
<221> NAME/KEY: MISC_FEATURE
<222> LOCATION: (1)..(1)
<223> OTHER INFORMATION: K or R
<220> FEATURE:
<221> NAME/KEY: MISC_FEATURE
<222> LOCATION: (2)..(2)
<223> OTHER INFORMATION: K or R
<220> FEATURE:
<221> NAME/KEY: MISC_FEATURE
```

```
<222> LOCATION: (3)..(3)
<223> OTHER INFORMATION: K or R
<220> FEATURE:
<221> NAME/KEY: MISC_FEATURE
<222> LOCATION: (4)..(4)
<223> OTHER INFORMATION: L or I or V or F
<220> FEATURE:
<221> NAME/KEY: MISC_FEATURE
<222> LOCATION: (5)..(5)
<223> OTHER INFORMATION: F or K or R
<220> FEATURE:
<221> NAME/KEY: MISC_FEATURE
<222> LOCATION: (6)..(6)
<223> OTHER INFORMATION: L or I or V or F
<220> FEATURE:
<221> NAME/KEY: MISC_FEATURE
<222> LOCATION: (7)..(7)
<223> OTHER INFORMATION: L or I or V or F
<220> FEATURE:
<221> NAME/KEY: MISC_FEATURE
<222> LOCATION: (9)..(9)
<223> OTHER INFORMATION: K or R
<220> FEATURE:
<221> NAME/KEY: MISC_FEATURE
<222> LOCATION: (10)..(10)
<223> OTHER INFORMATION: L or I or V or F
<220> FEATURE:
<221> NAME/KEY: MISC_FEATURE
<222> LOCATION: (11)..(11)
<223> OTHER INFORMATION: L or I or V or F
<220> FEATURE:
<221> NAME/KEY: MISC_FEATURE
<222> LOCATION: (13)..(13)
<223> OTHER INFORMATION: L or I or V or F
<220> FEATURE:
<221> NAME/KEY: MISC_FEATURE
<222> LOCATION: (15)..(15)
<223> OTHER INFORMATION: Q or L or I or V or F
<220> FEATURE:
<221> NAME/KEY: MISC_FEATURE
<222> LOCATION: (17)..(17)
<223> OTHER INFORMATION: L or I or V or F
<220> FEATURE:
<221> NAME/KEY: MISC_FEATURE
<222> LOCATION: (18)..(18)
<223> OTHER INFORMATION: D or R

<400> SEQUENCE: 43

Xaa Xaa Xaa Xaa Xaa Xaa Xaa Thr Xaa Xaa Xaa Thr Xaa Pro Xaa Ser
1               5                   10                  15

Xaa Xaa

<210> SEQ ID NO 44
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 4 Th
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
```

```
<220> FEATURE:
<221> NAME/KEY: MISC_FEATURE
<222> LOCATION: (13)..(13)
<223> OTHER INFORMATION: K or R

<400> SEQUENCE: 44

Ile Ser Ile Xaa Glu Ile Xaa Xaa Val Ile Val Xaa Xaa Ile Glu Thr
1               5                   10                  15

Ile Leu Phe

<210> SEQ ID NO 45
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 2 Th
<220> FEATURE:
<221> NAME/KEY: MISC_FEATURE
<222> LOCATION: (4)..(4)
<223> OTHER INFORMATION: I or F
<220> FEATURE:
<221> NAME/KEY: MISC_FEATURE
<222> LOCATION: (5)..(5)
<223> OTHER INFORMATION: I or F
<220> FEATURE:
<221> NAME/KEY: MISC_FEATURE
<222> LOCATION: (6)..(6)
<223> OTHER INFORMATION: T or L
<220> FEATURE:
<221> NAME/KEY: MISC_FEATURE
<222> LOCATION: (7)..(7)
<223> OTHER INFORMATION: I or L
<220> FEATURE:
<221> NAME/KEY: MISC_FEATURE
<222> LOCATION: (11)..(11)
<223> OTHER INFORMATION: I or L
<220> FEATURE:
<221> NAME/KEY: MISC_FEATURE
<222> LOCATION: (14)..(14)
<223> OTHER INFORMATION: P or I
<220> FEATURE:
<221> NAME/KEY: MISC_FEATURE
<222> LOCATION: (15)..(15)
<223> OTHER INFORMATION: Q or T
<220> FEATURE:
<221> NAME/KEY: MISC_FEATURE
<222> LOCATION: (16)..(16)
<223> OTHER INFORMATION: S or T
<220> FEATURE:
<221> NAME/KEY: MISC_FEATURE
<222> LOCATION: (17)..(17)
<223> OTHER INFORMATION: L or I

<400> SEQUENCE: 45

Lys Lys Lys Xaa Xaa Xaa Xaa Thr Arg Ile Xaa Thr Ile Xaa Xaa Xaa
1               5                   10                  15

Xaa Asp

<210> SEQ ID NO 46
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 5 Th

<400> SEQUENCE: 46

Ile Ser Ile Thr Glu Ile Lys Gly Val Ile Val His Arg Ile Glu Thr
1               5                   10                  15
```

Ile Leu Phe

<210> SEQ ID NO 47
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 3 Th

<400> SEQUENCE: 47

Lys Lys Lys Ile Ile Thr Ile Thr Arg Ile Ile Thr Ile Ile Thr Thr
1               5                   10                  15

Ile Asp

<210> SEQ ID NO 48
<211> LENGTH: 32
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(32)
<223> OTHER INFORMATION: Clostridium tetani 1 Th

<400> SEQUENCE: 48

Asp Ala Glu Phe Arg His Asp Ser Gly Tyr Glu Val His His Lys Lys
1               5                   10                  15

Lys Gln Tyr Ile Lys Ala Asn Ser Lys Phe Ile Gly Ile Thr Glu Leu
                20                  25                  30

<210> SEQ ID NO 49
<211> LENGTH: 26
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: Abeta 1-10
<220> FEATURE:
<221> NAME/KEY: PEPTIDE
<222> LOCATION: (11)..(11)
<223> OTHER INFORMATION: epsilon K as a spacer
<220> FEATURE:
<221> NAME/KEY: PEPTIDE
<222> LOCATION: (12)..(26)
<223> OTHER INFORMATION: MvF 1 Th

<400> SEQUENCE: 49

Asp Ala Glu Phe Arg His Asp Ser Gly Tyr Lys Leu Ser Glu Ile Lys
1               5                   10                  15

Gly Val Ile Val His Arg Leu Glu Gly Val
                20                  25

<210> SEQ ID NO 50
<211> LENGTH: 28
<212> TYPE: PRT
<213> ORGANISM: Homo sapiens
<220> FEATURE:
<221> NAME/KEY: PEPTIDE

```
<222> LOCATION: (1)..(12)
<223> OTHER INFORMATION: Abeta 1-12
<220> FEATURE:
<221> NAME/KEY: PEPTIDE
<222> LOCATION: (13)..(13)
<223> OTHER INFORMATION: epsilon K as a spacer
<220> FEATURE:
<221> NAME/KEY: PEPTIDE
<222> LOCATION: (14)..(28)
<223> OTHER INFORMATION: MvF 1 Th

<400> SEQUENCE: 50

Asp Ala Glu Phe Arg His Asp Ser Gly Tyr Glu Val Lys Leu Ser Glu
1               5                   10                  15

Ile Lys Gly Val Ile Val His Arg Leu Glu Gly Val
            20                  25

<210> SEQ ID NO 51
<211> LENGTH: 30
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(30)
<223> OTHER INFORMATION: MvF 1 Th

<400> SEQUENCE: 51

Asp Ala Glu Phe Arg His Asp Ser Gly Tyr Glu Val His His Lys Leu
1               5                   10                  15

Ser Glu Ile Lys Gly Val Ile Val His Arg Leu Glu Gly Val
            20                  25                  30

<210> SEQ ID NO 52
<211> LENGTH: 39
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(39)
<223> OTHER INFORMATION: Bordetella pertussis Th

<400> SEQUENCE: 52

Asp Ala Glu Phe Arg His Asp Ser Gly Tyr Glu Val His His Lys Gly
1               5                   10                  15

Ala Tyr Ala Arg Cys Pro Asn Gly Thr Arg Ala Leu Thr Val Ala Glu
            20                  25                  30

Leu Arg Gly Asn Ala Glu Leu
        35

<210> SEQ ID NO 53
<211> LENGTH: 32
<212> TYPE: PRT
<213> ORGANISM: Homo sapiens
```

```
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spcer
<220> FEATURE:
<221> NAME/KEY: PEPTIDE
<222> LOCATION: (16)..(32)
<223> OTHER INFORMATION: Clostridium tetani 2 Th

<400> SEQUENCE: 53

Asp Ala Glu Phe Arg His Asp Ser Gly Tyr Glu Val His His Lys Trp
1               5                   10                  15

Val Arg Asp Ile Ile Asp Asp Phe Thr Asn Glu Ser Ser Gln Lys Thr
            20                  25                  30

<210

```
<210> SEQ ID NO 56
<211> LENGTH: 32
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(32)
<223> OTHER INFORMATION: Schistosoma mansoni Th

<400> SEQUENCE: 56

Asp Ala Glu Phe Arg His Asp Ser Gly Tyr Glu Val His His Lys Lys
1               5                   10                  15

Trp Phe Lys Thr Asn Ala Pro Asn Gly Val Asp Glu Lys His Arg His
            20                  25                  30

<210> SEQ ID NO 57
<211> LENGTH: 40
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(40)
<223> OTHER INFORMATION: Cholera Toxin Th

<400> SEQUENCE: 57

Asp Ala Glu Phe Arg His Asp Ser Gly Tyr Glu Val His His Lys Ala
1               5                   10                  15

Leu Asn Ile Trp Asp Arg Phe Asp Val Phe Cys Thr Leu Gly Ala Thr
            20                  25                  30

Thr Gly Tyr Leu Lys Gly Asn Ser
        35                  40

<210> SEQ ID NO 58
<211> LENGTH: 30
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(30)
<223> OTHER INFORMATION: MvF 2 Th

<400> SEQUENCE: 58

Asp Ala Glu Phe Arg His Asp Ser Gly Tyr Glu Val His His Lys Ile
1               5                   10                  15

Ser Glu Ile Lys Gly Val Ile Val His Lys Ile Glu Gly Ile
```

```
                    20                  25                  30

<210> SEQ ID NO 59
<211> LENGTH: 37
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: PEPTIDE
<222> LOCATION: (16)..(37)
<223> OTHER INFORMATION: KKKMvF 3 Th
<220> FEATURE:
<221> NAME/KEY: MISC_FEATURE
<222> LOCATION: (22)..(22)
<223> OTHER INFORMATION: S or T
<220> FEATURE:
<221> NAME/KEY: MISC_FEATURE
<222> LOCATION: (25)..(25)
<223> OTHER INFORMATION: K or R
<220> FEATURE:
<221> NAME/KEY: MISC_FEATURE
<222> LOCATION: (26)..(26)
<223> OTHER INFORMATION: G or T
<220> FEATURE:
<221> NAME/KEY: MISC_FEATURE
<222> LOCATION: (30)..(30)
<223> OTHER INFORMATION: H or T
<220> FEATURE:
<221> NAME/KEY: MISC_FEATURE
<222> LOCATION: (31)..(31)
<223> OTHER INFORMATION: K or R
<220> FEATURE:
<221> NAME/KEY: MISC_FEATURE
<222> LOCATION: (34)..(34)
<223> OTHER INFORMATION: G or T

<400> SEQUENCE: 59

Asp Ala Glu Phe Arg His Asp Ser Gly Tyr Glu Val His His Lys Lys
1               5                   10                  15

Lys Lys Ile Ser Ile Xaa Glu Ile Xaa Xaa Val Ile Val Xaa Xaa Ile
                20                  25                  30

Glu Xaa Ile Leu Phe
        35

<210> SEQ ID NO 60
<211> LENGTH: 33
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a spacer
<220> FEATURE:
<221> NAME/KEY: MISC_FEATURE
<222> LOCATION: (16)..(16)
<223> OTHER INFORMATION: K or R
<220> FEATURE:
<221> NAME/KEY: MISC_FEATURE
<222> LOCATION: (17)..(17)
<223> OTHER INFORMATION: K or R
<220> FEATURE:
<221> NAME/KEY: MISC_FEATURE
<222> LOCATION: (18)..(18)
```

```
<223> OTHER INFORMATION: K or R
<220> FEATURE:
<221> NAME/KEY: MISC_FEATURE
<222> LOCATION: (19)..(19)
<223> OTHER INFORMATION: L or I or V or F
<220> FEATURE:
<221> NAME/KEY: MISC_FEATURE
<222> LOCATION: (20)..(20)
<223> OTHER INFORMATION: F or K or R
<220> FEATURE:
<221> NAME/KEY: MISC_FEATURE
<222> LOCATION: (21)..(21)
<223> OTHER INFORMATION: L or I or V or F
<220> FEATURE:
<221> NAME/KEY: MISC_FEATURE
<222> LOCATION: (22)..(22)
<223> OTHER INFORMATION: L or I or V or F
<220> FEATURE:
<221> NAME/KEY: MISC_FEATURE
<222> LOCATION: (24)..(24)
<223> OTHER INFORMATION: K or R
<220> FEATURE:
<221> NAME/KEY: MISC_FEATURE
<222> LOCATION: (25)..(25)
<223> OTHER INFORMATION: L or I or V or F
<220> FEATURE:
<221> NAME/KEY: MISC_FEATURE
<222> LOCATION: (26)..(26)
<223> OTHER INFORMATION: L or I or V or F
<220> FEATURE:
<221> NAME/KEY: MISC_FEATURE
<222> LOCATION: (28)..(28)
<223> OTHER INFORMATION: L or I or V or F
<220> FEATURE:
<221> NAME/KEY: MISC_FEATURE
<222> LOCATION: (30)..(30)
<223> OTHER INFORMATION: Q or L or I or V or F
<220> FEATURE:
<221> NAME/KEY: MISC_FEATURE
<222> LOCATION: (32)..(32)
<223> OTHER INFORMATION: L or I or V or F
<220> FEATURE:
<221> NAME/KEY: MISC_FEATURE
<222> LOCATION: (33)..(33)
<223> OTHER INFORMATION: D or R

<400> SEQUENCE: 60

Asp Ala Glu Phe Arg His Asp Ser Gly Tyr Glu Val His His Lys Xaa
1               5                   10                  15

Xaa Xaa Xaa Xaa Xaa Xaa Thr Xaa Xaa Xaa Thr Xaa Pro Xaa Ser Xaa
            20                  25                  30

Xaa

<210> SEQ ID NO 61
<211> LENGTH: 31
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: (Abeta 1-14) x 4 as branched peptide
<220> FEATURE:
<221> NAME/KEY: PEPTIDE
<222> LOCATION: (15)..(15)
<223> OTHER INFORMATION: (epsilon K) x 2 as a linker
<220> FEATURE:
<221> NAME/KEY: PEPTIDE
<222> LOCATION: (16)..(16)
<223> OTHER INFORMATION: epsilon K as linked spacer
<220> FEATURE:
<221> NAME/KEY: PEPTIDE
<222> LOCATION: (17)..(31)
<223> OTHER INFORMATION: MvF 1 Th

<400> SEQUENCE: 61
```

```
Asp Ala Glu Phe Arg His Asp Ser Gly Tyr Glu Val His His Lys Lys
1               5                   10                  15

Leu Ser Glu Ile Lys Gly Val Ile Val His Arg Leu Glu Gly Val
            20                  25                  30
```

<210> SEQ ID NO 62
<211> LENGTH: 37
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a linked spacer
<220> FEATURE:
<221> NAME/KEY: PEPTIDE
<222> LOCATION: (16)..(37)
<223> OTHER INFORMATION: KKK- MvF 4 Th
<220> FEATURE:
<221> NAME/KEY: MISC_FEATURE
<222> LOCATION: (22)..(22)
<223> OTHER INFORMATION: S or T
<220> FEATURE:
<221> NAME/KEY: MISC_FEATURE
<222> LOCATION: (25)..(25)
<223> OTHER INFORMATION: K or R
<220> FEATURE:
<221> NAME/KEY: MISC_FEATURE
<222> LOCATION: (26)..(26)
<223> OTHER INFORMATION: G or T
<220> FEATURE:
<221> NAME/KEY: MISC_FEATURE
<222> LOCATION: (30)..(30)
<223> OTHER INFORMATION: H or T
<220> FEATURE:
<221> NAME/KEY: MISC_FEATURE
<222> LOCATION: (31)..(31)
<223> OTHER INFORMATION: K or R

<400> SEQUENCE: 62

```
Asp Ala Glu Phe Arg His Asp Ser Gly Tyr Glu Val His His Lys Lys
1               5                   10                  15

Lys Lys Ile Ser Ile Xaa Glu Ile Xaa Xaa Val Ile Val Xaa Xaa Ile
            20                  25                  30

Glu Thr Ile Leu Phe
        35
```

<210> SEQ ID NO 63
<211> LENGTH: 33
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a linked spacer
<220> FEATURE:
<221> NAME/KEY: PEPTIDE
<222> LOCATION: (16)..(33)
<223> OTHER INFORMATION: HBsAg 2 Th
<220> FEATURE:
<221> NAME/KEY: MISC_FEATURE
<222> LOCATION: (19)..(19)
<223> OTHER INFORMATION: I or F
<220> FEATURE:
<221> NAME/KEY: MISC_FEATURE

```
<222> LOCATION: (20)..(20)
<223> OTHER INFORMATION: I or F
<220> FEATURE:
<221> NAME/KEY: MISC_FEATURE
<222> LOCATION: (21)..(21)
<223> OTHER INFORMATION: T or L
<220> FEATURE:
<221> NAME/KEY: MISC_FEATURE
<222> LOCATION: (22)..(22)
<223> OTHER INFORMATION: I or L
<220> FEATURE:
<221> NAME/KEY: MISC_FEATURE
<222> LOCATION: (26)..(26)
<223> OTHER INFORMATION: I or L
<220> FEATURE:
<221> NAME/KEY: MISC_FEATURE
<222> LOCATION: (29)..(29)
<223> OTHER INFORMATION: P or I
<220> FEATURE:
<221> NAME/KEY: MISC_FEATURE
<222> LOCATION: (30)..(30)
<223> OTHER INFORMATION: Q or T
<220> FEATURE:
<221> NAME/KEY: MISC_FEATURE
<222> LOCATION: (31)..(31)
<223> OTHER INFORMATION: S or T
<220> FEATURE:
<221> NAME/KEY: MISC_FEATURE
<222> LOCATION: (32)..(32)
<223> OTHER INFORMATION: L or I

<400> SEQUENCE: 63

Asp Ala Glu Phe Arg His Asp Ser Gly Tyr Glu Val His His Lys Lys
1               5                   10                  15

Lys Lys Ile Ile Thr Ile Thr Arg Ile Ile Thr Ile Pro Gln Ser Leu
            20                  25                  30

Asp

<210> SEQ ID NO 64
<211> LENGTH: 37
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
<220> FEATURE:
<221> NAME/KEY: PEPTIDE
<222> LOCATION: (15)..(15)
<223> OTHER INFORMATION: epsilon K as a linked spacer
<220> FEATURE:
<221> NAME/KEY: PEPTIDE
<222> LOCATION: (16)..(37)
<223> OTHER INFORMATION: KKK-MvF 5 Th

<400> SEQUENCE: 64

Asp Ala Glu Phe Arg His Asp Ser Gly Tyr Glu Val His His Lys Lys
1               5                   10                  15

Lys Lys Ile Ser Ile Thr Glu Ile Lys Gly Val Ile Val His Arg Ile
            20                  25                  30

Glu Thr Ile Leu Phe
        35

<210> SEQ ID NO 65
<211> LENGTH: 33
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Abeta 1-14
```

```
<220> FEATURE:
<221> NAME/KEY: PEPTIDE
<222> LOCATION: (15)..(15)
<223> OTHER INFORMATION: epsilon K as a linked spacer
<220> FEATURE:
<221> NAME/KEY: PEPTIDE
<222> LOCATION: (16)..(33)
<223> OTHER INFORMATION: HBsAg 3 Th

<400> SEQUENCE: 65

Asp Ala Glu Phe Arg His Asp Ser Gly Tyr Glu Val His His Lys Lys
1               5                   10                  15

Lys Lys Ile Ile Thr Ile Thr Arg Ile Ile Thr Ile Ile Thr Thr Ile
            20                  25                  30

Asp

<210> SEQ ID NO 66
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Abeta 1-16 or APP 770(D672-K687)

<400> SEQUENCE: 66

Asp Ala Glu Phe Arg His Asp Ser Gly Tyr Glu Val His His Gln Lys
1               5                   10                  15

<210> SEQ ID NO 67
<211> LENGTH: 26
<212> TYPE: PRT
<213> ORGANISM: Homo sapiens
<220> FEATURE:
<221> NAME/KEY: PEPTIDE
<222> LOCATION: (1)..(26)
<223> OTHER INFORMATION: Abeta 17-42 or APP 770(L688-A713)

<400> SEQUENCE: 67

Leu Val Phe Phe Ala Glu Asp Val Gly Ser Asn Lys Gly Ala Ile Ile
1               5                   10                  15

Gly Leu Met Val Gly Gly Val Val Ile Ala
            20                  25
```

PEPTIDE VACCINE FOR PREVENTION AND IMMUNOTHERAPY OF DEMENTIA OF THE ALZHEIMER'S TYPE

FIELD OF THE INVENTION

This disclosure relates to a peptide-based vaccine and formulations thereof for prevention and immunotherapy of dementia of the Alzheimer's type.

BACKGROUND OF THE INVENTION

Alzheimer's Disease (AD) is the most common form of dementia, a chronic, neurodegenerative disorder characterized by a loss of cognitive ability, severe behavior abnormalities, and death. It affects roughly 10% of the population over age 65 and 40% of those over age 85. Unlike other leading causes of death such as heart disease, cancer and stroke, mortality from Alzheimer's disease will escalate dramatically over the next two to three decades as advances in medical technology permit more individuals to reach the age of risk for dementias. In the United States, 7-8% of all medical costs are related to dementia today. There are currently 2.5 to 4.0 million patients living with AD in the U.S. and 17 to 25 million worldwide. There is no definitive treatment or cure for this devastating disease.

As originally defined by Alois Alzheimer (1907), two microscopic deposits, i.e., the neurofibrillary tangle and the senile amyloid plaque, remain the pathologic hallmarks of the disease. The definitive diagnosis of Alzheimer's disease has traditionally required either biopsy or postmortem histopathology. With the recent introduction of ligands labeling amyloid plaques with positron emitting isotopes, combined with cognitive testing and measurements of specific molecules in the spinal fluid, more definitive diagnosis of this disease has now become available without histopathology.

Considerable evidence has been accumulated suggesting that the β-amyloid (Aβ) peptide-the major component of senile amyloid plaques—plays an important role in AD. An updated review on the β-amyloid (Aβ) peptide (as of Feb. 13, 2013) is available from Wikipedia at en.wikipedia.org/wiki/Beta_amyloid#cite_note-wales2010-41 which link is included here by reference. Successful disease-modifying therapy for AD is likely to include products that affect the deposition of β-amyloid in the brain. A recent publication by Morgan, D. on "Immunotherapy for Alzheimer's Disease" (Morgan D. *J Int Med* 2011; 269:54-63), which is relevant to this invention is included by reference as a review of the field.

The initiating factor, necessary but not sufficient for Alzheimer's disease, is the accumulation of amyloid aggregates consisting of the Aβ peptide. The genetics of familial forms of Alzheimer's disease and Down's syndrome cases (which result in precocious Alzheimer pathology) have overproduction of a longer C-terminal form of the Aβ peptide (42 amino acids in length) as a common element. This $A\beta_{1-42}$ peptide is prone to form beta sheet structures and aggregate into oligomers and fibrils. These amyloid deposits may be present a decade or longer in the brain prior to the initiation of the cognitive symptoms of the disorder. A second step in the pathogenesis of the disease is the formation of intraneuronal neurofibrillary tangles from hyperphosphorylated microtubule binding protein tau. Other neurodegenerative disorders can also be formed by the tau pathology in the absence of amyloid deposits, but they differ from Alzheimer's both in clinical presentation and in the location of the pathology regionally in the brain. In tau transgenic mouse models, the tau deposits can be precipitated by intracranial injection of amyloid or breeding with mice producing Aβ deposits. Moreover, interrupting the amyloid deposition with anti-Aβ immunotherapy can diminish the progression of tau pathology in mice expressing multiple transgenes. The tau pathology appears to be better correlated with cognitive status than the amyloid pathology, consistent with it being the more proximal cause of the mental dysfunction. By uncertain mechanisms, these pathologies result in the loss of synaptic function, synapses, and ultimately a loss of neurons leading to considerable brain atrophy.

There are multiple hypotheses regarding the mechanistic steps involved. The intermediate sized aggregates of amyloid and/or tau, referred to as oligomers, are considered a more direct cause of toxicity. Even in the earliest stages of the disorder, the "mild cognitive impairment" (MCI) phase, there appears to be considerable accumulation of plaque and tangle pathology, and neuron loss. These observations suggest that treating the disorder at the earliest possible stages, much as is done with cardiovascular disease, will be essential to controlling Alzheimer's disease.

In 1999, a vaccine approach was found to reduce amyloid deposits in transgenic mice overproducing the amyloid precursor protein. Thereafter, vaccines or passive immunotherapy targeting Aβ were found to rescue memory deficits in these mice. Aβ-specific antibodies, actively generated by the immune system or passively administered, consistently reduce plaque burden in different transgenic mouse models for Aβ-amyloidosis. Given the success of vaccination in animal models, and the lack of any alternative disease modifying therapy for Alzheimer's disease, a first clinical attempt to stimulate the immune system of AD patients to generate Aβ-antibody was initiated with a vaccine termed AN1792, which consisted of full length $A\beta_{1-42}$ peptide containing both B and T cell epitopes, aggregated into fibrils. About 60 patients were treated with one or more doses of the vaccine in a phase 1 safety trial. One of the initial observations was a variable antibody response, with many patient vaccines failing to generate detectable antibody titers against the target Aβ peptide antigen. This lack of immune response in many of the patients led to a change of vaccine formulation to include QS-21 as the adjuvant in an attempt to enhance the immunogenicity of the AN1792 vaccine formulation in the phase 2 safety and immunogenicity trial. The goal was to immunize patients to a preset antibody titer through multiple inoculations. However, the immunizations were halted within a short time of initiating the trial due to a small percentage of the patients (~6%) developing aseptic meningoencephalopathy, an inflammatory reaction in the Central Nervous System (CNS). Two patients who developed these symptoms of CNS inflammation died with subsequent autopsies revealing a T cell infiltration of the CNS, apparent with signs of meningeal inflammation. It was concluded that the adverse response of the AN1792 vaccine formulation was an autoimmune reaction caused by the vaccine (Orgogozo J M, et al., *Neurology* 2003; 61:46-54). From an efficacy viewpoint, no differences in the rate of brain shrinkage by MRI or cognitive performance were observed between the vaccines and those receiving placebo vaccine.

Despite the AN1792 vaccine set back, the development of novel vaccine strategies and adjuvants against the Aβ peptide for immunotherapy of Alzheimer's disease has been an area of intense creativity. In most instances, the goal has been to develop B cell activation and antibody production, with minimal T cell involvement (at least against Aβ), due to the adverse events found in human trials with vaccines against the full length $A\beta_{1-42}$ peptide as shown in the AN1792 case.

Currently, aside from the product of this invention managed by the inventor and her team, there are four Phase I/II clinical trials of active immunization employing various vaccine designs and formulations targeting Aβ fragments. These trials include: ACC-001 (Elan Corporation Inc. and Wyeth) using as immunogen the Aβ$_{1-7}$ amino-terminal peptide fragment conjugated to a diphtheria toxoid protein; CAD106 (Immunodrug™; Cytos Biotechnology AG and Novartis Pharma AG) using as immunogen the Aβ$_{1-5}$ amino-terminal peptide fragment coupled to Qβ virus-like particle; V950 (Merck) using as immunogen Aβ amino-terminal peptides conjugated to ISCO-MATRIX; and GSK/Affiris using as immunogen Aβ peptide mimetics conjugated to carrier molecules. In addition, there are other vaccine approaches targeting Aβ as described in a review by Tabira T (Tohoku *J Exp Med* 2010; 220:95-106).

All vaccine designs and formulations targeting Aβ currently in human trials, as described above, suffer from weak immunogenicity with variable antibody response in that only from 30% to approximately 70% to 80% of patients receiving these vaccines developed antibodies towards the target Aβ peptide, which makes any further analysis of efficacy resulting from the vaccine generated anti-Aβ antibodies more complicated. Most of the vaccine designs are complicated, requiring conjugation of the very short Aβ peptide fragments to a large protein or viral particle like carrier, thus directing most of the antibody responses towards the undesired carrier rather than the short target peptides; complicated vaccine designs dictate extensive manufacturing procedures, thus difficult in quality control and not cost-effective. These vaccines are uncertain in their safety characteristics due to the potential Th1 activation property of the adjuvant and formulation used. In addition, as of this date, none of these vaccines has shown any clinical efficacy such as improvement in cognition functions in patients receiving the vaccines.

In developed countries, AD is one of the most costly diseases to society. New therapies must be found to prevent, delay the onset, or slow the progression of AD. Despite the promising findings of immunological interventions in mice for AD, a safe and efficacious human vaccine targeting Aβ for prevention and treatment of dementia of Alzheimer's type remains a challenge. In view of the limitations of vaccine designs and formulations currently in preclinical or clinical trials as discussed above, there is an unmet and urgent need for the development of a safe and efficacious vaccine formulation to provide broadly responsive immunotherapy for prevention and treatment of dementia of the Alzheimer's type. When such a vaccine formulation is successful against Alzheimer's pathology, it will become among the standard approaches to preventing the disease.

SUMMARY OF THE INVENTION

The present disclosure is directed to individual Aβ peptide immunogen constructs, peptide compositions comprising these Aβ peptide immunogen constructs and mixtures thereof, pharmaceutical compositions including vaccine formulations comprising these Aβ peptide immunogen constructs, with the individual Aβ peptide immunogen constructs having the N-terminus of the Aβ peptide as the B cell (B) epitopes linked through spacer residue(s) to heterologous T helper cell (Th) epitopes derived from pathogen proteins that act together to stimulate the generation of highly specific antibodies directed against the N-terminus of the Aβ peptide offering protective immune responses to patients at risk for, or with, Alzheimer's Disease.

In an embodiment, Aβ peptide immunogen constructs can comprise hybrid Aβ peptide having a B cell antigenic site between 10 to 14 amino acids in length from the amino terminus of the Aβ$_{1-42}$ peptide, e.g. Aβ$_{1-10}$, Aβ$_{1-12}$, Aβ$_{1-14}$, that is linked to a heterologous Th epitope derived from pathogenic proteins such as Measles Virus Fusion (MVF) protein (SEQ ID NO: 34) that act together to stimulate the generation of highly specific antibodies cross-reactive the full length Aβ$_{1-42}$ peptide (SEQ ID NO: 1) in the senile plaques. In other embodiments, Aβ peptide immunogen constructs contain hybrid peptide having a B cell antigenic site Aβ$_{1-14}$ peptide linked to heterologous Th epitopes derived from various pathogenic proteins (SEQ ID NOs: 33 to 47) capable of eliciting antibodies cross-reactive the full length Aβ$_{1-42}$ peptide in the senile plaques. Of the heterologous Th epitopes employed to enhance the B cell antigenic site Aβ$_{1-14}$ peptide, Th epitopes derived from natural pathogens Diphtheria Toxin (SEQ ID NO: 37), *Plasmodium Falciparum* (SEQ ID NO: 38), Cholera Toxin (SEQ ID NO: 40), and those idealized artificial Th epitopes derived from Measles Virus Fusion protein (MVF 1 to 5) and Hepatitis B Surface Antigen (HBsAg 1 to 3) in the form of either single sequence or combinatorial sequences (e.g. SEQ ID NOs: 34 and 41 to 47) are found of particular use in such B cell antigenicity enhancement through immunogenicity screening testing. In other embodiments, peptide compositions comprising a mixture of Aβ peptide immunogen constructs with heterologous Th epitopes derived from different pathogens are used to allow coverage of as broad a genetic background in patients leading to a higher percentage in responder rate upon vaccine immunization for the treatment and prevention of dementia of the Alzheimer's type. In an embodiment, Aβ peptide immunogen constructs (SEQ ID NOs: 62 and 63) with heterologous Th epitopes derived from MVF and HBsAg in a combinatorial form (SEQ ID NOs: 44 and 45) were mixed in an equimolar ratio for use in a vaccine formulation to allow for maximal coverage of the vaccine host population having diverse genetic background. Synergistic enhancement in Aβ peptide immunogen constructs was observed in the peptide compositions of this invention and the antibody response was mostly (>90%) focused on the desired cross-reactivity against the full length Aβ$_{1-42}$ without much, if any, directed to the heterologous Th epitopes employed for immunogenicity enhancement. This is in sharp contrast to the conventional protein or other biological carriers used for such peptide antigenicity enhancement. In another embodiment, highly purified Aβ peptide immunogen constructs (SEQ ID NOs: 64 and 65) with heterologous Th epitopes derived from MVF and HBsAg in a single sequence form (SEQ ID NOs: 46 and 47) were mixed optionally in an equimolar ratio for use in a vaccine formulation to allow for maximal coverage of the vaccine host population having diverse genetic background.

The present disclosure is also directed to pharmaceutical compositions including vaccine formulations for treatment and prevention of dementia of the Alzheimer's type. In some embodiments, pharmaceutical compositions comprising a stabilized immunostimulatory complex, which is formed through mixing a CpG oligomer with a peptide composition containing a mixture of the Aβ peptide immunogen constructs through electrostatic association, to further enhance the AR peptide immunogenicity towards the desired cross-reactivity with the full length Aβ$_{1-42}$ present in the senile plaques. In other embodiments, pharmaceutical compositions comprising a peptide composition of a mixture of the AR peptide immunogen constructs in contact with mineral salts including Alum gel (Al(OH)$_3$, aluminum hydroxide gel) (ALHYDROGEL®; Brenntag, Frederikssund, Denmark) or Aluminum phosphate (AlPO$_4$) ADJU-PHOS®; Brenntag, Frederikssund Denmark) as adjuvant to form a suspension vaccine formulation was used for administration to vaccine hosts. In yet another embodiment, pharmaceutical compositions comprising a peptide composition of a mixture of the Aβ peptide immunogen constructs forming a stabilized immunostimulatory complex with CpG oligomers are, optionally, mixed with mineral salts, including Alum gel or Aluminum phosphate (ADJU-PHOS®) as an adjuvant with high safety factor, to form a suspension vaccine formulation for administration to vaccine hosts.

The present disclosure also includes methods for treatment and prevention of dementia of the Alzheimer's type. The disclosed methods utilize pharmaceutical compositions including a suspension vaccine formulation comprising the Aβ peptide immunogen constructs of this invention, optionally forming a stable immunostimulatory complex with CpG oligomers, which are further supplemented, optionally, with mineral salts as adjuvant, for administration to patients at risk or with Alzheimer's Disease. In these embodiments, the pharmaceutical compositions that comprise the Aβ peptide immunogen constructs and the vaccine formulations derived thereof can elicit antibodies against the full length Aβ$_{1-42}$ peptide to inhibit, in vitro, fibril formulation, and reduce, in vitro, the cytotoxicity towards the neuronal cells, as illustrated by the PC12 cell line cells, mediated by the aggregated Aβ oligomers. In some embodiments, animals or patients receiving vaccine formulations derived from the Aβ peptide immunogen constructs developed significant antibodies against the full length Aβ$_{1-42}$ peptide and were found to pull such toxic Aβ peptide from the Central Nervous System into periphery as demonstrated in the elevated levels of Aβ$_{1-40}$ in the plasma and serum of the vaccine hosts.

In another aspect of the present invention, it was surprisingly found that the vaccine formulations comprising Aβ peptide immunogen constructs can be advantageously applied intramuscularly to warm-blooded animals, especially humans, suffering from dementia of the Alzheimer's type. In yet another aspect of the present invention, it provides a dosage form for intramuscularly administration of two Aβ peptide immunogen constructs (SEQ ID NOs: 64 and 65). The preferred dosage form for intramuscular injection is a vaccine formulation containing between 30 µg to 1000 µg/0.5 mL peptide immunogen constructs complexed with CpG oligomers supplemented with 0.5 mL mineral salts as the adjuvant, preferably between 100 µg to 400 µg/0.5 mL, and more preferably 300 µg/0.5 mL. The dosage form is stable for more than 2 years and can be kept at 2 to 8° C. until shortly before usage. The dosage form is administered preferably by intramuscular injection with a syringe to the warm-blooded animal, especially into the arm. For warming up of the dosage form, the dosage form can be kept at ambient temperature for about between 15 minutes and 45 minutes, e.g. 30 minutes. Preferably, before withdrawing drug substance, the vials are gently inverted several times for dispersion of potential sub-visual particles.

In another aspect of the present invention, it was surprisingly found that the vaccine formulations comprising Aβ peptide immunogen constructs can be advantageously applied intramuscularly to warm-blooded animals, especially rhesus macaques and humans suffering from dementia of the Alzheimer's type to elicit highly specific antibodies mainly directed against the N-terminus of the Aβ peptide represented by Aβ$_{1-10}$ peptide with the amino acid "Aspartic Acid (D)" exposed on the outer part of the Aβ$_{1-42}$ peptide oligomers, aggregates or in senile plaques as demonstrated by fine epitope mapping studies. In yet another aspect of the present invention, it was surprisingly found that the vaccine formulations comprising Aβ peptide immunogen constructs can be advantageously applied intramuscularly to warm-blooded animals, especially rhesus macaques and humans suffering from dementia of the Alzheimer's type to elicit highly specific antibodies mainly directed against the N-terminus of the Aβ$_{1-42}$ peptide in all animals and all patients receiving such vaccine formulations, thus achieving a 100% antibody response rate, extremely rare in the vaccine development history. In yet another aspect of the present invention, it was surprisingly found that the vaccine formulations comprising Aβ peptide immunogen constructs of this invention can be advantageously applied intramuscularly to patients at age 60 or older and in the mild Alzheimer's Disease category clinically, with significant improvement in cognition scores (ADAS-Cog, ADCS-CGIC, MMSE), unprecedented since the immunotherapy of patients with Alzheimer's Disease was first explored.

In yet another aspect of the present invention, it relates to a method of prevention and treatment of dementia of Alzheimer's type in human patients comprising administering 30 µg to 750 µg, preferably 100 µg to 400 µg, more preferably about 300 µg, to human patients in need thereof about once every 12 weeks, preferably about once every 26 weeks, and in particular about once every 52 weeks, depending on the patient's antibody response directed at the full length Aβ peptide, after a priming with three injections at 0, 4, and 8 weeks after the initial immunization.

The usefulness of the vaccine formulations and the Aβ peptide immunogen constructs in the treatment of the above-mentioned disorders can be further confirmed in suitable clinical studies, e.g. those described in the Examples, e.g. applying a total of three dosages at 0, 4, and 12 weeks with each time applying 300 µg/0.5 mL/dose vaccine formulation for over 9 months period followed. There can be a follow up immunizations of once every three, six or 12 months according to antibody titers.

Suitable clinical studies are open label studies or in particular randomized, double-blind, placebo-controlled, parallel studies in patients at risk of Alzheimer's Disease or with symptoms of Alzheimer's Disease.

The present disclosure also provides a method for the low cost manufacture and quality control of Aβ peptide immunogen constructs, as well as a delivery system capable of protecting animals and patients at risk for or with Alzheimer's Disease.

In a further aspect, the present invention provides human monoclonal antibodies against Aβ$_{1-42}$ induced by patients receiving the vaccine formulations of the Aβ peptide immunogen constructs of this instant invention. An efficient method to make human monoclonal antibodies from B cells isolated from the blood of a human patient is described by Elisabetta Traggiai et al, in *Nature Medicine* 10, 871-875 (2004), which publication is included by reference.

REFERENCES

Green R C, Schneider L S, Amato D A, et al., "Effect of Tarenflurbil on Cognitive Decline and Activities of Daily Living in Patients with Mild Alzheimer Disease." *Journal of the American Medical Association* 2009; 302(23):2557-2564.

Hardy J. Amyloid, "The Presenilins, and Alzheimer's Disease." *Trends in Neurosciences* 1997; 20(4):154-159.

Hartmann T, Bieger S C, Bruhl, et al. "Distinct sites of intracellular production for Alzheimer's disease Abeta40/42 amyloid peptides." *Nature Medicine* 1997: 3(9):1016-1020.

Katial R K, Sachanandani D, Pinney C, Lieberman M M. "Cytokine production in cell culture by peripheral blood mononuclear cells from immunocompetent hosts." *Clinical and Diagnostic Laboratory Immunology* 1998; 5(1): 78-81.

Lacor P N. "Advances on the understanding of the origins of synaptic pathology in Alzheimer's disease." *Current Genomics* 2007; 8(8):486-508.

Moore V, Chapter 2. In: *Synthetic Peptides: A Users Guide*. Grant G A, ed. New York: WH Freeman and Company: 1992; 63-67.

Morgan D. "Immunotherapy for Alzheimer's Disease." *Journal of Internal Medicine* 2011; 269(1):54-63.

Orgogozo J M, Gilman S, Dartigues J F, et al. "Subacute meningoencephalitis in a subset of patients with AD after Abeta42 immunization." *Neurology* 2003; 61(1):46-54.

Rockenstein E M, McConlogue L, Tan H, et al. "Levels and alternative splicing of amyloid beta protein precursor (APP) transcripts in brains of APP transgenic mice and humans with Alzheimer's disease." *Journal of Biological Chemistry.* 1995; 270(47):28257-28267.

Rockenstein E, Mallory M, Mante M, et al. "Early formation of mature amyloid-beta protein deposits in a mutant APP transgenic model depends on levels of A-beta(1-42)." *Journal of Neuroscience Research* 2001; 66(4):573-582.

Sokoll K K. "Stabilized synthetic immunogen delivery system," In U.S. Patent Application Publication No US 2004/0009897 A1. United States: United Biomedical Inc.; 2004.

Solomon B, Koppel R, Frankel D, Hanan-Aharon E. "Disaggregation of Alzheimer beta-amyloid by site directed mAb." *Proceedings National Academy of Sciences USA.* 1997; 94(8):4109-4112.

Tabira, T. "Immunization therapy for Alzheimer disease: a comprehensive review of active immunization strategies." *Tohoku Journal of Experimental Medicine* 2010; 220(2): 95-106.

Traggiai E, Becker S, Subbarao K, et al. "An efficient method to make human monoclonal antibodies from memory B cells." *Nature Medicine* 2004; 10(8): 871-875.

Wang C Y. "Artificial T helper epitopes as immune stimulators for synthetic peptide immunogens." U.S. Pat. No. 6,713,301 B1. United States: United Biomedical Inc.; 2004.

Wang C Y "Immunogenic peptide composition comprising measles virus F protein T helper cell epitope (MVHTh1-16) and N-terminus of beta-amyloid peptide." U.S. Pat. No. 6,906,169, United States: United Biomedical Inc.; 2005.

Wang C Y "Immunogenic peptide composition comprising a promiscuous helper T cell epitope and an N-terminal fragment of Abeta(1-42) peptide." U.S. Pat. No. 7,951,909, United States: United Biomedical Inc.; 2011.

Wang C Y "Immunogenic peptide composition for the prevention and treatment of Alzheimer's disease." U.S. Pat. No. 8,232,373, United States: United Biomedical Inc.; 2012.

Wang C Y, Finstad C L, Walfield A M, et al. "Site-specific UBITh amyloid-beta vaccine for immunotherapy of Alzheimer's disease." *Vaccine* 2007; 25 (16): 3041-3052.

Wang C Y, Looney D J, Li M L, et al. "Long-term high-titer neutralizing activity induced by octameric synthetic HIV-1 antigen." *Science* 1991; 254(5029):285-288.

Wang C Y, Walfield A M. "Site-specific peptide vaccines for immunotherapy and immunization against chronic diseases, cancer, infectious diseases, and for veterinary applications." *Vaccine* 2005; 23 (17-19):2049-2056.

DETAILED DESCRIPTION OF THE INVENTION

Figure 1:
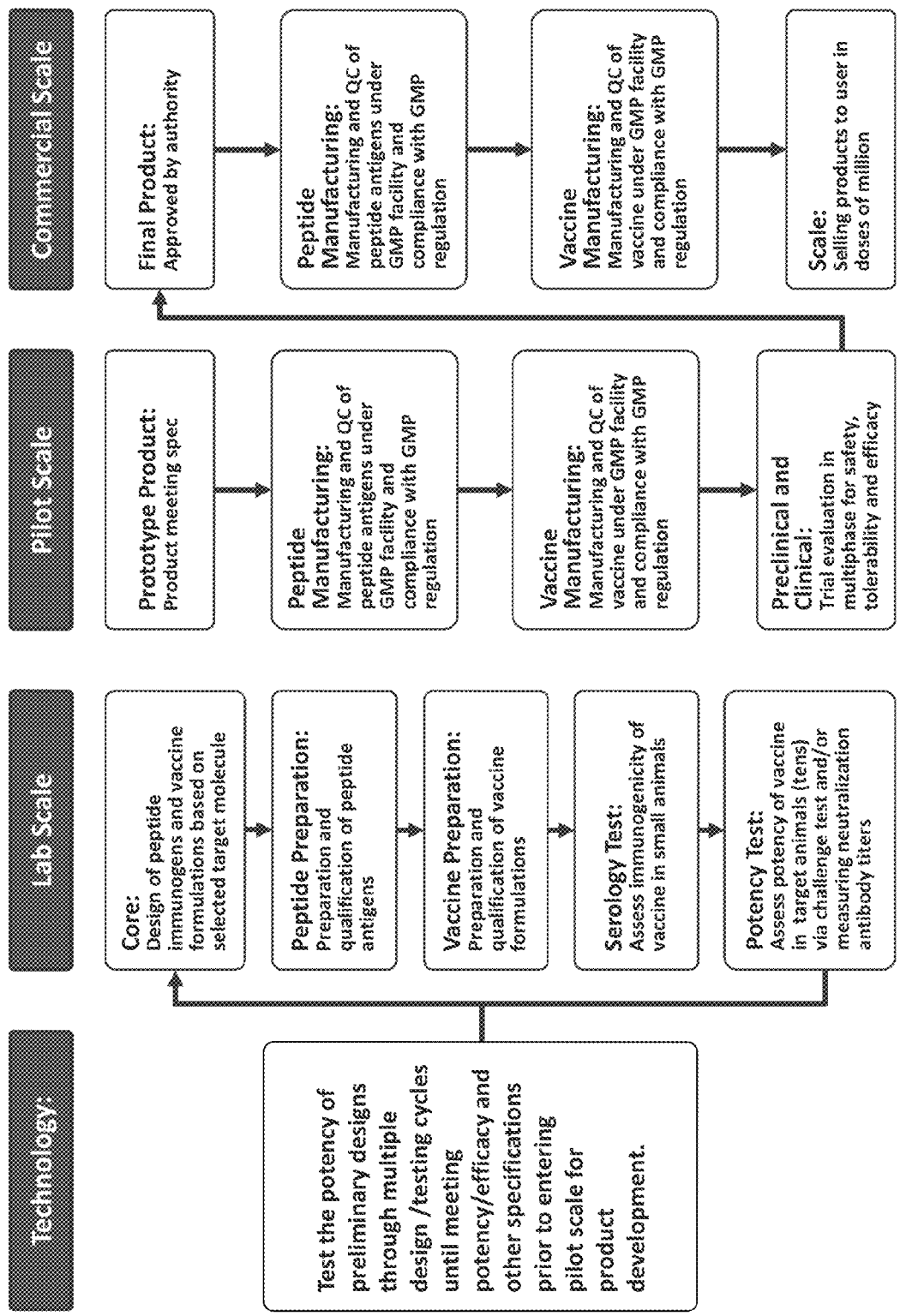
FIG. 1 is a flow chart identifying the development process, from discovery to commercialization (industrialization), of a vaccine formulation according to a particular embodiment disclosed herein. The present disclosure includes peptide immunogen design, peptide composition design, vaccine formulation design, in vitro functional antigenicity design, in vivo immunogenicity and efficacy study design, dosing regimen design, and clinical protocol design summarized in this chart. Detailed evaluation for each of the steps, with pleasant and unpleasant surprises, leading to final success in commercialization of a highly safe and efficacious vaccine formulation based on rational designs is described further herein.

The present disclosure is directed to individual Aβ peptide immunogen constructs, peptide compositions comprising these Aβ peptide immunogen constructs and mixtures thereof, pharmaceutical compositions comprising these peptide compositions in a vaccine formulation, with the individual Aβ peptide immunogen constructs having N-terminus of Aβ peptide ($A\beta_{1-10}$ to $A\beta_{1-14}$) as B cell (B) epitopes linked through spacer residue(s) to heterologous T helper cell (Th) epitopes from proteins of pathogens that act together to stimulate the generation of specific antibodies directed against the N-terminus of the $A\beta_{1-42}$ peptide offering protective immune responses to patients at risk for, or with, Alzheimer's Disease.

The present disclosure also includes methods for treatment and prevention of Alzheimer's Disease. The disclosed methods utilize pharmaceutical compositions including a suspension vaccine formulation comprising the Aβ peptide immunogen constructs forming, optionally, a stable immunostimulatory complex with highly negatively charged oligonucleotide such as CpG oligomers through electrostatic association, which complexes are further supplemented, optionally, with mineral salts as adjuvant, for administration to patients at risk for, or with, Alzheimer's Disease. The present disclosure also includes methods utilizing vaccine formulations in particular to dosage regimens, modes of and dosage forms for the administration of the vaccine formulations comprising the Aβ peptide immunogen constructs for the prevention and treatment of patients at risk for, or with, Alzheimer's Disease.

The present disclosure also provides a method for the low cost manufacture and quality control of Aβ peptide immunogen constructs and a vaccine formulation capable of protecting animals and patients at risk for, or with, Alzheimer's Disease. The present invention relates to a stabilized immunostimulatory complex and a method for preparing the stabilized immunostimulatory complex. More specifically, the present invention provides stabilized synthetic immunostimulatory complexes comprising the Aβ peptide immunogen constructs and highly negatively charged oligonucleotide such as CpG oligomers that are useful in vaccine delivery systems with improved immune responses in vivo. These immunostimulatory complexes are also useful for preparing vaccine formulations designed to function as a depot for controlled release.

In a further aspect, the present invention provides human monoclonal antibodies against $A\beta_{1-42}$ induced by B cells isolated from the blood of a patient who previously received the vaccine formulations of the Aβ peptide immunogen constructs of this instant invention.

(a) Amyloid Beta (Aβ) Peptide

The article in Wikipedia entitled "Beta amyloid" provides an updated review of the subject (en.wikipedia.org/wiki/Beta_amyloid). The internet link to this article is provided here as a reference.

Amyloid beta (Aβ or Abeta) is a peptide of 36-43 amino acids that is processed from the Amyloid precursor protein. Aβ is the main component of deposits found in the brains of patients with Alzheimer's disease. Evidence has also been found that Aβ is a highly multifunctional peptide with significant non-pathological activity.

Aβ is formed after sequential cleavage of the amyloid precursor protein (APP), a transmembrane glycoprotein of undetermined function. APP can be processed by α-, β- and γ-secretases; Aβ protein is generated by successive action of the β and γ secretases. The γsecretase, which produces the C-terminal end of the Aβ peptide, cleaves within the transmembrane region of APP and can generate a number of isoforms of 36-43 amino acid residues in length. The most common isoforms are $A\beta_{1-40}$ (SEQ ID NO: 2) and $A\beta_{1-42}$ (SEQ ID NO: 1); the longer form is typically produced by cleavage that occurs in the endoplasmic reticulum, while the shorter form is produced by cleavage in the trans-Golgi network (Hartmann T, et al., 1997; Nature Medicine 3:1016-1020). The $A\beta_{1-40}$ form is the more common of the two, but $A\beta_{1-42}$ (SEQ ID NO: 1) is the more fibrillogenic and is thus associated with disease states.

Autosomal-dominant mutations in APP cause hereditary early-onset Alzheimer's disease (familial AD or FAD). This form of AD only accounts for no more than 10% of all cases, and the vast majority of AD is not accompanied by such mutations. However, familial Alzheimer disease is likely to result from altered proteolytic processing. Increases in either total $A\beta$ levels or the relative concentration of both $A\beta_{1-40}$ and $A\beta_{1-42}$ (where the former is more concentrated in cerebrovascular plaques and the latter in neuritic plaques) have been implicated in the pathogenesis of both familial and sporadic Alzheimer's disease.

Due to its more hydrophobic nature, the $A\beta_{1-42}$ is the most amyloidogenic form of the peptide. However the central sequence KLVFFAE ($A\beta_{16-22}$) (SEQ ID NOs: 31) is known to form amyloid on its own, and probably forms the core of the fibril.

The "amyloid hypothesis" that the plaques are responsible for the pathology of Alzheimer's disease is accepted by the majority of researchers. An alternative hypothesis is that amyloid oligomers rather than plaques are responsible for the disease. Mice that are genetically engineered to express oligomers but not plaques ($APP^{E693Q}$) develop the disease. Furthermore mice that are, in addition, engineered to convert oligomers into plaques ($APP^{E693Q}$ X PS1ΔE9), are no more impaired than the oligomer only mice. Atomic force microscopy, which can visualize nanoscale molecular surfaces, can be used to determine the aggregation state (oligomers) of $A\beta$ peptide in vitro.

There are many different ways to measure Amyloid beta. It can be measured semi-quantitatively with immunohistochemical staining, which also allows for location determination. $A\beta$ may be primarily vascular, as in cerebral amyloid angiopathy, or in senile plaques and vascular areas.

One highly sensitive method to measure $A\beta$ is through a quantitative enzyme immunosorbent assay (qELISA), which utilizes a pair of antibodies that recognize $A\beta$.

Imaging compounds, notably Pittsburgh compound B, (6-OH-BTA-1, a thioflavin) and florbetapir F18 (18F-AV-45), can selectively bind to amyloid beta in vitro and in vivo. This technique, combined with Positron emission tomography (PET) imaging, has been used to image areas of plaque deposits in patients with Alzheimer's disease.

(b) B Cell Epitopes: N-Terminus of the $A\beta$ Peptide

This invention is directed to a novel peptide composition for the generation of high titer oligoclonal antibodies with specificity for the N-terminus of the $A\beta$ peptide, with cross-reactivities to the soluble $A\beta_{1-42}$ and the plaques in the brain of AD patients. The site-specificity of the peptide composition through efforts of rational designs minimizes the generation of antibodies that are directed to irrelevant sites on carrier proteins.

Table 1 provides a number of short linear peptides including peptide fragment(s) from the N-terminus of $A\beta_{1-42}$. The $A\beta_{1-42}$ (SEQ ID NO: 1) and $A\beta_{1-28}$ (SEQ ID NO: 3) peptides are sufficiently long enough to elicit an immune response without the need of a carrier protein. However, the shorter N-terminal $A\beta$ peptides, such as $A\beta_{1-14}$, $A\beta_{1-12}$, $A\beta_{1-10}$ (SEQ ID NOs: 4 to 6), are non-immunogenic on their own, as shown in Table 4 of Example 7 (compare group 3 with groups 1 and 2 in the immunogenicity study). This result confirms the presence of an autologous T helper cell epitope (Th) between amino acids 15 to 28 that renders the $A\beta_{1-28}$ peptide immunogenic. The short $A\beta$ fragments can be immunopotentiated by chemical coupling to a carrier protein, for example, Keyhole Limpet Hemocyanin (KLH) as shown in Group 4 of Table 6 in Example 7. Major deficiencies of such "$A\beta$ peptide(s)-carrier" vaccines is that most (>90%) of antibodies generated by the combinations are the non-functional antibodies directed against the carrier protein KLH, as shown in Table 6, Group 4 of Example 7 and the potential for epitopic suppression.

The peptide immunogens of the present invention include 10 to 14 amino acids (10- to 14-mer) of the N-terminal fragment of the $A\beta$ peptide, beginning with the amino acid Asp (D) at position 1. The wholly synthetic peptide immunogens comprising these $A\beta$ peptide fragments also contain selected T helper cell epitopes (Th) (e.g. SEQ ID NOs: 33-47) having multiple MHC Class II binding motifs, which elicit an immune response that is exclusively focused at the N-terminus target sites on the $A\beta_{1-42}$ peptide with high cross-reactivities to the $A\beta_{1-42}$ peptide and the senile plaques in the brain of AD patients.

(c) Heterologous T Helper Cell Epitopes (Th Epitopes)

T cell epitopes are presented on the surface of an antigen-presenting cell, where they are bound to MHC molecules. T cell epitopes presented by MHC class I molecules are typically peptides between 8 and 11 amino acids in length, whereas MHC class II molecules present longer peptides, 13-17 amino acids in length, and non-classical MHC molecules also present non-peptidic epitopes such as glycolipids.

T helper cells (Th cells) are a subgroup of lymphocytes, a type of white blood cell, that play an important role in the immune system, particularly in the adaptive immune system. They help the activity of other immune cells by releasing T cell cytokines. They are essential in B cell antibody class switching, in the activation and growth of cytotoxic T cells, and in maximizing bactericidal activity of phagocytes such as macrophages.

T helper cell epitopes (Th epitopes) are the T cell epitopes that are presented on the surface of an antigen-presenting cell, where they are bound to MHC class II molecules and are 13 to 17 amino acids in length, which are specifically recognized by T helper cells, as described above.

Peptides binding to Major Histocompatibility Complex (MHC) class II molecules are crucial for initiation and regulation of immune responses. Predicting peptides that bind to a specific MHC molecule plays an important role in determining potential candidates for vaccines. The binding groove in class II MHC is open at both ends, allowing peptides longer than 9-mer to bind. Finding the consensus motif facilitating the binding of peptides to a MHC class II molecule is difficult because of different lengths of binding peptides and varying location of 9-mer binding core. The level of difficulty increases when the molecule is promiscuous and binds to a large number of low affinity peptides.

Over the past two decades, this inventor and her team have identified many potential Th epitopes with promiscuous binding motifs to MHC class II molecules of different species (e.g., human, pig, cattle, etc.) from proteins of many pathogens for use as heterogeneous Th epitopes for the design of peptide immunogen constructs (Wang C Y, 2004; U.S. Pat. No. 6,713,301 B1 and Wang C Y, 2005; U.S. Pat. No. 6,906, 169) where specific target B cell epitopes (e.g., Aβ peptide fragments) are linked at either N or C-terminus to such Th epitopes for enhanced immunogenicity generating specific high titer antibodies directed against the B cell epitopes through rational design (5, 6). It is to be emphasized that all rationally designed immunogens employed in a vaccine are to be validated for the effectiveness of such Th epitopes through experimental immunization as part of a screening process (e.g. Example 7, Tables 4, 5, 6 and 7) to select the optimal Th epitopes for use in vaccine formulations. An ideal Th epitope will comprise multiple promiscuous MHC class II binding motifs to allow maximal activation of T helper cells leading to initiation and regulation of immune responses, and are usually immunosilent on their own, i.e. none of the antibodies generated by the immunogen constructs will be directed towards the Th epitopes (e.g., Groups 1, 2 and 3 of Table 6 of Example 7; and Group 1 of Table 7 in Examples 8 and 9), thus allowing very focused immune responses to be directed mostly towards the targeted B cell epitopes.

Th refers to a sequence of amino acids (natural or non-natural amino acids) that comprises a Th epitope. The Th domain of the subject peptides is about 9 to about 25 amino acids, preferably from about 13 to about 17 amino acids. A Th segment and functional immunological analogues thereof comprises a contiguous portion of a Th epitope that is sufficient to enhance or stimulate an immune response to the N-terminal fragment of $A\beta_{1-42}$ peptide from about 10 to about 14 amino acid residues (SEQ ID NOs: 4 to 6).

Th epitopes of the present invention include but are not limited to those derived from foreign pathogens as exemplified in Table 2 (SEQ ID NOs: 33-41). Further, Th epitopes include idealized artificial Th and idealized artificial combinatorial Th (SEQ ID NOs: 42-47). Peptides comprising combinatorial Th are produced simultaneously in a single solid-phase peptide synthesis in tandem with N-terminus Aβ peptide(s) sequences. Th sites also include immunological analogs Immunological Th analogues include immune-enhancing analogs, cross-reactive analogs and segments of any of these Th epitopes. Functional immunological Th analogues further include conservative substitutions, additions, deletions and insertions of from one to about five amino acid residues in the Th epitope which do not essentially modify the Th-stimulating function of the Th epitope as best illustrated in the several versions of the Th epitope derived from Measles Virus Fusion protein MVF1-5 Ths (SEQ ID NOs: 34, 41, 42, 44 and 46) and from Hepatitis B Surface Antigen HBsAg 1-3 Ths (SEQ ID NOs: 43, 45, 47).

The Aβ peptide immunogen constructs of this invention have the Th epitope from about 13 to about 20 amino acid residues covalently attached through "spacer A" to the C terminus of the N-terminal fragment of $A\beta_{1-42}$ peptide, as well as cross-reactive or functional analogues thereof. Cross-reactive and functional analogues of the Aβ peptide immunogen constructs (e.g., SEQ ID NOs: 48 to 65) according to the invention, may further comprise conservative substitutions, additions, deletions, or insertions of from one to about five amino acid residues provided that the peptide analogues are capable of eliciting immune responses cross-reactive with the $A\beta_{1-42}$ peptides. The conservative substitutions, additions, and insertions can be accomplished with natural or non-natural amino acids as defined herein.

Preferred peptide immunogens of this invention are the peptides containing the N-terminal fragment of the $A\beta_{1-42}$ peptide (SEQ ID NOs: 4 to 6) or cross-reactive immunological analogues thereof; a spacer (e.g. ε-Lys, Gly, or ε-Lys-Lys-Lys); and a Th epitope that is selected from those in Table 2 (SEQ ID NOs: 34, 37, 38, 40-47) (see immunogenicity testing results in Table 4 of Example 7).

Functional immunologically analogues (e.g. various sequences of MvF Ths, SEQ ID NOs: 34, 41, 42, 44, and 46; and HBsAg Ths, SEQ ID NOs: 43, 45, 47) of the Th epitope peptides are also effective and included as part of the present invention. Functional immunological analogs of Aβ peptide immunogen constructs include variants of SEQ ID NOs: 49-51, 54-55, 57-65 and/or homologues of SEQ ID NOs: 49-51, 54-55, 57-65 that retain substantially the same immunogenicity as the original peptide SEQ ID NOs: 51 and 60. For example, variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In a particular embodiment, the functional analogue has at least 50% identity to the original amino acid sequence. In another embodiment, the functional analogue has at least 80% identity to the original amino acid sequence. In yet another embodiment, the functional analogue has at least 85% identity to the original amino acid sequence. In still another embodiment, the functional analogue has at least 90% identity to the original amino acid sequence.

In one embodiment, the functional immunological analogue of a particular peptide contains the same amino acid sequence as the original peptide and further includes three lysines (Lys-Lys-Lys) added to the amino terminus of the peptide. In this embodiment, the inclusion of three lysines to the original peptide sequence changes the overall charge of the original peptide, but does not alter the function of the original peptide as illustrated in the MVF Th peptide series (Tables 2 to 7).

Table 2 identifies another variation of a functional analogue for Th epitope peptide. In particular, SEQ ID NOs: 34 and 41 of MVF1 Th and MVF2 Th are functional analogues of SEQ ID NOs: 44 and 46 of MVF4 Th and MVF5 Th in that they differ in the amino acid frame by the deletion (SEQ ID NOs: 34 and 41) or the inclusion (SEQ ID NOs: 44 and 46) of two amino acids each at the N- and C-termini. The differences between these two series of analogous sequences would not affect the function of the Th epitopes contained within these sequences (e.g. Groups 7, 8, 14 of Table 4 in Example 7 vs. Group 1 of Table 5 in Example 7 and Group 1 of Table 7 in Example 8).

In other variations, the heterologous Th epitope peptides can be presented as a combinatorial sequence, which contains a mixture of amino acid residues represented at specific positions within the peptide framework based on the variable residues of homologues for that particular peptide. An assembly of combinatorial peptides can be synthesized in one process by adding a mixture of the designated protected amino acids, instead of one particular amino acid, at a specified position during the synthesis process. Such combinatorial heterologous Th epitope peptides assemblies can allow broad Th epitope coverage for animals having a diverse genetic background. Representative combinatorial sequences of heterologous Th epitope peptides include SEQ ID NOs: 42 to 45, which are shown in Table 2. Th epitope peptides of the present invention provide broad reactivity and immunogenicity to animals and patients from genetically diverse populations.

Generally, the Aβ peptide immunogen construct of this invention is represented by the following formula:

(N-terminal fragment of Aβ$_{1-42}$ peptide)-(A)$_o$-(Th)-X wherein (N-terminal fragment of Aβ$_{1-42}$ peptide) is a B cell epitope selected from the group consisting of SEQ ID NOs: 4 to 6 from about 10 to about 14 amino acid residues;

each A is independently an amino acid or a linking group chosen from the group consisting of an amino acid, Lys-, Gly-, Lys-Lys-Lys-, (α, ε-N)Lys, or ε-N-Lys-Lys-Lys (SEQ ID NOs: 32);

each Th comprises an amino acid sequence that constitutes a helper T cell epitope selected from the group consisting of SEQ ID NOs: 34, 37, 38, 40 to 47 and functional immunological analogues thereof;

X is an α-COOH or α-CONH$_2$ of an amino acid; and o is from 0 to about 4.

The Aβ peptide immunogen construct of the present invention comprises from about 20 to about 50 amino acid residues, preferably from about 25 to about 40 amino acid residues.

The conformational separation provided by a spacer (A) permits more efficient interactions between the presented Aβ peptide immunogen construct and the appropriate Th cells and B cells and thus enhances the immunogenicity of the Aβ peptide immunogen constructs or cross-reactive functional immunological analogues thereof.

(d) Compositions (i) Peptide Compositions:

Compositions of the present disclosure can contain one or more Aβ peptide immunogen constructs. Peptide compositions that comprise a mixture of the Aβ peptide immunogen constructs with two or more of the Th epitopes can be prepared in a pharmaceutical/vaccine formulation to allow for synergistic enhancement of the immunoefficacy in a broader genetic population due to a broader MHC class II coverage. Such compositions can provide an improved immune response to the Aβ$_{1-42}$ peptide fragments.

For example, the compositions can contain Aβ peptide immunogen constructs as shown in Table 3 (SEQ ID NOs: 48 to 65), homologues, analogues and/or combinations thereof. More specifically, peptide compositions can contain Aβ peptide immunogen constructs having the sequence selected from SEQ ID NOs: 62, 63, 64 and 65, homologues, analogues and/or combinations thereof (e.g. SEQ ID NOs: 62 and 63 as an equimolar mixture as shown in Example 7 or SEQ ID NOs: 64 and 65 as another equimolar mixture in Examples 8, 9, and 10).

(ii) Pharmaceutical Compositions:

The present disclosure is also directed to compositions containing a mixture of Aβ peptide immunogen constructs that are pharmaceutical compositions for treating and/or preventing dementia of the Alzheimer's type in patients at risk for, or with, AD.

Compositions can be prepared in liquid form (e.g., solutions or suspensions). Typically, compositions are prepared as injectables, either as liquid solutions or suspensions. Liquid vehicles prior to injection can also be prepared. Additional formulations suitable for other modes of administration include oral and intranasal applications. Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated.

The pharmaceutical compositions are formulated to contain an effective amount of Aβ peptide immunogen construct and a pharmaceutically acceptable carrier. The pharmaceutical compositions are also formulated in a suitable dosage unit form generally containing from about 0.5 µg to about 1 mg of the immunogen per kg body weight. When delivered in multiple doses, the pharmaceutical compositions may be conveniently divided into an appropriate amount per dosage unit form. The administered dosage will depend on the age, weight and general health of the subject as is well known in the vaccine and therapeutic arts.

(iii) Pharmaceutical Vaccine Formulations:

In certain embodiments, a pharmaceutical composition comprising Aβ peptide immunogen constructs is used to elicit an immune response to the N-terminus of the Aβ peptide in a vaccine host. Pharmaceutical compositions containing Aβ peptide immunogen constructs of the present invention can be used as a vaccine for prevention and treatment of dementia of Alzheimer's type for vaccine hosts or patients at risk for, or with, AD.

Additionally, compositions can contain carriers and/or other additives in a pharmaceutically acceptable delivery system. Accordingly, a composition containing the AR peptide immunogen constructs can be formulated as a pharmaceutical vaccine formulation using adjuvants, pharmaceutically-acceptable carriers or other ingredients including immunological adjuvants routinely provided in vaccine formulations. An immunologic adjuvant is defined as "any substance that acts to accelerate, prolong, or enhance antigen-specific immune responses without having any specific antigenic effect in itself when used in combination with specific vaccine antigens." There are many known adjuvants in widespread use, including oils, aluminum salts, and virosomes. Two common salts including aluminum phosphate (e.g. ADJU-PHOS®) and aluminum hydroxide (e.g. ALHYDROGEL®) are the most common adjuvants in human vaccines. Methods for selecting mineral salts and determining the preferred concentration of mineral salt to employ or combinations thereof are well known to those skilled in the art.

Among other ingredients that can also be used as adjuvants in this invention include liposyn, saponin, squalene, L121, Emulsigen, monophosphoryl lipid A (MPL), QS21, ISA 35, ISA 206, ISA50V, ISA51, and ISA 720 as well as the other efficacious adjuvants and emulsifiers. In a particular embodiment, the delivery vehicle and adjuvant is Montanide™ ISA 51 (an oil vaccine adjuvant composition comprised of vegetable oil and mannide oleate for production of water-in-oil emulsions), TWEEN® 80 (also known as: Polysorbate 80 or Polyoxyethylene (20) sorbitan monooleate), a CpG oligonucleotide, and/or any combination thereof. In another embodiment, the pharmaceutical composition is a water-in-oil-in-water (i.e. w/o/w) emulsion with Emulsigen or Emulsigen D as the adjuvant.

Pharmaceutical compositions as vaccines can be formulated as immediate-release or sustained-release formulations. Additionally the pharmaceutical compositions can be formulated for induction of systemic or localized mucosal, immunity through immunogen entrapment and co-administration with microparticles. Such delivery systems are readily determined by one of ordinary skill in the art.

Various vaccine formulations containing Aβ peptide immunogen constructs of the present disclosure are effective for protecting and treatment of dementia of Alzheimer's type in vaccine hosts or patients at risk for, or with, AD.

(iv) Aβ Peptide Immunostimulatory Complexes:

In certain embodiments, the pharmaceutical composition can contain immunostimulatory complexes comprising (a) CpG oligonucleotide and (b) Aβ peptide immunogen constructs. Such immunostimulatory complexes are specifically adapted to act as an adjuvant and as a peptide immunogen stabilizer. The immunostimulatory complexes are in the form of a particulate, which can efficiently present Aβ peptide immunogen constructs to the cells of the immune system to produce an immune response. The immunostimulatory complexes may be formulated as a suspension for parenteral administration. The immunostimulatory complexes may also be formulated in the form of w/o emulsions, as a suspension in combination with a mineral salt or with an in-situ gelling polymer for the efficient delivery of the Aβ peptide immunogen constructs to the cells of the immune system of a vaccine host following parenteral administration, to produce an anti-Aβ immune response with protective benefit. The present invention is directed to a stabilized immunostimulatory complex comprising a cationic Aβ peptide immunogen construct and an anionic molecule or oligonucleotide or polynucleotide and combinations thereof and a method for stabilizing a cationic Aβ peptide immunogen construct by complexation with an anionic molecule or oligonucleotide or polynucleotide via electrostatic association. The stabilized immunostimulatory complex may be incorporated into a pharmaceutical composition as an immunogen delivery system.

An Aβ peptide immunogen construct being a "cationic peptide" as described herein refers to a peptide that is positively charged at a pH in the range of 5.0 to 8.0. The net charge on the peptide or peptide cocktails is calculated by assigning a +1 charge for each lysine (K), arginine (R) or histidine (H), a −1 charge for each aspartic acid (D) or glutamic acid (E) and a charge of 0 for the other amino acid within the sequence. The charge contributions from the N-terminal amine (+1) and C-terminal carboxylate (−1) end groups of each peptide effectively cancel each other when unsubstituted. The charges are summed for each peptide and expressed as the net average charge. A suitable peptide immunogen has a net average positive charge of +1. Preferably, the peptide immunogen has a net positive charge in the range that is larger than +2.

An "anionic molecule" as described herein refers to a molecule that is negatively charged at a pH in the range of 5.0-8.0. The net negative charge on the oligomer or polymer is calculated by assigning a −1 charge for each phosphodiester or phosphorothioate group in the oligomer. A suitable anionic oligonucleotide is a single-stranded DNA molecule with 8 to 64 nucleotide bases, with the number of repeats of the CpG motif in the range of 1 to 10. Preferably, the CpG immunostimulatory single-stranded DNA molecules contain 18-48 nucleotide bases, with the number of repeats of CpG motif in the range of 3 to 8.

More preferably the anionic oligonucleotide is represented by the formula: 5' $X^1CGX^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' $(X^3)_2CG(X^4)_2$ 3' wherein C and G are unmethylated; and $X^3$ is selected from the group consisting of A, T or G; and $X^4$ is C or T.

The resulting immunostimulatory complex is in the form of particles with a size typically in the range from 1-50 microns and is a function of many factors including the relative charge stoichiometry and molecular weight of the interacting species. The particulated immunostimulatory complex has the added advantage of providing adjuvantation and upregulation of specific immune responses in vivo. Additionally, the stabilized immunostimulatory complex is suitable for preparing vaccine formulations by various processes including water-in-oil emulsions, mineral salt suspensions and polymeric gels.

(e) Methods for Manufacturing

The present disclosure is also directed to methods for the manufacturing of the Aβ peptide immunogen constructs, compositions and pharmaceutical compositions, vaccine formulations for eliciting immune responses and protecting patients at risk for, or with, AD.

(i) Methods for the Manufacturing of the Aβ Peptide Immunogen Constructs.

The peptide immunogens of this invention can be made by chemical synthesis methods well known to the ordinarily skilled artisan. See, for example, Moore V. Chapter 2 in *Synthetic Peptides: A User's Guide*, ed. GA Grant, W. H. Freeman & Co., New York, N.Y., 1992, p. 63-67. Hence, peptides can be synthesized using the automated Merrifield techniques of solid phase synthesis with the α-$NH_2$ protected by either t-Boc or F-moc chemistry using side chain protected amino acids on, for example, an Applied Biosystems Peptide Synthesizer Model 430A or 431. Preparation of peptide constructs comprising combinatorial library peptides for Th epitopes can be accomplished by providing a mixture of alternative amino acids for coupling at a given variable position.

After complete assembly of the desired peptide immunogen, the resin is treated according to standard procedures to cleave the peptide from the resin and deblock the functional groups on the amino acid side chains. The free peptide is purified by HPLC and characterized biochemically, for example, by amino acid analysis or by sequencing. Purification and characterization methods for peptides are well known to one of ordinary skill in the art.

The immunogen of the present invention may also be prepared as a branched polymer by synthesis of the desired peptide construct directly onto a branched poly-lysyl core resin (Wang, et al., *Science,* 1991; 254:285-288).

The quality of peptides produced by this chemical process can be controlled and defined and, as a result, reproducibility of antigenicity, immunogenicity and yield can be assured. Detailed description of the manufacturing of the Aβ related peptide or peptide immunogen constructs through solid phase peptide synthesis is shown in Example 1.

During 25 years of experience in immunological applications of synthetic peptides, the applicant has found that the range in structural variability that allows for retention of an intended immunological activity is far more accommodating than the range in structural variability allowed for retention of a specific drug activity by a small molecule drug or the desired activities and undesired toxicities found in large molecules that are co-produced with biologically-derived drugs. Thus, peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final products employing these peptides.

The peptides can also be made using recombinant DNA technology including nucleic acid molecules, vectors, and/or host cells. As such, nucleic acid molecules encoding the Aβ peptide immunogen constructs and immunologically functional analogues of the Aβ peptide immunogen constructs and analogues/homologues thereof are also encompassed by the present disclosure as part of the present invention. Similarly, vectors, including expression vectors, comprising nucleic acid molecules as well as host cells containing the vectors are also encompassed by the present disclosure as part of the present invention.

Various exemplary embodiments also encompass methods of producing the Aβ peptide immunogen constructs and immunologically functional analogues of the Aβ peptide immunogen constructs. For example, methods can include a step of incubating a host cell containing an expression vector containing a nucleic acid molecule encoding an Aβ peptide immunogen constructs and/or immunologically functional analogue thereof under such conditions where the peptide and/or analogue is expressed. The longer synthetic peptide immunogens can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

(ii) Methods for the Manufacturing of Immunostimulatory Complexes

Figure 5A:
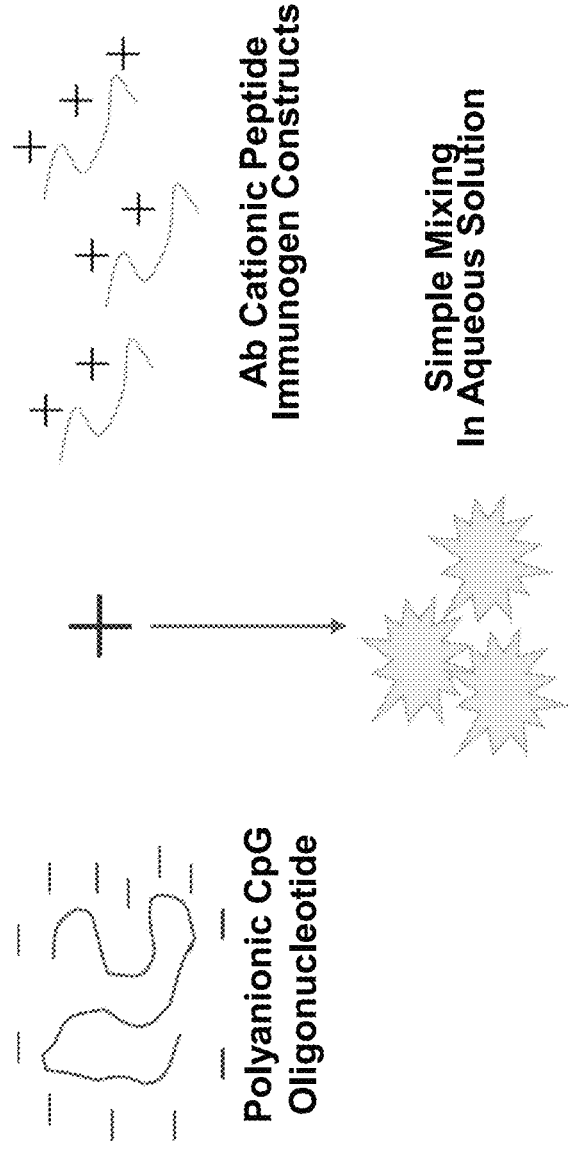
FIG. 5A illustrates a schematic for the preparation of stable peptide/CpG immunostimulatory complexes through electrocharge association/neutralization between the Aβ peptide immunogen constructs and CpG oligodeoxynucleotide (ODN).

Various exemplary embodiments also encompass methods of producing the Immuno-Stimulatory Complexes (ISC) comprising Aβ peptide immunogen constructs and CpG oligodeoxynucleotide (ODN) molecule. In one embodiment, as illustrated in FIG. 5A, stabilized immunostimulatory complexes are derived from cationic peptides and a polyanionic CpG ODN molecule. FIG. 5A illustrates a self-assembling system driven by electrostatic neutralization of charge. Stoichiometry of the molar charge ratio of cationic peptide to anionic oligomer determines extent of association. The non-covalent electrostatic association of peptide immunogens and CpG ODN is a completely reproducible process. The peptide/CpG ODN immunostimulatory complex self-aggregates and facilitates presentation to the "professional" antigen processing cells (APC) of the immune system thus further enhancing of the immunogenicity of the complexes. These complexes are easily characterized for quality control during manufacturing. The peptide/CpG ISC are well tolerated in vivo.

In one embodiment, the vaccine formulation (UBI AD vaccine) employs two Aβ peptide immunogen constructs (SEQ ID NOs: 64 and 65), prepared in an equimolar ratio, mixed with a proprietary CpG ODN which results in the spontaneous formation of immunostimulatory complexes in solution, as described in Examples 8 and 9. This novel particulate system comprising CpG ODN and Aβ peptide immunogen constructs, was designed to take advantage of the generalized B cell mitogenicity associated with CpG ODN use, yet promote balanced Th-1/Th-2 type responses.

The CpG ODN in the disclosed vaccine formulation is 100% bound to immunogen in a process mediated by electrostatic neutralization of opposing charge, resulting in the formation of micron-sized particulates. The particulate form allows for a significantly reduced dosage of CpG from the conventional use of CpG adjuvants, has less of a potential for adverse innate immune responses, and facilitates alternative immunogen processing pathways including antigen-presenting cells (APC). Consequently, the disclosed formulations (UBI AD vaccines) are novel conceptually and offer advantages by promoting the stimulation of immune responses by alternative mechanisms.

(iii) Methods for the Manufacturing of Vaccine Formulations.

Figure 5B:
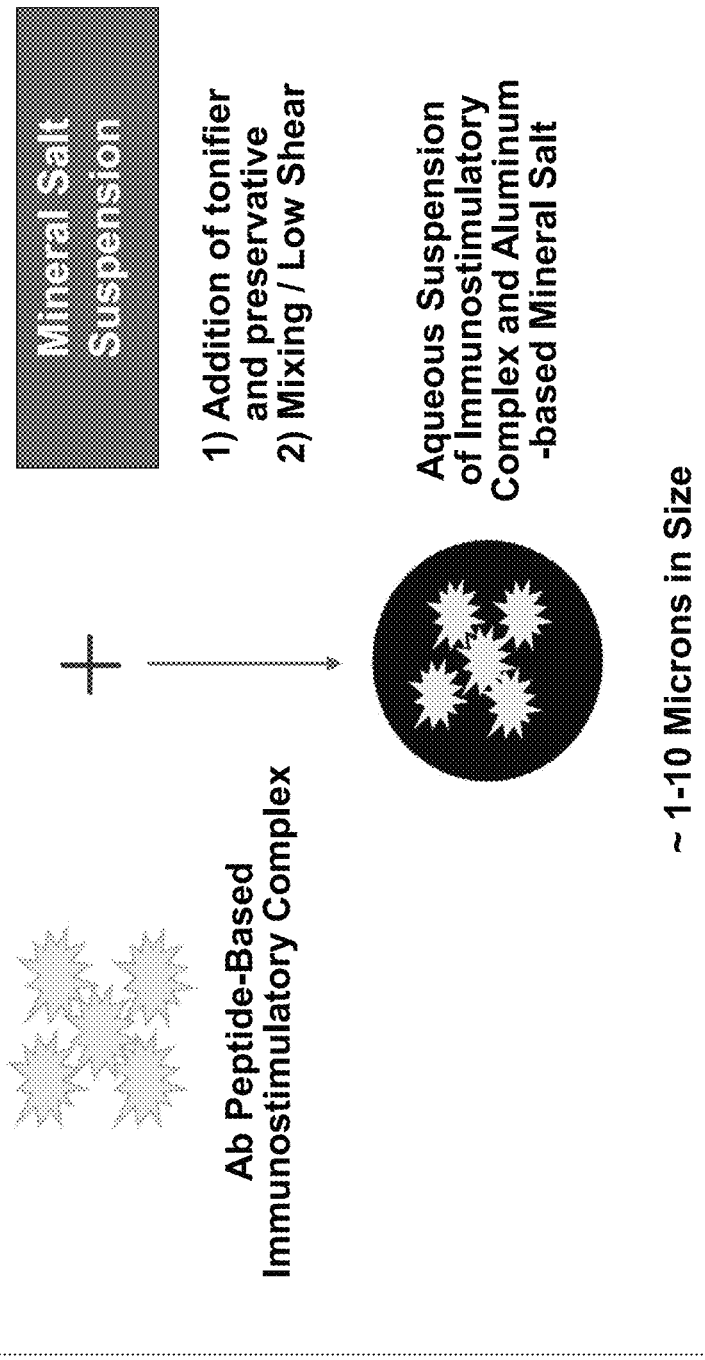
FIG. 5B illustrates a schematic subsequent to FIG. 5A for the preparation of mineral salt-based vaccine suspension containing such immunostimulatory complexes and aluminum-based mineral salt.

Various exemplary embodiments also encompass vaccine formulations employing water in oil emulsions and in suspension with mineral salts, as shown in FIG. 5B. In order for a vaccine designed to be used by a large population and with prevention also being part of the goal for administration, safety becomes another important factor for consideration. Despite the use of water-in-oil emulsions in humans for many vaccine formulations in clinical trials, Alum remains the major adjuvant for use in vaccine formulations due to its decades of safety testing. Alum or its mineral salts ADJU-PHOS® (Aluminum phosphate) were used as adjuvants in preparation for clinical applications, as illustrated in Examples 8 and 9.

(f) Methods for Treatment and Prevention of Alzheimer's Disease (i) Treatment Regimes In prophylactic applications, pharmaceutical compositions are administered to a patient susceptible to, or at risk of, Alzheimer's disease in an amount sufficient to eliminate or reduce the risk, lessen the severity, or delay the onset of the disease, (biochemical, histologic and/or behavioral), including its complications and intermediate pathological phenotypes in development of the disease.

In therapeutic applications, compositions are administered to a patient suspected of, or already suffering from, such a disease in an amount sufficient to cure, or at least partially arrest the symptoms of the disease (biochemical, histologic and/or behavioral), including its complications and intermediate pathological phenotypes in development of the disease.

In some methods, administration of agent reduces or eliminates mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

(ii) Patients Amenable to Treatment

Patients amenable to treatment include individuals who are at risk of developing Alzheimer's disease but not showing symptoms, as well as patients that are presently showing symptoms.

The term "prophylactic treatment" as used herein relates to a treatment aiming to halt pathogenic processes leading to disease.

The term "treatment" as used herein relates to a treatment aiming to halt pathogenic processes that lead to disease progression and/or has symptomatic effects.

Virtually every person is at risk of suffering from Alzheimer's disease if he or she lives long enough. Therefore, the present methods can be administered prophylactically to the general population without the need for any assessment of the risk of the subject patient (i.e., any living person can qualify as a patient). The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy J. *Trends in Neurosciences* 1997; 20:154-159). Other markers of risk are mutations in the presenilin genes, PS1 and PS2, and ApoE4, family history of AD, hypercholesterolemia or atherosclerosis.

In general, patients are selected from an at risk group of subjects consisting of patients with mild cognitive impairment, patients with genotypes known to be associated with Alzheimer's Disease, patients with Trisomy 21 (i.e. potential Down's syndrome patients), patients with surrogate markers indicating risk for Alzheimer's Disease.

In asymptomatic patients, treatment can begin at any age (e.g., 10, 20, 30 years). It is not necessary to begin treatment until a patient reaches 40, 50, 60 or 70 years. In the case of potential Down's syndrome patients, treatment can begin antenatally by administering therapeutic agent to the mother or shortly after birth.

Individuals presently suffering from Alzheimer's disease can be recognized from characteristic dementia, which, as used herein, relates in particular to a disease as defined according to the Diagnostic and Statistical Manual of Mental Disorders, 4th edition (DSM-IV) criteria, as well as the presence of risk factors described above. In addition, a number of diagnostic tests are available for identifying individuals who have AD. These include measurement of CSF tau and $A\beta_{1-42}$ levels. Elevated tau and decreased $A\beta_{1-42}$ levels signify the presence of AD. Individuals suffering from Alzheimer's disease can also be diagnosed by NINCDS-ADRDA Alzheimer's Criteria.

Treatment typically entails multiple dosages over a period of time. Treatment can be monitored by assaying antibody, or activated T-cell or B-cell responses to the therapeutic agent (e.g., $A\beta_{1-42}$ ELISA) over time. If the response falls, a booster dosage is indicated.

Considerable evidence has been accumulated suggesting that the Aβ-amyloid peptide, the major component of senile amyloid plaques, plays a causal role in AD. Successful disease-modifying therapy for AD is likely to include products that affect the deposition of β-amyloid in the brain. Aβ-specific antibodies, actively generated by the immune system or passively administered, consistently reduce plaque burden in different transgenic mouse models. A first clinical attempt to stimulate the immune system of AD patients to generate anti-Aβ antibodies, however, had to be suspended due to unacceptable side effects (meningoencephalitis in 6% of treated patients, Orgogozo J M, et al. *Neurology* 2003; 61: 46-54.).

Surprisingly, no adverse immune reactions or incidence of microhemorrhages are observed with the presently disclosed formulation (UBI AD vaccine) employing two $A\beta_{1-14}$ peptide immunogen constructs (SEQ ID NOs: 64 and 65), at an equimolar ratio, linked to two idealized artificial T helper epitopes derived from Measles Virus Fusion (MVF) protein and Hepatitis B Surface Antigen (HBsAg), respectively.

In one aspect of the disclosed method, it was surprisingly found that the Aβ peptide immunogen constructs advantageously can be applied intramuscularly to warm-blooded animals, especially humans, suffering from dementia.

In a second aspect, the present invention provides a dosage form for intramuscularly administration of the Aβ peptide immunogen constructs. The preferred dosage form for intramuscular of the Aβ peptide immunogen constructs is a vaccine formulation containing between 30 μg to 1000 μg/0.5 mL/dose peptide immunogen constructs in complexed with CpG ODN in the presence of mineral salts as the adjuvant, preferably between 100 μg to 400 μg/0.5 mL/dose, and more preferably 300 μg/0.5 mL/dose. The dosage form can be kept at 2 to 8° C. until shortly before usage. The dosage form is administered preferably by intramuscular injection with a syringe to the warm-blooded animal, especially into the arm. For warming up of the dosage form, the dosage form can be kept at ambient temperature for about between 15 minutes and 45 minutes, e.g. 30 minutes. Preferably, before withdrawing drug substance, the vials are gently inverted several times for dispersion of potential subvisual particles.

In a third aspect, the present invention relates to a method of prevention and treatment of dementia in human patients comprising administering 30 μg to 1000 μg/0.5 mL per dose, preferably 100 μg to 400 μg/0.5 mL per dose, more preferably about 300 μg/0.5 mL per dose, to human patients in need thereof about once every 12 weeks, preferably about once every 26 weeks, in particular about once 52 weeks, after the initial priming at 0, 4, and 8 weeks after initial immunization. Frequency of injection can vary depending on the patient response. For example, the frequency of administration can vary if the injection has to be administered according to antibody titers.

The usefulness of the Aβ peptide immunogen constructs in the treatment of the above-mentioned disorders can be confirmed in suitable clinical studies, e.g., applying a total of three dosages at 0, 4, and 12 weeks with each time applying 300 μg/0.5 mL per dose of vaccine formulation and then followed for over 9 months period, such as those described in the Examples. There can be a follow up immunizations of once every three, six or 12 months according to antibody titers.

Suitable clinical studies are open label studies or in particular randomized, double-blind, placebo-controlled, parallel studies in patients at risk of Alzheimer's Disease or with symptoms of Alzheimer's Disease.

A specific embodiment encompasses vaccine formulation (UBI AD vaccine) which contains a mixture of two Aβ peptide immunogen constructs (SEQ ID NOs: 64 and 65) each with the N-terminus ($A\beta_{1-14}$, SEQ ID NO: 4) of $A\beta_{1-42}$ peptide synthetically linked to T helper (Th) epitopes (SEQ ID NOs: 46 and 47), devoid of the toxic effects observed with autologous Th epitopes in patients receiving the AN-1792 vaccine (aggregated $A\beta_{1-42}$/Elan/Wyeth). In vitro studies and in vivo studies in small animals, baboons and macaques show that antibodies are generated with the expected N-terminus site-specificity, and that these antibodies have functional immunogenicities to neutralize the toxic activity of Aβ and promote plaque clearance. The antibodies appear to draw $A\beta_{1-40}$ from the CNS into peripheral circulation. Results indicate that the vaccine did not evoke anti-$A\beta_{1-42}$ cellular responses. The UBI AD vaccine was well tolerated in cynomolgus macaques during a repeat dose acute and chronic toxicity study. The safety and immunogenicity of UBI AD vaccine formulation embodied in Examples 8 and 9 were further tested in a phase I trial in patients with mild to moderate AD and found to elicit antibodies with specificity to the N-terminus of Aβ$_{1-14}$ peptide in all 19 patients, thus achieving an unprecedented 100% response rate, after intramuscular immunization at 0, 4 and 12 weeks, without causing any serious or intolerable adverse events. A subset of older subjects with mild AD (n=6; age≥60 years with baseline MMSE≥20) showed both high antibody responses to the UBI AD vaccine formulation and improved cognitive and functional outcomes as assessed by (i) ADAS-Cog (AD Assessment Scale—Cognitive); (ii) ADCS-CGIC (Alzheimer's Disease Cooperative Study—Clinical Global Impressions of Change); and (iii) MMSE (Mini-Mental State Exam) scores when compared to baseline scores, during the 6-month core study and after the 6-month observational follow-up period. ADAS-Cog is the most popular cognitive testing instrument used in clinical trials. ADAS-Cog consists of 11 tasks (70-points) that measures the disturbances of memory, language, praxis, attention and other cognitive abilities, which are often referred to as core symptoms of AD (increase in score indicates deterioration). ADCS-CGIC is a single global rating of change from baseline (decrease in score indicates deterioration). MMSE is the most commonly used instrument for screening cognitive function and provides a measure of orientation, registration, short-term memory, language functioning (decrease in score indicates deterioration). In phase IIa trial, biomarkers (molecular diagnostics, brain imaging, genetic typing) are used to evaluate efficacy of the vaccine formulation in patients with mild AD including assessment of decrease in progression of the disease by increasing, through active immunization, anti-Aβ$_{1-14}$ antibodies in circulation, presumably to reduce the concentration of toxic Aβ oligomers in brain.

(g) Specific Embodiments

Specific embodiments of the present invention include, but are not limited to, the following:
(1) An Aβ peptide immunogen construct comprising the following formula:

(N-terminal fragment of Aβ$_{1-42}$peptide)-(A)$o$-(Th)-X wherein (N-terminal fragment of Aβ$_{1-42}$ peptide) is a B cell epitope from Aβ comprising about 10 to about 14 amino acid residues selected from the group consisting of SEQ ID NOs: 4, 5, and 6;
each A is independently an amino acid or a linking group selected from the group consisting of an amino acid, Lys-, Gly-, Lys-Lys-Lys-, (α, ε-N)Lys, and ε-N-Lys-Lys-Lys-Lys (SEQ ID NOs: 32);
each Th comprises an amino acid sequence that constitutes a helper T cell epitope selected from the group consisting of SEQ ID NOs: 34, 37, 38, 40 to 47 and functional immunological analogues thereof;
X is an α-COOH or α-CONH2 of an amino acid; and
o is from 0 to about 4.
(2) The Aβ peptide immunogen construct of (1), wherein the (N-terminal fragment of Aβ$_{1-42}$ peptide) is Aβ$_{1-14}$ (SEQ ID NO: 4).
(3) The Aβ peptide immunogen construct of (1), wherein A is ε-N-Lys-Lys-Lys-Lys (SEQ ID NOs: 32).
(4) The Aβ peptide immunogen construct of (1), wherein the Th epitope is SEQ ID NOs: 45 or 46.
(5) The Aβ peptide immunogen construct of (1), comprising the amino acid sequence of SEQ ID NOs: 48-65.
(6) The Aβ peptide immunogen construct of (1), consisting essentially of the amino acid sequences of SEQ ID NOs: 62-65.
(7) The Aβ peptide immunogen construct of (1) that is SEQ ID NOs: 62, 63, 64, and/or 65.
(8) A composition comprising the Aβ peptide immunogen construct of claim 1.
(9) A pharmaceutical composition comprising
   a. the Aβ peptide immunogen construct of (1); and
   b. a pharmaceutically acceptable delivery vehicle and/or adjuvant.
(10) An Alzheimer's Disease vaccine composition comprising
   a. the Aβ peptide immunogen construct of (1); and
   b. a pharmaceutically acceptable delivery vehicle and/or adjuvant.
(11) An Alzheimer's Disease vaccine composition comprising
   a. the Aβ peptide immunogen construct of (7); and
   b. a pharmaceutically acceptable delivery vehicle and/or adjuvant.
(12) The Alzheimer's Disease vaccine composition of (10), wherein the adjuvant in (b) is a mineral salt of Aluminum selected from the group consisting of ALHYDROGEL® (Al(OH)$_3$) or ADJU-PHOS® (AlPO$_4$).
(13) The Alzheimer's Disease vaccine composition of (10), wherein the peptide antigen in (a) is mixed with an CpG oligodeoxynucleotide (ODN) to form a stabilized immunostimulatory complex.
(14) An isolated antibody or epitope-binding fragment thereof which binds to the (N-terminal fragment of Aβ$_{1-42}$ peptide) component of the Aβ peptide immunogen construct of (1).
(15) The isolated antibody or epitope-binding fragment thereof of (14), which specifically binds to Aβ$_{1-10}$ (SEQ ID NO: 6).
(16) The isolated antibody or epitope-binding fragment thereof of (14), bound to the Aβ peptide immunogen construct of claim 1.
(17) The isolated antibody or epitope-binding fragment thereof of (15), bound SEQ ID NO: 6.
(18) A composition comprising the isolated antibody or epitope-binding fragment thereof of (14).
(19) A method of reducing the severity or delaying onset of dementia in human patients comprising administering a vaccine formulation according to (10).
(20) The method of (19), wherein said vaccine formulation is administered in an aqueous solution comprising between 10 ug and 1000 ug per dose to patients at risk for, or with, AD.

(h) Additional Embodiments (1) An Aβ peptide immunogen construct of this invention is represented by the following formula:

(N-terminal fragment of Aβ$_{1-42}$ peptide)-(A)$_o$-(Th)-X wherein (N-terminal fragment of Aβ$_{1-42}$ peptide) is a B cell epitope selected from the group consisting of SEQ ID NOs: 4 to 6 from about 10 to about 14 amino acid residues;
each A is independently an amino acid or a linking group chosen from the group consisting of an amino acid, Lys-, Gly-, Lys-Lys-Lys-, (α, ε-N)Lys, or ε-N-Lys-Lys-Lys-Lys (SEQ ID NO: 32);
each Th comprises an amino acid sequence that constitutes a helper T cell epitope selected from the group comprising SEQ ID NOs: 34, 37, 38, 40 to 47 and functional immunological analogues thereof;

X is an α-COOH or α-CONH$_2$ of an amino acid; and o is from 0 to about 4.

(2) An Alzheimer's Disease (AD) vaccine composition, comprising
   a. an Aβ peptide immunogen construct according to (1);
   b. a functional immunological analogue of (a);
   c. any combination of (a) or (b); and
   d. an acceptable delivery vehicle or adjuvant.

(3) The AD vaccine according to (2), wherein the adjuvant in (d) is a mineral salt of Aluminum being ALHYDROGEL® (Al(OH)$_3$) or ADJU-PHOS® (AlPO$_4$).

(4) The AD vaccine according to (2), wherein the peptide antigen in (a) is mixed with an CpG oligodeoxynucleotide (ODN) to form a stabilized immunostimulatory complex.

(5) An Alzheimer's Disease (AD) vaccine composition, comprising
   a. an Aβ peptide immunogen construct selected from the group comprising SEQ ID NOs: 49-51, 54, 55, and 57-65;
   b. a functional immunological analogue of (a);
   c. any combination of (a) or (b); and
   d. an acceptable delivery vehicle or adjuvant.

(6) An Alzheimer's Disease (AD) vaccine composition, comprising
   a. an Aβ peptide immunogen construct according to (5);
   b. a functional immunological analogue of (a);
   c. any combination of (a) or (b); and
   d. an acceptable delivery vehicle or adjuvant.

(7) The AD vaccine according to (5), wherein the adjuvant in (d) is a mineral salt of Aluminum being ALHYDROGEL® (Al(OH)$_3$) or ADJU-PHOS® (AlPO$_4$).

(8) The AD vaccine according to (5), wherein the peptide antigen in (a), (b), or (c) is mixed with an CpG oligodeoxynucleotide (ODN) to form a stabilized immunostimulatory complex.

(9) The AD vaccine according to (5), wherein the peptide antigen in (a), (b), or (c) is mixed with an CpG oligodeoxynucleotide (ODN) to form a stabilized immunostimulatory complex and, wherein the adjuvant in (d) is a mineral salt of Aluminum that is ALHYDROGEL® (Al(OH)$_3$) or ADJU-PHOS® (AlPO$_4$).

(10) An Alzheimer's Disease (AD) vaccine composition, comprising
   a. an Aβ peptide immunogen construct selected from the group comprising SEQ ID NOs: 62+63, 64+65;
   b. a functional immunological analogue of (a);
   c. any combination of (a) or (b); and
   d. an acceptable delivery vehicle or adjuvant.

(11) A composition comprising:
   a. an Aβ peptide immunogen construct comprising a mixture of SEQ ID NO: 64 and SEQ ID NO: 65; and
   b. the mixture of (a) further mixed with CpG ODN.

(12) A pharmaceutical composition comprising:
   a. an Aβ peptide immunogen construct comprising a mixture of SEQ ID NO: 64 and SEQ ID NO: 65;
   b. the mixture of (a) further mixed with CpG ODN; and
   c. ADJU-PHOS®.

(13) A pharmaceutical composition comprising:
   a. an Aβ peptide immunogen construct comprising a mixture of SEQ ID NO: 64 and SEQ ID NO: 65;
   b. the mixture of (a) further mixed with CpG ODN; and
   c. ALHYDROGEL®.

(14) A method of reducing the severity or delaying onset of dementia in humans comprising administering the pharmaceutical composition of (13) to the human.

(15) A method of reducing the severity or delaying onset of dementia in humans comprising administering the pharmaceutical composition of (13) to the human at a dose of 300 μg/0.5 mL/dose.

(16) A method of reducing the severity or delaying onset of dementia in humans comprising:
   a. administering the pharmaceutical composition of (13) to the human at a dose of 300 μg/0.5 mL/dose; and
   b. dosing at 0, 4, and 12 weeks as prime.

(17) A method of reducing the severity or delaying onset of dementia in humans comprising:
   a. administering the pharmaceutical composition of (13) to the human at a dose of 300 μg/0.5 mL/dose;
   b. dosing at 0, 4, and 12 weeks as prime; and
   c. boosting after the step in (b) at once every 3 months, and/or once every 6 months, and/or once every 12 months.

(18) The method of any of (14)-(17) wherein the administration is by intramuscular injection.

(19) The method of any of (14)-(18) wherein the human has mild AD, MCI, or does not display signs or symptoms of AD but is over the age of 60.

(20) The method of (19) wherein administration to the human is as follows:
   a. if the human has mild AD, administration is for the treatment of AD;
   b. if the human has MCI, administration is for the prevention and/or reduction of the severity of and/or the delay in the onset of dementia; and
   c. if the human does not display signs or symptoms of AD but is over the age of 60, administration is for the prevention and/or reduction of the severity of and/or the delay in the onset of dementia.

(21) The AD vaccine according any of (2)-(10), wherein the peptide antigen in (a) is mixed with an oligonucleotide CpG to form a stabilized immunostimulatory complex.

(22) The AD vaccine according to the above, wherein the Aβ peptide immunogen construct in (a) comprises the amino acid sequence of SEQ ID NOs: 17 to 20.

(23) The AD vaccine according to the above, wherein the Aβ peptide immunogen construct in (a) comprises the amino acid sequence of SEQ ID NOs: 19 and 20.

(24) The AD vaccine according to the above, wherein the total amount of peptide antigen in (a) is between about 10 μg to about 1 mg per dose.

(25) The AD vaccine according to the above, wherein the delivery vehicle or adjuvant is selected from the group consisting of Montanide ISA 50V, Polyoxyethylene (20) sorbitan monooleate, Emulsigen, Emulsigen D, and a CpG oligonucleotide.

(26) A method of reducing the severity or delaying onset of dementia in human patients comprising administering a vaccine formulation according to any of the above.

(27) The method according to any of the above wherein the dementia is dementia of the Alzheimer's type or vascular dementia with amyloid angiopathy.

(28) The method according to any of the above wherein the dementia is dementia associated with Parkinson's disease or Lewy Body dementia.

(29) The method according to any of the above, wherein said vaccine formulation is administered in an aqueous solution comprising between 10 μg and 1000 μg per dose to patients at risk for, or with, AD. Also acceptable is 100 to 750 μg per dose or 300 μg per dose. 300 μg can be the target dose used in clinical trial with efficacy.

(30) Administration can be once every 3 months and/or once every 6 months and/or once every 12 months.

(31) Administration can be based on antibody titer to decide the frequency of vaccine administration.
(32) The method according to any of the above, wherein the patients are at risk of developing Alzheimer's disease and further wherein the patients are selected from the group consisting of patients with mild cognitive impairment, patients with genotypes known to be associated with Alzheimer's Disease, patients with Trisomy 21 and patients with surrogate markers indicating risk for Alzheimer's Disease.
(33) The method according to any of the above, wherein the patients with genotypes known to be associated with Alzheimer's Disease comprise patients with the ApoE4 genotype.
(34) The method according to any of the above, wherein the vaccine formulation comprising Aβ peptide immunogen construct in (a) and combination thereof is administered for the initial priming of three doses at 0, 4 and 12 weeks at 300 µg/0.5 mL per dose.
(35) The method according to any of the above, wherein the vaccine formulation is administered about once every three months, then once every 6 months and then once every 12 months.
(36) The method according to any of the above, wherein the B cells from the blood of patients previously receiving the vaccine formulation are used for preparation and selection of human monoclonal antibodies targeting N-terminus of Aβ peptide for the prevention and treatment of AD.
(37) A method for eliciting an immune response in an subject comprising providing a priming immunization at 0, 4 and 12 weeks from initial injection followed by boost immunization at once 3 month, once 6 month, and most preferably once every 12 month.
(38) Dosing can be performed at 10 µg to 1000 µg per dose, preferably 100 µg to 750 µg, even more preferably 300 µg per dose.
(39) Route for administration of any of the above can be by any standard route known in the art, such as intramuscular route, subcutaneous, oral, etc.

A pharmaceutical composition that is useful as an Aβ peptide immunogen construct vaccine formulation, contains an Aβ peptide immunogen construct and an acceptable delivery vehicle or adjuvant, wherein the Aβ peptide immunogen construct has an amino acid sequence selected from the group consisting of:
a) SEQ ID NOs: 49-51, 54, 55, and 57 to 65;
b) a homologue of (a);
c) an antigenically and immunologically functional analogue of (a) or (b),
d) (a), (b), or (c) having at least one conservative amino acid substitution, amino acid addition, and/or amino acid deletion; and
e) any combination of (a)-(d).

In a specific formulation, the Aβ peptide immunogen construct is selected from the group consisting of SEQ ID NOs: 62 and 63 and mixtures thereof.

In another specific formulation, the Aβ peptide immunogen construct is selected from the group consisting of SEQ ID NOs: 64 and 65 and mixtures thereof.

Other formulations further contain an equimolar mixture of a specific formulation, the Aβ peptide immunogen construct is selected from the group consisting of SEQ ID NOs: 62 and 63. Other formulations further contain an equimolar mixture of a specific formulation, the Aβ peptide immunogen construct is selected from the group consisting of SEQ ID NOs: 64 and 65.

In a specific formulation, the amount of the equimolar mixture of SEQ ID NOs: 62 and 63 (or 64 and 65) is between about 1 µg to about 1000 µg per dose.

In a specific formulation, the amount of the equimolar mixture of SEQ ID NOs: 62 and 63 (or 64 and 65) is between about 100 µg to about 750 µg per dose.

In a specific formulation, the amount of the equimolar mixture of SEQ ID NOs: 62 and 63 (or 64 and 65) is between about 300 µg per dose.

The efficacy of the peptide composition of the present invention can be established by injecting an animal, for example, guinea pigs, baboons, Cynomolgus macaques, or humans with an immunogenic composition comprising peptides of the invention. See, Tables 4, 5, 6, 7 and 8 SEQ ID NOs: 48 to 65. The humoral immune response is directed to the N-terminal fragment of $A\beta_{1-42}$ peptide from about 10 to about 14 amino acid residues. A detailed description of the procedures used is provided in the Examples.

The following examples serve to illustrate the present invention and are not to be used to limit the scope of the invention.

Example 1

Synthesis of Amyloid Beta (Aβ) Related Peptides

Methods for synthesizing designer Aβ related peptide constructs that were included in the development effort for an efficacious targeting Aβ vaccine design and formulation are described. The peptides can be synthesized in small-scale amounts, which are useful for laboratory pilot and field studies, as well as large-scale (kilogram) amounts, which are useful for industrial commercial production of vaccine formulations and serological assays.

A large repertoire of Aβ related antigenic peptides having sequences with lengths from approximately 10 to 40 amino acids were designed for the screening and selection of the most optimal peptide constructs for use in an efficacious AD vaccine. Representative $A\beta_{1-40}$, $A\beta_{1-42}$ peptides, N-terminus Aβ peptide fragments $A\beta_{1-28}$, $A\beta_{1-14}$, $A\beta_{1-10}$, $A\beta_{15-42}$ and 10-mer peptide employed for epitope mapping in various serological assays are identified in Table 1 (SEQ ID NOs: 1 to 32). Each construct contains an Aβ peptide fragment ($A\beta_{1-10}$ to $A\beta_{1-14}$) synthetically links to a carefully designed helper T cell (Th) epitope derived from pathogen proteins including Measles Virus Fusion protein (MVF) and Hepatitis B Surface Antigen protein (HBsAg), identified in Table 2 (SEQ ID NOs: 33 to 47) either in a single sequence (SEQ ID NOs: 33 to 41, 46, 47) or a combinatorial library (SEQ ID NOs: 42 to 45) to enhance the immunogenicity of their respective Aβ peptide immunogen constructs. Eighteen representative Aβ peptide immunogen constructs selected from over 100 peptide constructs are identified in Table 3 (SEQ ID NOs: 48 to 65).

All peptides used for immunogenicity studies or related serological tests for detection and/or measurement of anti-Aβ antibodies were synthesized on a small scale using Fmoc chemistry by peptide synthesizers of Applied BioSystems Models 430A, 431 and/or 433. Each peptide was produced by an independent synthesis on a solid-phase support, with Fmoc protection at the N-terminus and side chain protecting groups of trifunctional amino acids. Completed peptides were cleaved from the solid support and side chain protecting groups were removed by 90% Trifluoroacetic acid (TFA). Synthetic peptide preparations were evaluated by Matrix-Assisted Laser Desorption/Ionization-Time-Of-Flight (MALDI-TOF) Mass Spectrometry to ensure correct amino acid content. Each synthetic peptide was also evaluated by Reverse Phase HPLC (RP-HPLC) to confirm the synthesis profile and concentration of the preparation.

Despite rigorous control of the synthesis process (including stepwise monitoring the coupling efficiency), peptide analogues were also produced due to unintended events during elongation cycles, including amino acid insertion, deletion, substitution, and premature termination. Thus, synthesized preparations typically included multiple peptide analogues along with the targeted peptide. Despite the inclusion of such unintended peptide analogues, the resulting synthesized peptide preparations were nevertheless suitable for use in immunological applications including immunodiagnosis (as antibody capture antigens) and vaccination (as peptide immunogens). Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process to guarantee the reproducibility and efficacy of the final product employing these peptides. Large scale peptide syntheses in the multi-hundred to kilo gram quantities were conducted on a customized automated peptide synthesizer UBI2003 at 15 mmole to 50 mmole scale.

For active ingredients used in the final vaccine formulation for clinical trials, Aβ peptide constructs were purified by preparative RP-HPLC under a shallow elution gradient and characterized by MALDI-TOF mass spectrometry, amino acid analysis and RP-HPLC for purity and identity.

Example 2

Serological Assays and Reagents

Serological assays and reagents for evaluating functional immunogenicity of the synthetic peptide constructs and formulations thereof are described in details below.

a. $A\beta_{1-42}$, $A\beta_{1-40}$, $A\beta_{1-28}$, or $A\beta_{1-14}$ Peptide-Based ELISA Tests for Antibody Specificity Analysis ELISA assays for evaluating immune serum samples described in the following Examples were developed and described below.

The wells of 96-well plates were coated individually for 1 hour at 37° C. with 100 μL of target peptide $A\beta_{1-42}$, $A\beta_{1-40}$, $A\beta_{1-28}$, or $A\beta_{1-14}$ (SEQ ID NOs: 1 to 4), at 2 μg/mL (unless noted otherwise), in 10 mM $NaHCO_3$ buffer, pH 9.5 (unless noted otherwise).

The peptide-coated wells were incubated with 250 μL of 3% by weight of gelatin in PBS in 37° C. for 1 hour to block non-specific protein binding sites, followed by three washes with PBS containing 0.05% by volume of TWEEN® 20 and dried. Sera to be analyzed were diluted 1:20 (unless noted otherwise) with PBS containing 20% by volume normal goat serum, 1% by weight gelatin and 0.05% by volume TWEEN® 20. One hundred microliters (100 μL) of the diluted specimens (e.g., serum, plasma) were added to each of the wells and allowed to react for 60 minutes at 37° C.

The wells were then washed six times with 0.05% by volume TWEEN® 20 in PBS in order to remove unbound antibodies. Horseradish peroxidase (HRP)-conjugated species (e.g., mouse, guinea pig, or human) specific goat anti-IgG, was used as a labeled tracer to bind with the antibody/peptide antigen complex formed in positive wells. One hundred microliters of the peroxidase-labeled goat anti-IgG, at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 μL of the substrate mixture containing 0.04% by weight 3',3',5',5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 μL of 1.0M $H_2SO_4$ and absorbance at 450 nm ($A_{450}$) determined. For baboon and macaque Ig/IgG detection, HRP-conjugated goat anti-human IgG reagents with high cross-reactivity to the primate IgG was used as the tracer. For clinical samples from patients entering the trials, HRP-conjugated Protein A/G reagents, optimally titered in previously validated ELISA test kits, were used for serum titer determination. For the determination of antibody titers of the vaccinated animals that received the various Aβ peptide vaccine formulations, 10-fold serial dilutions of sera from 1:100 to 1:10,000 were tested, and the titer of a tested serum, expressed as $Log_{10}$, was calculated by linear regression analysis of the $A_{450}$ with the cutoff $A_{450}$ set at 0.5 b. Assessment of Antibody Reactivity Towards the Helper T Cell Epitopes on the Carrier Protein, Th Peptide or Th Combinatorial Peptide Library by Specific Carrier Protein, Th Peptide or Th Combinatorial Library Based ELISA Tests The wells of 96-well ELISA plates were coated individually for 1 hour at 37° C. with 100 μL of carrier protein such as KLH (Keyhole limpet hemocyanin), Th peptide or Th combinatorial peptide library (SEQ ID NOs: 44 to 47), at 2 μg/mL (unless noted otherwise), in 10 mM $NaHCO_3$ buffer, pH 9.5 (unless noted otherwise) in similar ELISAs and performed as described above. For the determination of antibody titers of the vaccinated animals that received the various Aβ peptide vaccine formulations, 10-fold serial dilutions of sera from 1:100 to 1:10,000 were tested, and the titer of a tested serum, expressed as $Log_{10}$, was calculated by linear regression analysis of the $A_{450}$ with the cutoff $A_{450}$ set at 0.5.

c. Assessment of Fine Specificity Analysis and Epitope Mapping Towards Aβ and hAPP (Human Amyloid Precursor Protein) by B Cell Epitope Cluster 10-Mer Peptide-Based ELISA Tests Fine specificity analyses of anti-Aβ antibodies in immunized hosts or vaccines were determined by epitope mapping. Briefly, the wells of 96-well plates were coated with individual hAPP 10-mer peptides (SEQ ID NOs: 6, 8 to 30) at 0.5 μg per 0.1 mL per well and then 100 μL serum samples (1:100 dilution in PBS) were incubated in 10-mer plate wells in duplicate following the steps of the antibody ELISA method described above. The B cell epitope of the vaccine and related fine specificity analyses of baboon, macaque and human anti-Aβ antibodies in immunized hosts were also pre-absorbed with $A\beta_{1-10}$ peptide (DAEFRHDSGY, SEQ ID NO: 6), Aβ-modified synthetic peptides with substitutions at the N-terminus, or with non-relevant control peptide and then tested by anti-$A\beta_{1-28}$ ELISA test for additional specificity confirmation.

d. Immunogenicity Evaluation

Preimmune and immune serum samples from human subjects or animals were collected according to experimental vaccination protocols and heated at 56° C. for 30 minutes to inactivate serum complement factors. Following the administration of the vaccine formulations, blood samples were obtained according to protocols and their immunogenicity against specific target site(s) evaluated. Serially diluted sera were tested and positive titers were expressed as $Log_{10}$ of the reciprocal dilution Immunogenicity of a particular vaccine formulation is assessed by its ability to elicit high titer B cell antibody response directed against the desired epitope specificity within the target antigen while maintaining a low to negligible antibody reactivity towards the "Helper T cell epitopes" employed to provide enhancement of the desired B cell responses.

e. Solid-Phase Enzyme-Linked Immunoassay for Detection of AB Related Peptide Antigens in Blood and Cerebral Spinal Fluid (CSF)

A high sensitivity $A\beta_{1-40}$ immunoassay (Invitrogen™—BioSource™ Cytokines & Signaling, Camarillo, Calif., USA) was used to determine the concentration of $A\beta_{1-40}$ in serum, plasma and CSF in Cynomolgus macaques following kit instructions. The $A\beta_{1-42}$ levels were below detection limits in normal macaques. $A\beta_{1-40}$ and $A\beta_{1-42}$ levels in plasma, CSF and chemical extractions of brain tissue from hAPP751 transgenic mice were determined following instructions of $A\beta_{1-40}$ and $A\beta_{1-42}$ immunoassay (The Genetics Company Inc., Zurich-Schlieren, Switzerland). Quantification of $A\beta_{1-40}$ levels in plasma of individuals with mild to moderate Alzheimer's disease was determined following kit instructions (Human Amyloid β (1-40) Assay Kit, IBL, 27714). The $A\beta_{1-42}$ levels in human plasma were below detection limits.

Example 3

Immunohistochemical Analysis

Normal adult human tissues (PhenoPath Laboratories Inc., Seattle, Wash., USA) and brain specimens from cases with Alzheimer's disease (Dr. Felicia Gaskin, University of Virginia, Charlottesville, Va., USA) were obtained from post-mortem and/or surgical pathology specimens. Cynomolgus macaque tissue specimens (Beijing Jo-Inn New Drug Research Center, Beijing, China) and hAPP transgenic mouse brain specimens (JSW-Research GmbH, Graz, Austria) were obtained at necropsy. Tissues were either snap-frozen in liquid nitrogen, submerged in cold OCT embedding compound and cryo-sectioned or they were formalin-fixed, paraffin-embedded and sections prepared by standard procedures.

Indirect immunofluorescence analysis of cryopreserved tissue sections were performed with preimmune and hyperimmune serum or purified IgG from guinea pigs, hAPP transgenic mice, baboons and macaques or with commercially available murine monoclonal antibodies and fluorochrome-conjugated secondary antibodies. Indirect immunoperoxidase staining using an avidin-biotin enhanced commercially available kit was performed on cryopreserved tissue sections of normal adult tissues using purified guinea pig anti-Aβ IgG, or on brain sections from control and UBI AD vaccine (UB-311) treated macaques using commercially available monoclonal antibodies detecting CD3, CD4, CD8 (T lymphocyte subsets), CD11b (microglial cell activation marker), GFAP (astrocytes) and specific Aβ epitopes. The immunohistochemical analyses were conducted according to standard pathology laboratory procedures.

Example 4

T Cell Functional Assays for Lymphocyte Proliferation and Cytokine Production

The procedures for T cell functional assays including lymphocyte proliferation and cytokine production for assessment of T cell activation are described in detail as follows.

a. Isolation, Freezing, and Defrosting of Peripheral Blood Mononuclear Cells (PBMC)

Heparinized blood was collected, and PBMC were isolated by Ficoll-Hypaque density gradient centrifugation. After two washes in phosphate-buffered saline (PBS), PBMC were resuspended in cell culture medium consisting of RPMI 1640 supplemented with 10% fetal calf serum (FCS). For some experiments, isolated PBMC were frozen, stored in liquid $N_2$, and defrosted for subsequent in vitro cultivation.

b. T Cell and Peripheral Blood Mononuclear Cell (PBMC) Proliferation Assay

PBMC from vaccinated animals were cultured at $2.5 \times 10^6$ cells/mL in individual wells of a 24-well culture plate (Nunc) in the presence of 10.0 μg of the selected vaccine immunogen composition. Negative control cultures containing PBMC alone without stimulating antigen were also included. All cultures were kept at 37° C. for 3 days in a 5.0% $CO_2$ incubator. Supernatants were collected 3 days after culture initiation, and individual cytokines were measured using the quantitative assay described above.

Peripheral blood mononuclear cells (PBMC) from baboons and from Cynomolgus macaques were isolated by Ficoll-hypaque gradient centrifugation. For peptide-induced proliferation and cytokine production, cells ($2 \times 10^5$ cells per well) were cultured alone or with individual peptide domains added (including, $A\beta_{1-42}$, $A\beta_{1-14}$, $A\beta_{15-42}$, Th peptides, and non-relevant peptide as a negative control). Mitogens (PHA, PWM, ConA) were used as positive controls. On day 6, 1 μCi of $^3$H-thymidine ($^3$H-TdR) was added to each of three replicate cell culture wells. After 18 hours of incubation, cells were harvested and $^3$H-TdR incorporation was determined. The stimulation index (S.I.) represents the counts per minute (cpm) in the presence of antigen divided by the cpm in the absence of antigen; a S.I.>3.0 was considered significant.

c. Evaluation of Cytokines Produced by PBMC Cultures Pre- and Post-Immunization with UBI AD Vaccine Cytokine analyses (IL-2, IL-6, IL-10, IL-13, TNF-α, IFN-γ) from Cynomolgus macaque PMBC cultures were performed on aliquots of culture medium alone or in the presence of various Aβ peptide domains or mitogens. Monkey-specific cytokine sandwich ELISA test kits (U-CyTech Biosciences, Utrecht, The Netherlands) were used to determine the concentration of individual cytokines following kit instructions.

Example 5

Animals Used in Safety, Immunogenicity, Toxicity and Efficacy Studies

Guinea Pigs:
Immunogenicity studies were conducted in mature, naïve, adult male and female Duncan-Hartley guinea pigs (300-350 g/BW). The experiments utilized at least 3 Guinea pigs per group. Protocols involving Duncan-Hartley guinea pigs (8-12 weeks of age; Covance Research Laboratories, Denver, Pa., USA), were performed under approved IACUC applications at the contracted animal facility as well as at UBI, as sponsor.

*Anubis* Baboons:
Immunogenicity studies in adult male baboons (*Papio anubis*, 8 to 10 years of age; University of Oklahoma Health Sciences Center, Oklahoma City, Okla., USA) were conducted under approved IACUC applications at the contracted animal facility as well as at UBI, as sponsor.

Cynomolgus Macaques:
Immunogenicity and repeated dose toxicity studies in adult male and female monkeys (*Macaca fascicularis*, approximately 4 years of age; Beijing Jo-Inn New Drug Research Center, Beijing, China) were conducted under approved IACUC applications at the contracted animal facility as well as at UBI, as sponsor.

hAPP751 Transgenic Mice:
Immunogenicity and efficacy studies in young hAPP751 transgenic (tg+) mice and their littermates (14±2 weeks of age) were used in a prevention model for Alzheimer's disease and aged tg+ mice and their littermates (52+2 weeks of age) were used in a therapeutic model. Both studies were performed under approved IACUC applications at the contracted animal facility (JSW Research GmbH, Graz, Austria) as well as at UBI, as sponsor.

The hAPP751 tg+ mice constitutively overexpress human amyloid precursor protein (hAPP) containing the London (V717I) and Swedish (K670M/N671L) double mutations, under the regulatory control of the murine Thy-1 promoter (Rockenstein, E, et al., 1995 and 2001). The $A\beta_{1-42}$ deposition occurs as early as 3 to 4 months of age with the appearance of mature plaques in the frontal cortex and at 5 to 7 months of age, plaque formation extends to the hippocampus, thalamus and olfactory region in the hAPP751 tg+ mice. The effects of intramuscular vaccinations over a 16 week period were observed for antibody response by ELISA assay of serum, and for brain amyloid deposition and brain plaque load, as well as for evidence of increased levels of cellular reactivity (e.g., T cell infiltration, microglial cell activation) in the brain by immunostaining and by biochemical extractions.

Prior to immunization, serum and/or plasma samples from individual animals were tested for the presence of Aβ target peptides according to methods described above in this Example. Each animal was immunized with Aβ target peptide constructs per dose of the vaccine formulations, depending on species and protocol.

Example 6

General Vaccine Formulation for Initial Ranking of the Immunogenicity of Aβ Peptide Constructs in Guinea Pigs and Baboons Pharmaceutical compositions and vaccine formulations used in each experiment are described in greater detail in the Examples described below. Briefly, the formulations specified in each of the study groups generally contained all types of designer Aβ peptide constructs with a fragment of the Aβ peptide linked via different type of spacers (e.g., εK or εK with KKK to enhance the peptide construct's solubility) and variations of promiscuous helper T cell epitopes including two sets of artificial T helper epitopes derived from Measles virus fusion protein and Hepatitis B surface antigen with the Aβ peptide fragment(s) linked at the N-terminus of the designer peptide constructs. Over 100 designer Aβ peptide constructs were initially evaluated in guinea pigs for their relative immunogenicity with the full length $A\beta_{1-42}$ and further their cross-reactivity with the native plaques from the brain sections of AD patients. The Aβ peptide constructs were prepared in a water-in-oil emulsion with Seppic Montanide™ ISA 51 (containing mineral oil with mannide oleate) (Seppic, Puteaux, France) as the approved oil for human vaccine use, mixed with mineral salts or ALHYDROGEL® (Alum) at varying amounts of peptide constructs as specified. Vaccines were usually prepared by dissolving the Aβ peptide constructs in water at about 20 to 800 μg/mL and formulated with Montanide™ ISA 51 into water-in-oil emulsions (1:1 in volume) or with mineral salts or ALHYDROGEL® (Alum) (1:1 in volume). The vaccine formulations were kept at room temperature for about 30 minutes and mixed by vortex for about 10 to 15 seconds prior to immunization.

Some animals were immunized with 2 to 3 doses of a specific vaccine formulation, which were administered at time 0 (prime) and 3 week post initial immunization (wpi) (booster), optionally 5 or 6 wpi for a second boost, by intramuscular route. These immunized animals were then tested to evaluate the immunogenicity of the various synthetic Aβ peptide immunogens present in the vaccine formulation as well as their cross-reactivity with $A\beta_{1-28}$ and the full length $A\beta_{1-42}$. Those Aβ peptide immunogens with potent immunogenicity in the initial screening in guinea pigs were then further tested in both water-in-oil emulsion, mineral salts, and alum-based formulations in baboons, which species has been calibrated as having similar immune response profile as that of humans, for dosing regimens over a specified period as dictated by the immunizations protocols.

Only the most promising Aβ peptide immunogen candidates were further assessed extensively prior to being incorporated into final vaccine formulations for immunogenicity, duration, toxicity and efficacy studies in GLP guided preclinical studies in preparation for submission of an Investigational New Drug application and clinical trials in patients with Alzheimer's disease.

Example 7

Design Rationale, Screening, Identification and Optimization of Multi-Component Vaccine Formulations Incorporating $A\beta_{1-14}$ Peptide Immunogen Constructs for Prevention and Treatment of Dementia of Alzheimer's Type Design History:

Each vaccine or immunotherapeutic product requires its own design focus and approach based on the specific disease mechanism and the target protein(s) required for intervention. The targets that designs are modeled after can include cellular proteins involved in a disease pathway or an infectious agent in which several proteins from the pathogen may be involved. The process from research to commercialization is a very long process typically requires one or more decades to accomplish.

An extensive process of serological validation is required once the target molecule is selected. Identification and distribution of the B cell and T cell epitopes within the target molecule is important to the molecular vaccine design. Once the target B cell is recognized, consecutive pilot immunogenicity studies in small animals are conducted to evaluate the functional properties of the antibodies elicited by the vaccine formulations of the designer peptides. Such serological application is then carried out in animals of the target species for further validation of the vaccine immunogenicity and functional properties of the elicited antibodies. All studies are conducted in multiple parallel groups with sera collected from the immunized hosts for evaluation. Early immunogenicity studies in the target species or in non-human primate in the case of human vaccines, are also carried out to further validate the immunogenicity and direction of the design. Target peptides are then prepared in varying mixtures to evaluate subtle difference in functional property related to the respective interactions among peptide constructs when used in combinations to prepare for respective formulation designs. After additional evaluations, the final peptide constructs, peptide compositions and formulations thereof, along with the respective physical parameters of the formulations are established leading to the final product development process.

Extensive design experience allows for the development of the next generation vaccine products from discovery to commercialization as shown in FIG. 1 at an accelerated pace.

a. Design and Validation of Suitable $A\beta_{1-14}$ Derived Peptide Constructs for Vaccine Formulations with Potential to Treat Patients with Alzheimer's Disease As a follow up to the previous invention disclosed by this inventor (Wang C Y. U.S. Pat. No. 6,906,169, United States: United Biomedical Inc.; 2005; Wang CY. U.S. Pat. No. 7,951,909, United States: United Biomedical Inc.; 2011; Wang CY. U.S. Pat. No. 8,232,373, United States: United Biomedical Inc.; 2012).), further refinement of the B cell epitope from the Aβ molecule settled on a $A\beta_{1-14}$ peptide devoid of the C-terminal domain of the sequence which express autologous T helper epitopes frequently present in patients of Alzheimer's disease that could cause severe side effect, such as meningoencephalitis, was selected as the target B cell epitope in the design for incorporation into the vaccine formulations.

In order to generate the most potent peptide constructs for incorporation into the vaccine formulations, a large repertoire of promiscuous T helper epitopes derived from various pathogens or artificially T helper epitopes further designed from Measles Virus Fusion (MVF) protein sequence or Hepatitis B Surface Antigen (HBsAg) protein were made into immunogenicity studies in guinea pigs. A representative study of 16 $A\beta_{1-14}$ derived peptide constructs as shown in Table 3 (SEQ ID NOs: 48, 51 to 65) where $A\beta_{1-14}$ peptide was linked through εK as spacer with individual promiscuous T helper epitopes. The peptide immunogen constructs were formulated into Montanide™ ISA 51 water-in-oil emulsions and tested in guinea pigs for their respective immunogenicity by administering the respective vaccine formulations prepared at 100 μg/0.5 mL in a standard ISA 51 emulsion for a prime at 0 wpi and a boost at 3 wpi. Preliminary immunogenicity analysis confirmed the presence of a helper T cell epitope structure feature in the C-terminus of $A\beta_{1-42}$ where deletion of peptide sequence from amino acids 15 to 28 of the Aβ sequence rendered $A\beta_{1-14}$ sequence non-immunogenic on its own (Table 4, Groups 1 to 3). Preliminary ranking of the T helper epitopes used to restore and enhance the immunogenicity of the $A\beta_{1-14}$ peptide's immunogenicity in increasing order is shown in Table 4 with the weakest peptide construct listed first: *Schistosoma mansoni* Th (SEQ ID NO: 56)<*Clostridium tetani*1 Th (SEQ ID NO: 48)<*Bordetella pertussis* Th (SEQ ID NO: 52)<*Clostridium tetani*2 Th (SEQ ID NO: 53)<Diphtheria Th (SEQ ID NO: 54)<*Plasmodium falciparum* Th (SEQ ID NO: 55) with Cholera toxin Th (SEQ ID NO: 57) being ranked amongst those artificial T helper epitope derived from MVF (SEQ ID NOs: 51, 58, 59) and HBsAg (SEQ ID NO: 60). The $A\beta_{1-14}$ derived peptide construct (SEQ ID NO: 51) can also be designed as a branched tetrameric structure as shown in (SEQ ID NO: 61) as a potent peptide immunogen construct. In summary, the above immunogenicity study validated the suitability of specific $A\beta_{1-14}$ derived constructs (SEQ ID NOs: 51, 57 to 61) as immunogen for use in the design of the final vaccine formulation for eliciting antibodies directed at the N-terminus of the full length $A\beta_{1-42}$ peptide, a major biochemical component of the senile plaques of patients with AD.

b. Broadening of MHC Coverage by Using $A\beta_{1-14}$ Derived Constructs with Different Promiscuous T Helper Epitopes When designing a vaccine to treat patients of diverse genetic background, it is important to allow the design to cover maximal population with diverse genetic background. It was therefore explored for synergistic immunogenicity effect of $A\beta_{1-14}$ derived peptide immunogen constructs for such a combination. Since promiscuous T helper epitopes derived from MVF and HBsAg represent amongst the most potent ones to provide such immunogenicity enhancement, combination of peptide constructs containing these two helper T epitopes were therefore designed for such exploration. Combinatorial library forms of T helper epitopes for both MVF and HBsAg (SEQ ID NOs: 44 and 45) were designed as shown in Table 2, with maximal MHC binding motif coverage in mind, into $A\beta_{1-14}$ derived constructs (SEQ ID NOs: 62 and 63) and they, individually or in combination, were evaluated for immunogenicity in guinea pigs following a prime (0 wpi) and two boosts (3 and 5 wpi) schedule at a 100 μg/0.5 mL per dose. As shown in Table 5, a mixture of the two immunogens at equal ratio by weight, did elicit a respectable immune response when compared to that elicited by the respective individual peptide construct.

c. Simple Immunogen Design Incorporating Target B Epitope Linked to Carefully Selected T Helper Epitopes with Multiple MHC Binding Motifs Generate a Focused and Clean Immune Response Targeted Only to the B Cell Epitope Hyperimmune sera 8 weeks post initial immunization (wpi) were collected from the immunized hosts for testing with the respective T helper epitopes used for B epitope immunogenicity enhancement. Hyperimmune sera from similar immunized hosts which were given a similar prime and boost immunization schedule of a KLH-linked $A\beta_{1-14}$ peptide which was prepared through chemical coupling with an added Cysteine residue at the N-terminus of the $A\beta_{1-14}$ peptide. As can be seen from Table 6, all hosts immunized with the designer $A\beta_{1-14}$ peptide immunogen constructs (SEQ ID NOs: 62 and 63) either alone or in combination generated the desired high titers of anti-$A\beta_{1-14}$ antibody crossreactivity towards the targeted $A\beta_{1-42}$ crossreactivity while little or no reactivity was generated against the two T helper epitopes (SEQ ID NOs: 44 and 45). In contrast, despite the relative immunogenicity generated by the conventional carrier protein KLH to the $A\beta_{1-14}$ epitope ($Log_{10}$) titers from 2.2 to 3.9), a very high antibody response directed at the protein carrier KLH was generated by all animals with very high titers (GeoMean of the $Log_{10}$ titer at 6.2), again validated prior observation in that a unique "focused" response directed at the "Targeted B cell epitope" was the outcome of immunization with these rationally designed peptide immunogen constructs based on understanding of the structure and function of the B cell and T cell epitopes.

d. Assessment of Immunogenicity in Baboons after Prime (0 Wpi) and Boosts (3 and 6 Wpi) of Vaccine Formulations Containing Varying Amounts of $A\beta_{1-14}$ Constructs (SEQ ID NOs: 62 and 63) in ISA 51 Water-in-Oil Emulsion and in Alum Prior to moving into further development work to explore the functional properties of the antibodies elicited by these $A\beta_{1-14}$ peptide immunogen constructs, an assessment of the relative immunogenicity of vaccine formulations incorporating these peptide constructs (SEQ ID NOs: 62 and 63 at an equimolar ratio) at varying amounts in two different formulations most frequently used in human testing were assessed in baboons, the animal species which generates immune responses most resemble that of humans in scale. All vaccine formulations were given to the animals in 0.5 mL per dose. The original targeted dose for future use was at 100 μg/mL thus three animals were given at this dose. An assessment for the relative immunogenicity between the more potent ISA 51 water-in-oil formulation versus the weaker yet most frequently used adjuvant Alum at the same 100 μg was also assessed. In the water-in-oil emulsion system tested, a dosing escalation study with 25 μg, 100 μg and 400 μg per dose was assessed. The first observation from this study was the lowered immune responses (by more than one $Log_{10}$ in antibody titers) generated by the Alum-based formulation when compared to the ISA water-in-oil emulsion formulation with same peptide immunogen content given at 100 μg in 0.5 mL per dose. Although 100 μg per dose was the originally targeted amount for future vaccine formulation administration in immunized hosts, an increase of the immune response was observed with an increase of dosing from 25 μg, to 100 μg to 400 μg respectively as shown in Table 7. Therefore for designer $A\beta_{1-14}$ peptide immunogen constructs (SEQ ID NOs: 62 and 63) or peptide immunogen constructs of their analogues, doses beyond 100 ug would be further explored.

Example 8

Criteria for the Development of a Successful Immunotherapeutic Vaccine for the Treatment of Dementia of Alzheimer's Type UBI's strategy to develop an immunotherapeutic vaccine includes design of proprietary promiscuous Th epitopes linking to target B sequence based on platform technology to overcome the "self" barrier and limitation of genetic diversity and the development of optimal peptide-based vaccine formulation which are Safe, Unique, Characterizable, Cost-effective, Efficacious, Stable and Scalable (coined as SUCCESS) (Wang C Y, et al., 2005; Sokoll K K, 2004). Special attention was given at the initial design phase to allow the selected peptide immunogens that will enter the development phase of the program for vaccine formulation to be characterizable from regulatory approval standpoint as this vaccine, when proven efficacious in patients after phase III trial, would be the first full synthetic peptide based vaccine ever be given to patients on a multi-million dose basis ever in human history. Special attention in quality design of the peptides, selected out of many which already was proven to yield to respectable desired immune responses, was given to the "solubility" of the individual peptides to be employed, synthetic chemistry yield and purification hurdles inherent in sequence design when coming to the fine details. A well accepted adjuvant with high safety factor would also be an important factor for consideration, out of the many acceptable choices. A balance between the safety factor and the scale of immunogenicity must be considered. And when immunogenicity is compromised due to safety factor, what other vaccine formulation features can be incorporated to further elevate the immune response. Again, the success of a vaccine resides on its ability to generate the desired immune response in as large and wide population with diverse genetic background as possible, thus a broad Major Histocompatibility Complex (MHC) coverage must also be a very important factor for consideration.

In light of the above consideration in order to achieve at a SUCCESS vaccine targeting at the N-terminus of Aβ molecule, peptides of single sequence instead of in combinatorial form will be chosen despite their relatively weaker immunogenicity when compared to their counter part in a combinatorial library format. Peptide solubility is also a key factor for testing since the highly potent immunogenicity enhancing T helper epitopes usually comprise a long stretch of hydrophobic amino acid residues thus renders the corresponding peptides not soluble. Special care must be given as to whether highly charged residues such as Asp, Glu, Lys, and Arg would be added to specific positions to enhance the peptide solubility. In order to achieve high yield in synthesis, the chemistry involved in all synthetic processes along with intermediates generated were all evaluated extensively to arrive at the optimal sequences the final peptide will assume as the key ingredient of the vaccine formulation. After a balanced consideration of all highly qualified peptide candidates from immunogenicity aspects, two $A\beta_{1-14}$ peptide immunogen constructs (SEQ ID NOs: 64 and 65) were selected, with peptide with SEQ ID NO: 64 being from the MVF series and peptide with SEQ ID NO: 65 being from the HBsAg series, and were further analyzed for further exploration in vaccine formulations.

Figure 2A:
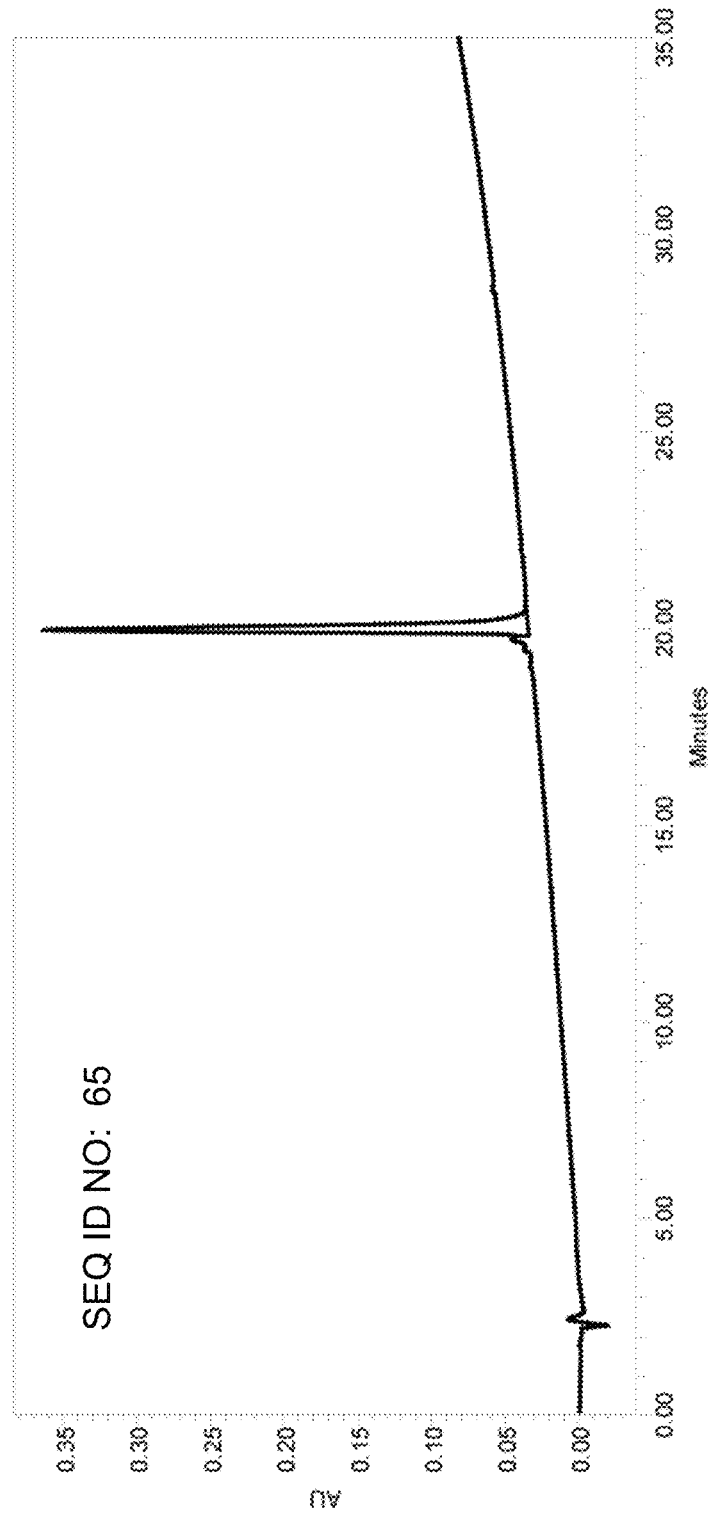
FIG. 2A illustrates the HPLC profile of a highly purified Aβ peptide immunogen construct (SEQ ID NO: 65) with elution time of 20 minutes.
Figure 2B:
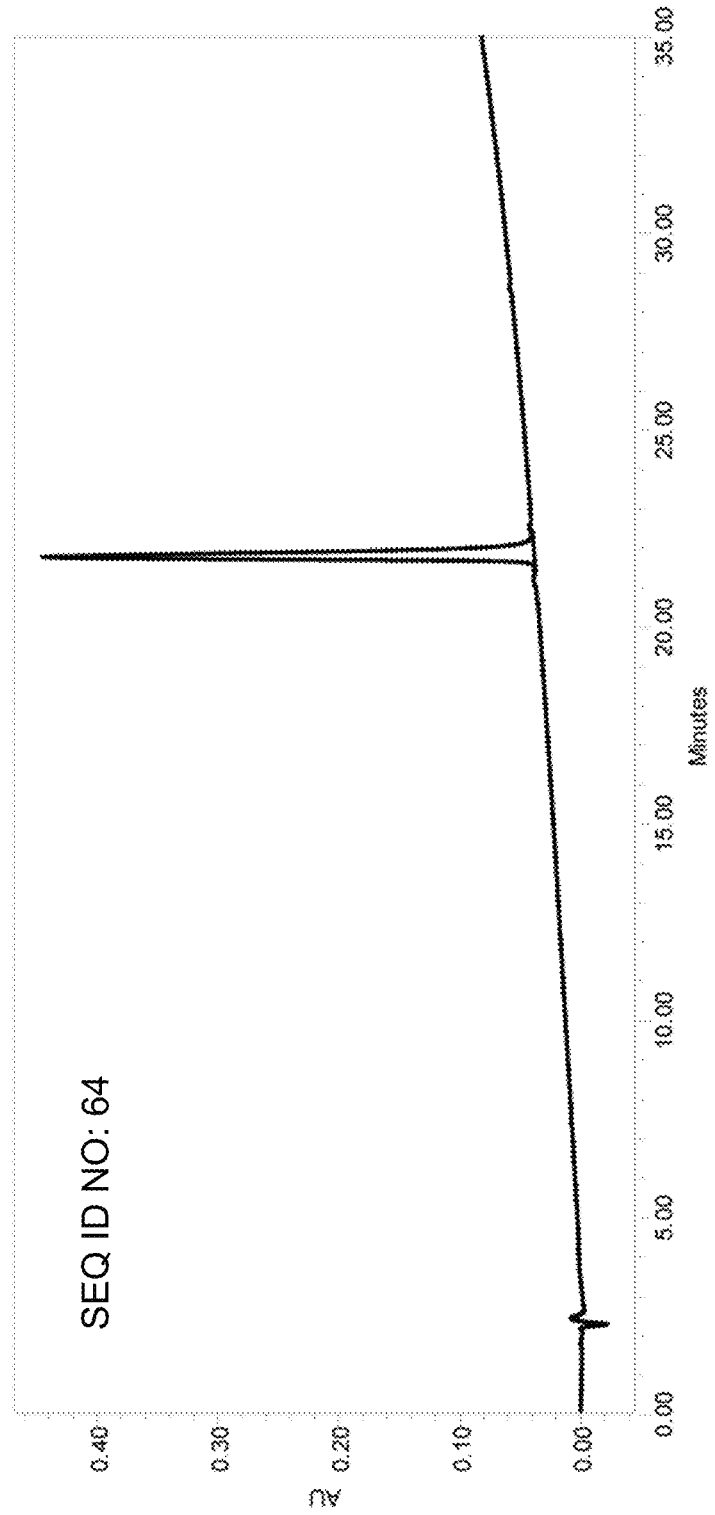
FIG. 2B illustrates the HPLC profile of a highly purified Aβ peptide immunogen construct (SEQ ID NO: 64) with elution time of 21 minutes.
Figure 2C:
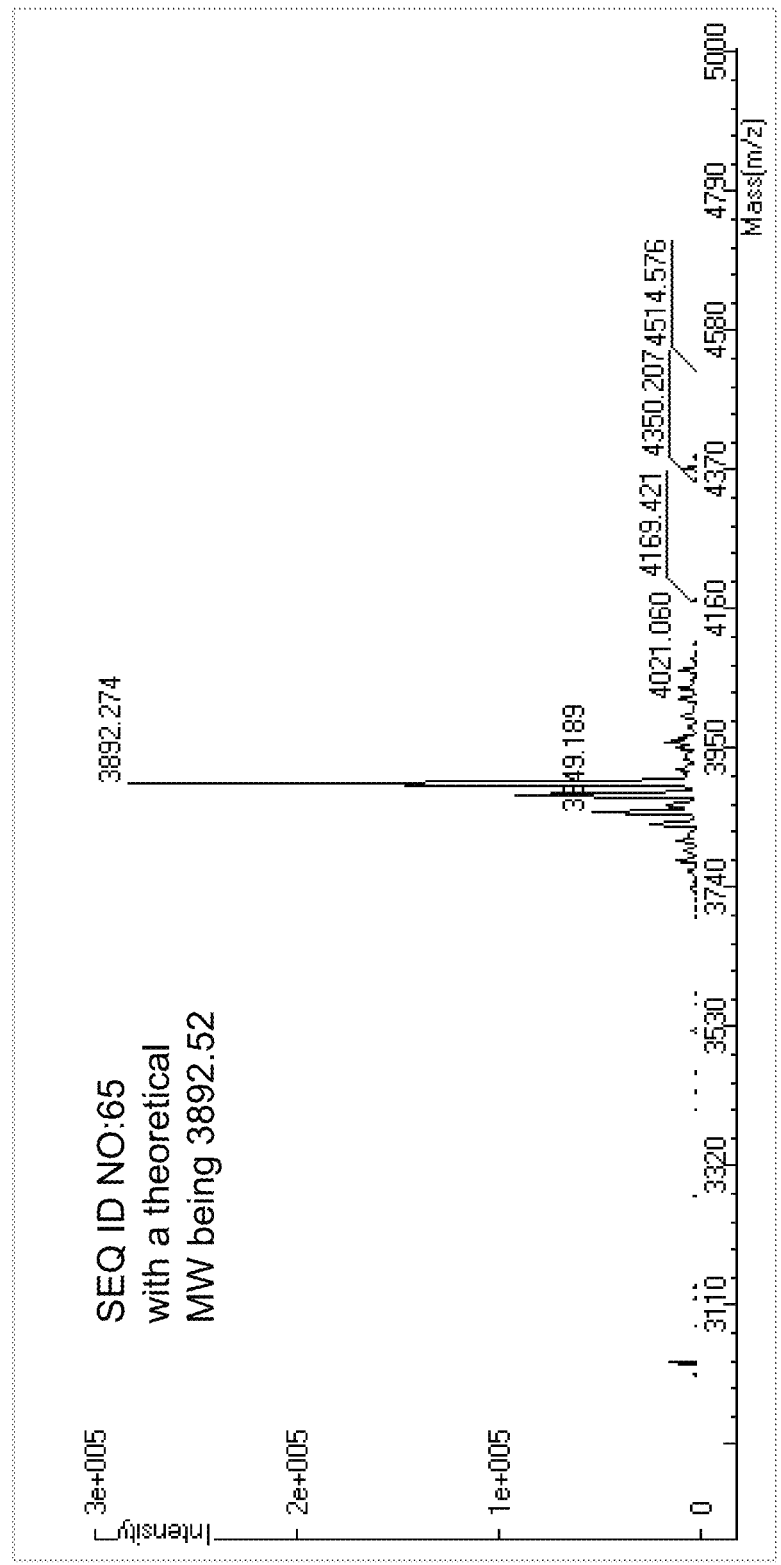
FIG. 2C is a Mass Spectrometry (MALDI-TOF) profile with a molecular weight measured at 3892.274 for Aβ peptide immunogen construct (SEQ ID NO: 65), which has a theoretical molecular weight of 3892.52, showing high precision of the molecular nature used as the active pharmaceutical ingredient in the UBI AD vaccine (UB-311) formulation.
Figure 2D:
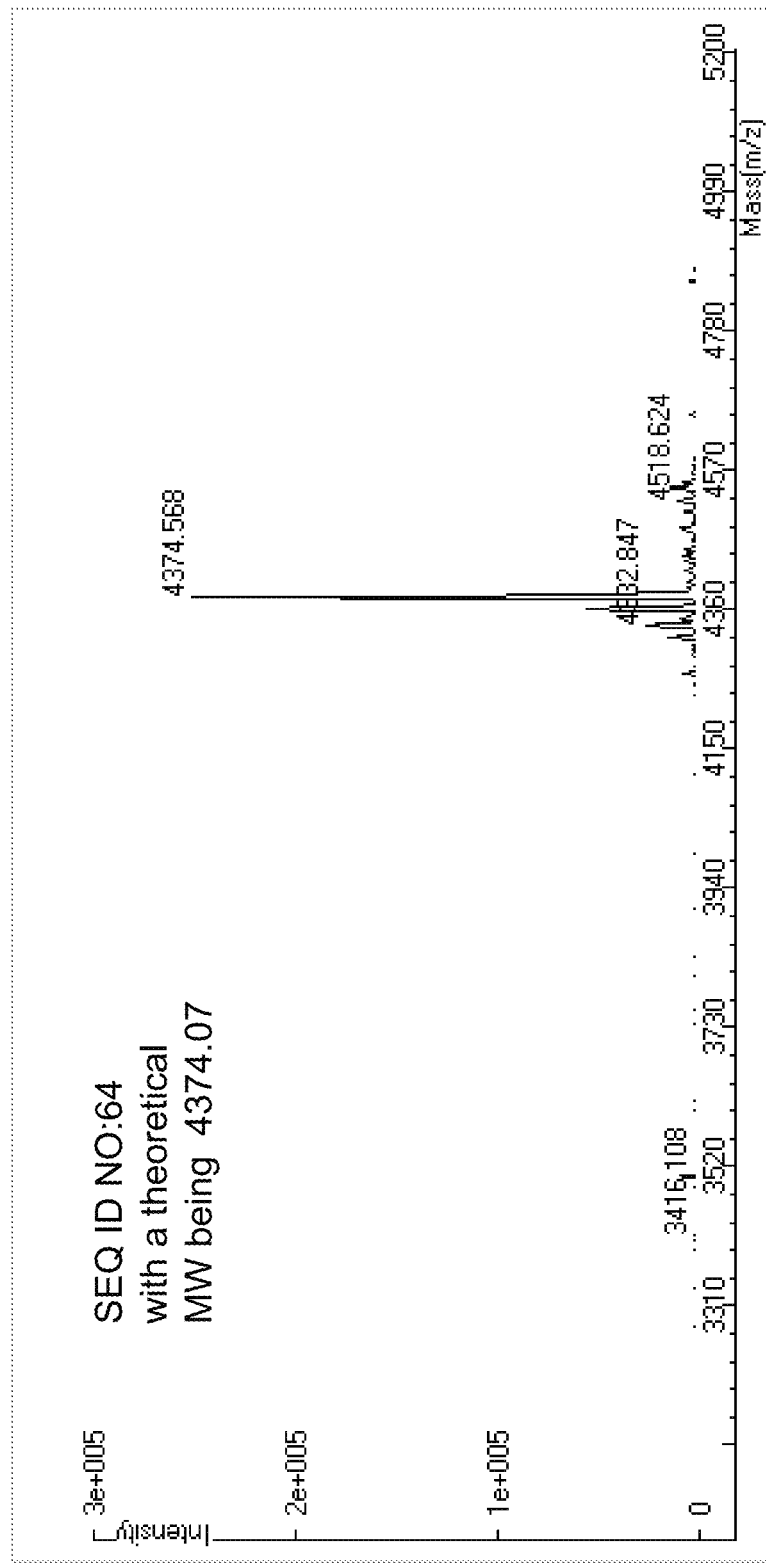
FIG. 2D is a Mass Spectrometry (MALDI-TOF) profile with a molecular weight measured at 4374.568 for Aβ peptide immunogen construct (SEQ ID NO: 64), which has a theoretical molecular weight of 4374.07, showing high precision of the molecular nature used as the active pharmaceutical ingredient in the UBI AD vaccine (UB-311) formulation.
Figure 2E:
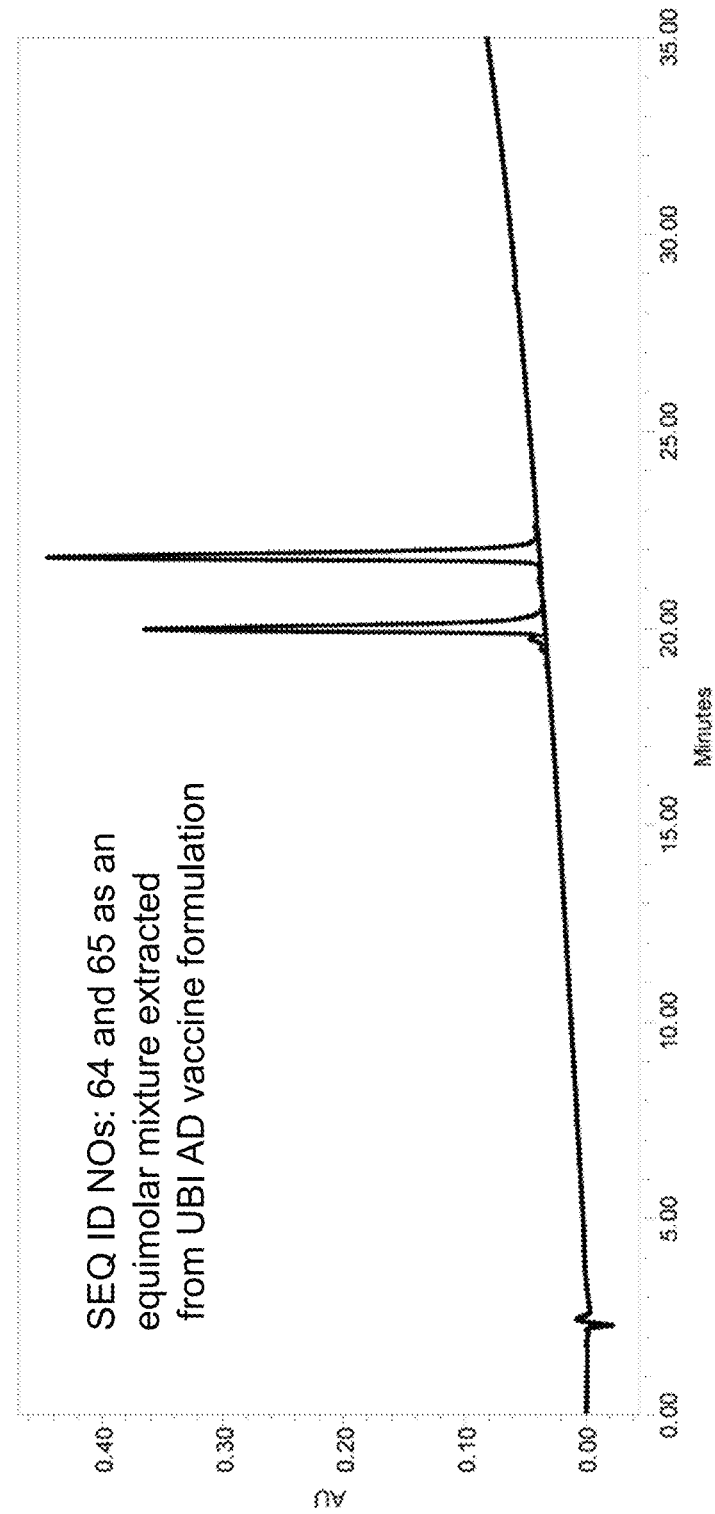
FIG. 2E illustrates the HPLC profiles of highly purified Aβ peptide immunogen constructs (SEQ ID NOs: 65 and 64) with elution times of 20 and 21 minutes, respectively. The two Aβ peptide immunogen constructs (SEQ ID NOs: 64 and 65) were extracted from a UB-311 vaccine formulation preparation after a storage at 2-8° C. over 3 years showing an expected HPLC profile with the elution time at an equal molar ratio as previously mixed illustrating the high precision nature of such a rationally design vaccine formulation.

These peptides were synthesized and purified to high purity as shown in FIGS. 2A, 2B, 2E. The HPLC profiles for both peptides of SEQ ID NOs: 65 and 64 under reverse phase analysis with shallow gradient showed elution time of 20 and 21 minutes, respectively. MALDI-TOF analysis of these purified peptides gave a molecular weight of 3892.274 (with a theoretical value of 3892.52) for peptide with SEQ ID NO: 65 and 4374.568 (with theoretical value of 4374.04) for peptide SEQ ID NO: 64, both with high precision, as shown in FIGS. 2C and 2D.

Figure 3A:
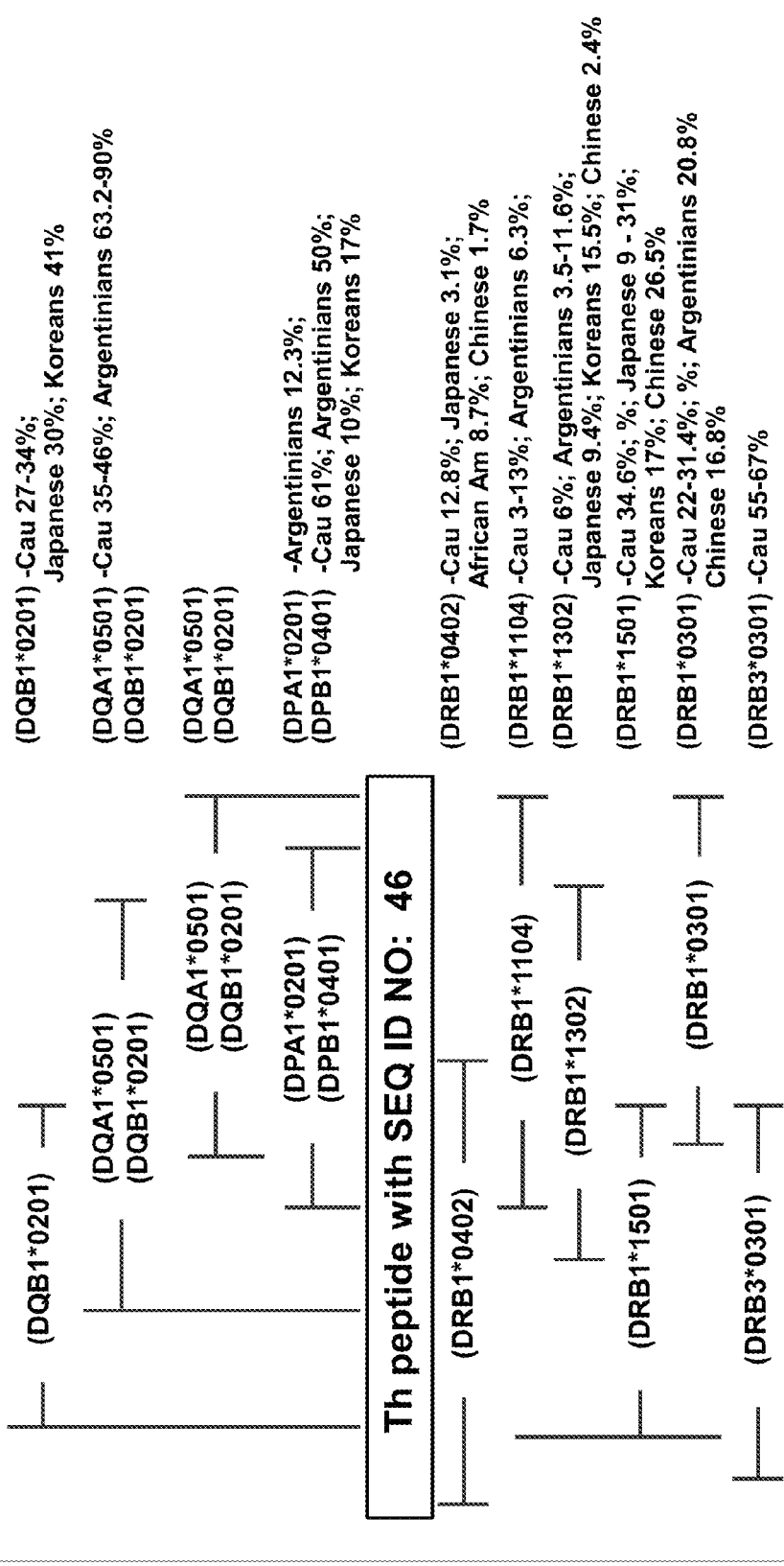
FIG. 3A illustrates the HLA Class II binding motifs of Th peptide SEQ ID NO: 46 based on extensive literature search. Decision was made to use a combination of two Aβ peptide immunogen constructs (SEQ ID NOs: 64 and 65) to broaden the immune responses due to maximal coverage of the genetic background of patients receiving the vaccine.
Figure 3B:
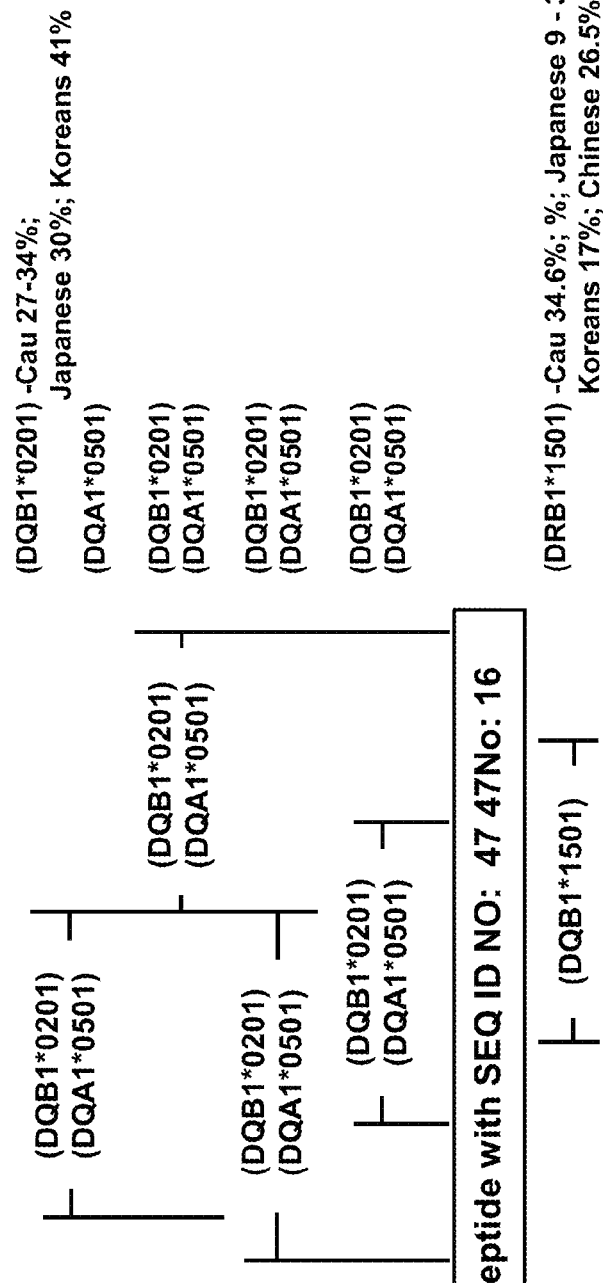
FIG. 3B illustrates the HLA Class II binding motifs of Th peptide SEQ ID NO: 47 based on extensive literature search. Decision was made to use a combination of two Aβ peptide immunogen constructs (SEQ ID NOs: 64 and 65) to broaden the immune responses due to maximal coverage of the genetic background of patients receiving the vaccine.

The "Th" peptides of SEQ ID NOs: 46 and 47, both used to enhance the immunogenicity of $A\beta_{1-14}$ were extensively evaluated for their binding motifs in the various populations as shown in FIGS. 3A and 3B. It is safe to incorporate two promiscuous T helper epitopes into the vaccine design in order to allow maximal coverage of the genetic background of all patients. From the percentage coverage analyzed, this vaccine will have a very reasonable chance to cover a large population, if not all, of patients receiving the vaccine, an important factor to justify the extensive testing and development efforts extended to a vaccine of high clinical value.

Figure 4:
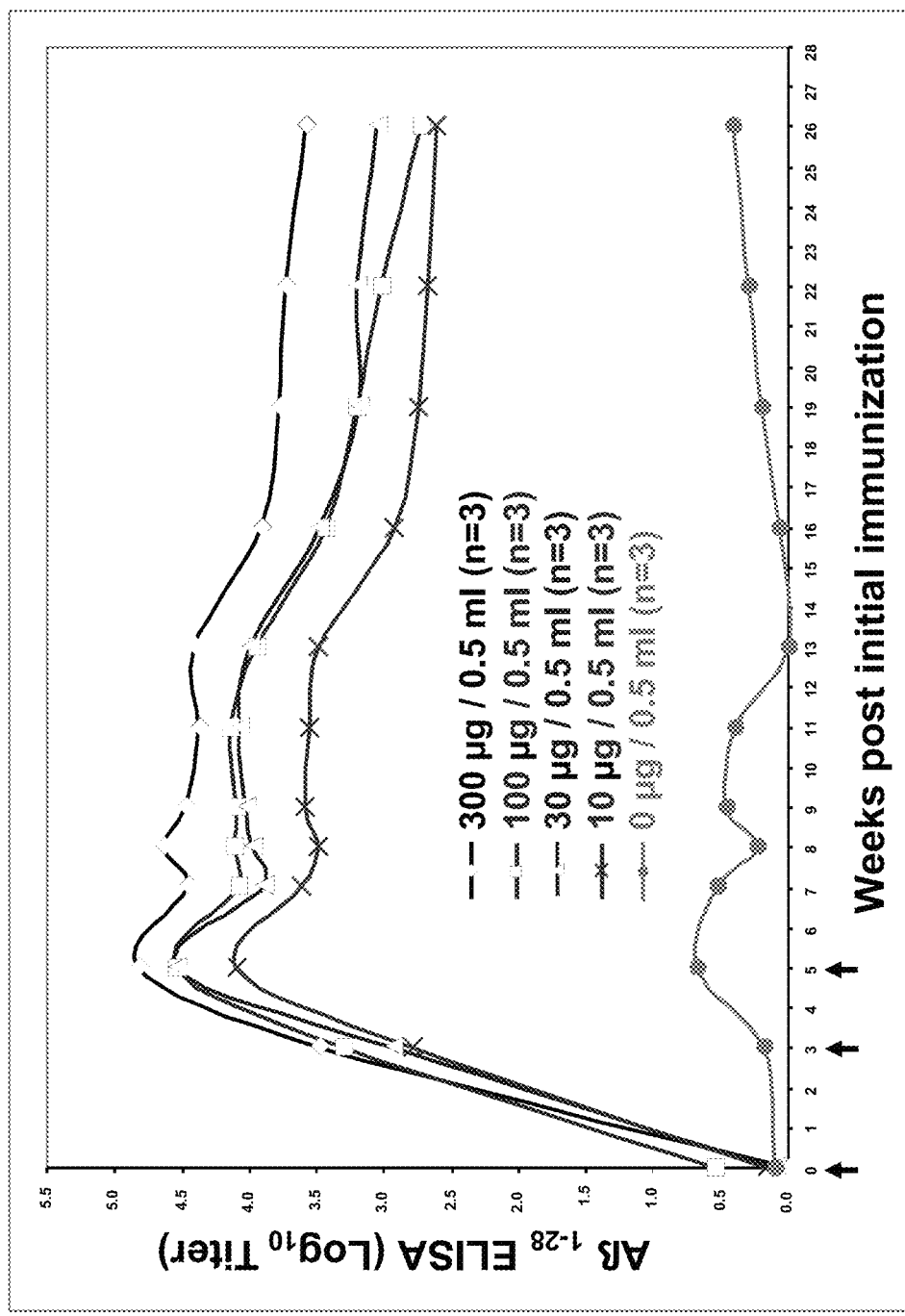
FIG. 4 illustrates the Kinetics of antibody response over a 26-week period in guinea pigs to vaccine formulations incorporating varying amounts (from 0, 10, 30, 100 to 300 μg per 0.5 mL dose) of Aβ peptide immunogen constructs (SEQ ID NOs: 64 and 65) in combination with a fixed amount of mineral salts.

In order for a vaccine designed to be used by a large population and with prevention also being part of the goal for administration, safety becomes another important factor for consideration. Despite the use of water-in-oil emulsions in humans for many vaccine formulations in clinical trials, Alum remains the major adjuvant for use in vaccine formulations due to its decades of safety testing. Alum or its mineral salts ADJU-PHOS® (Aluminum phosphate) were considered for use as adjuvants in preparation for clinical applications.

a. Assessment of Immunogenicity in Guinea Pigs after Prime (0 Wpi) and Boosts (3 and 5 Wpi) of Vaccine Formulations Containing Varying Amounts of Highly Purified Aβ1-14 Peptide Immunogen Constructs (SEQ ID NOs: 64 and 65) with a Fixed Amount of Mineral Salts After selection of the two highly purified $A\beta_{1-14}$ peptide immunogen constructs (SEQ ID NOs: 64 and 65) out of many immunogenic candidates for development of a UBI AD vaccine for preclinical and clinical testing, a mixture of these two peptides in an equimolar ratio was tested for their immunogenicity in the presence of a fixed amount (0.5 mL) of alum/mineral salts in a dosing study in guinea pigs as shown in FIG. 4. Varying amounts of the peptide mixture containing the above mentioned two $A\beta_{1-14}$ peptide immunogen constructs (SEQ ID NOs: 64 and 65) from 0 µg, 10 µg, 30 µg, 100 µg to 300 µg in 0.5 mL of mineral salts (Aluminum phosphate, ADJU-PHOS®) were tested in guinea pigs based on an immunization schedule of 0, 3 and 5 wpi (weeks post initial immunization) with the immunogenicity observed for over a 26 weeks period. At peak of the immune response which is around 5 weeks post initial immunization, animals receiving 300 µg per dose gave the highest immune response followed by those receiving 100 µg and 30 µg, then by 10 µg dose with similar immune response ranking throughout the 26 weeks period followed. The highest dose at 300 µg per 0.5 mL ADJU-PHOS® is therefore considered an optimal condition for immunization and will be used as a guide to explore immunogenicity in other related formulations in different species.

b. Means to Further Elevate the Immunogenicity of the Vaccine Formulations Through Formation of an Immunostimulatory Complexes (ISC) Between Peptides and Oligonucleotides Inherent with the use of Alum or its associated mineral salts as adjuvant, the associated vaccine formulation immunogenicity would also be reduced by about one $Log_{10}$ in titer for their target Aβ$_{1-14}$ B cell epitopes (as estimated in a similar study in Example 7). Means to further elevate the immunogenicity of the vaccine formulation is therefore explored.

More specifically, in UBI formulation as shown in FIG. 5A, a stabilized immunostimulatory complex (ISC) is derived from cationic peptides and a polyanionic CpG oligodeoxynucleotide (ODN) molecule (upper panel) (Sokoll K K, 2004). It is a self-assembling system driven by electrostatic neutralization of charge. Stoichiometry of the molar charge ratio of cationic peptide to anionic oligomer determines extent of association. The non-covalent electrostatic association of peptide immunogens and CpG ODN is a completely reproducible process. The peptide/CpG ODN immunostimulatory complex aggregates which facilitate presentation to the "professional" antigen processing cells (APC) of the immune system thus further enhancing of the immunogenicity of the complexes. These complexes are easily characterized for quality control during manufacturing. The peptide/CpG ISC are well tolerated in vivo.

The immunostimulatory complexes can then be combined with the mineral/aluminum salt adjuvant forming an aqueous suspension as shown in the lower panel of FIG. 5B.

CpG motifs have been characterized as agonists of Toll-like receptor 9 (TLR9), found in a subset of dendritic cells (pDC) and B cells. Toll-like receptors have the ability to recognize the distinct molecular patterns characteristic of common foreign invaders such as bacteria, viruses and parasites. Specifically unmethylated, synthetic CpG sequences are capable of binding to and activating TLR9. As potent B-cell mitogens, TLR9 agonists are effective in inducing strong antibody immune responses. The mechanism of CpG action involves, amongst them, the development of long-lasting antigen specific antibodies.

In view of the AN1792 Aβ$_{1-42}$ peptide vaccine clinical trial which failed both in its immunogenicity in eliciting in only 30% of the patients antibodies directed to the targeted Aβ$_{1-42}$ aggregated vaccine and caused in 6% of patients meningoencephalitis-like side effects, The aluminum-based adjuvants employed in this invention for the UBI AD vaccine are known to stimulate Th-2 type of immune responses (i.e., IL-4 and IL-5 cytokines). In addition, the Aβ peptide immunogen construct/CpG ODN immunostimulatory complexes are particulate. Processing of particulate immunogens is facilitated by APC that biases a Th-2 type of response.

In summary, CpG oligonucleotides have been Safely used in several human clinical trials (>1,000 patients). Peptide/CpG ODN derived immunostimulatory complexes are easily Characterized. Stable under physiological conditions and well tolerated in vivo. CpG-based complexes derived from numerous peptide immunogens alone or in combination with mineral salts have been proven to be Efficacious in mice, guinea pigs, swine, dogs, cattle, baboons and macaques with minimal adverse events reported. Aluminum-based mineral salts are the only adjuvants included in currently licensed vaccines in the USA. Vaccine compositions employing these adjuvants are Cost-effective and known to Scale efficiently. Specific vaccine/adjuvant formulations are licensed vs. adjuvant alone. UBI has explored and developed Unique compositions The above described features of the UBI AD vaccine for treatment of dementia has all the elements required to be a SUCCESS.

Example 9

Formulation of UBI AD Vaccine for Intramuscular Injection

Figure 6:
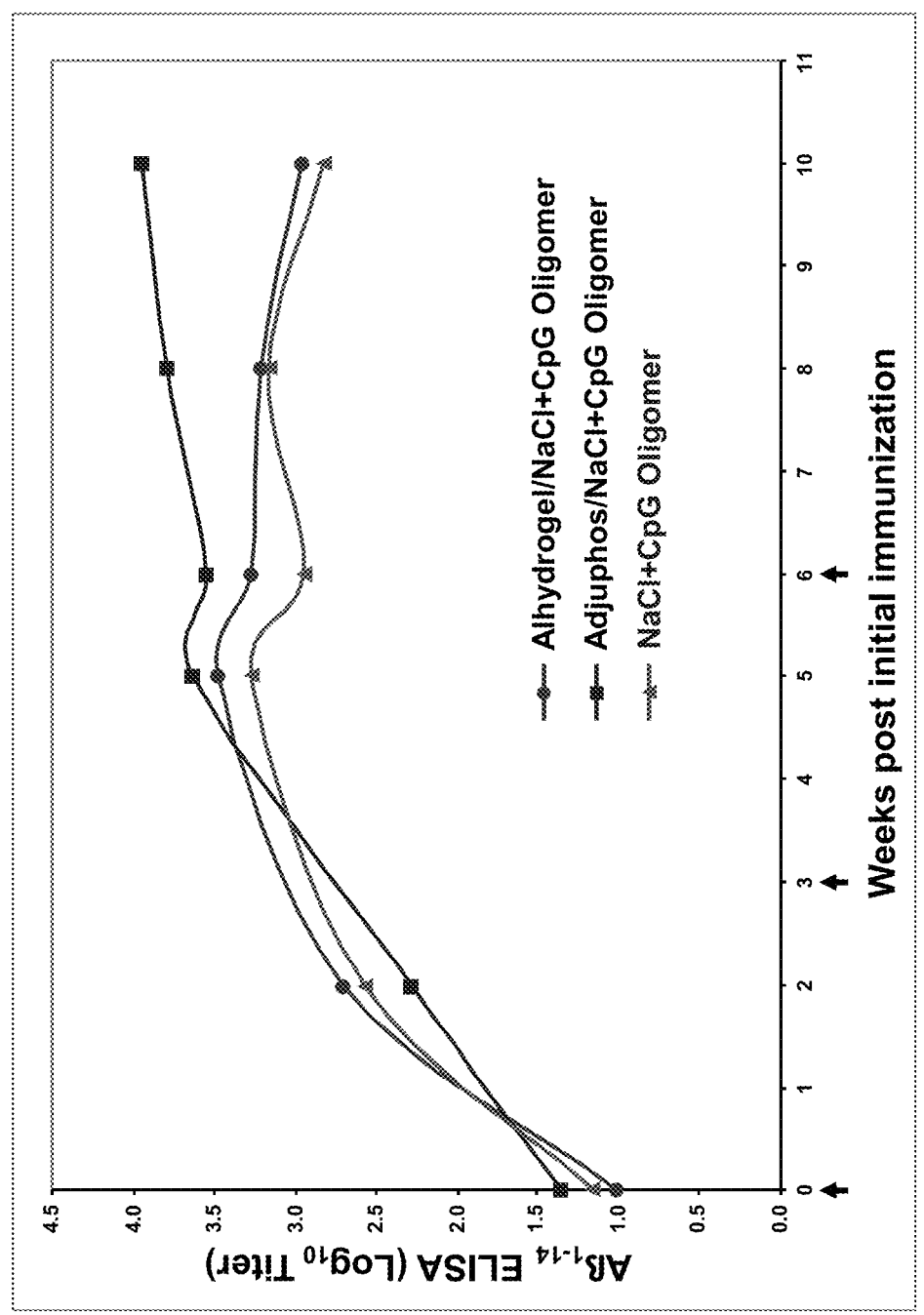
FIG. 6 illustrates the Kinetics of antibody response over a 10-week period in baboons of vaccine formulations at 300 μg/0.5 mL/dose of Aβ peptide immunogen constructs in the presence of different adjuvants (ALHYDROGEL®/NaCl+ CpG ODN; ADJU-PHOS®/NaCl+CpG ODN; and NaCl+ CpG ODN).

The Aβ$_{1-14}$-εK-KKK-MvF5 Th peptide immunogen construct (SEQ ID NO: 64) and the Aβ$_{1-14}$-εK-HBsAg3 Th peptide immunogen construct (SEQ ID NO: 65), are cationic at physiological pH's. FIGS. 2A, 2B, 2C (left side) illustrates the HPLC profiles of the two peptides alone and in an equal molar ratio mixture. FIGS. 2D and 2E (right side) illustrate the profiles characterized by MALDI-TOF mass spectrometry of the two peptides with a molecular weight (Da) of 3892 and 4374, respectively. The addition of polyanionic CpG ODN results in charge neutralization and immediate "self-assembly" of immunostimulatory complexes (ISC) in solution. Stoichiometry of the molar charge ratios of cationic peptide: anionic CpG determines the degree of association. The UBI AD vaccine was prepared in stages: The ISC was prepared in water-for-injection with an equimolar mixture of the two Aβ peptide immunogen constructs with a molar charge ratio to CpG ODN of about equal.

a. Assessment of Immunogenicity Over a 10-Week Period in Baboons after Prime (0 Wpi) and Boosts (3 and 6 Wpi) of Vaccine Formulations Containing 300 µg/0.5 mL of Highly Purified Aβ$_{1-14}$ Peptide Immunogen Constructs (SEQ ID NOs: 64 and 65) Forming Immunostimulatory Complexes with CpG Oligomers in the Absence or Presence of Alum or ADJU-PHOS® as an Adjuvant Based on the first level of immunogenicity and dosing study in guinea pigs with the highly purified Aβ$_{1-14}$ peptide immunogen constructs (SEQ ID NOs: 64 and 65), a mixture of 300 µg containing the two Aβ$_{1-14}$ peptide immunogen constructs (SEQ ID NOs: 64 and 65) at an equimolar ratio were prepared as immunostimulatory complexes with CpG oligomers as described above. They were then formulated either with alum or ADJU-PHOS®, or no adjuvant, for immunization into baboons at 300 µg peptide per dose for intramuscular injection based on a 0, 3, 6 weeks immunization protocol with the specific antibody levels observed over a 10 weeks period. Baboons were used for such immunogenicity assessment and final formulation assessment prior to entering into human trials since this animal species generates immune responses most resembling that of humans in scale. All vaccine formulations were given to the animals in 0.5 mL per dose and two animals per group. As shown in FIG. 6, at 300 µg in 0.5 mL per dose, all three formulations, in the presence or absence of alum or ADJU-PHOS® as the adjuvant, demonstrated immunogenicity at about the same level, within 0.5 Log$_{10}$ in scale, as demonstrated by ELISA towards the Aβ$_{1-14}$ peptide. The ISC formulation significantly enhanced the immunogenicity exerted by the peptide alone. However, after observation over an 8 to 10 week period, the formulation supported by ADJU-PHOS® maintained a significantly higher immune response when compared to the other two groups, enlarging from 0.5 to 1 Log$_{10}$ in response scale (i.e., about 3 to 10 fold more potent). Through this careful calibration of the immunogenicity in baboons with three closely related formulations, designed to be of high safety factors by using highly purified rationally designed peptides generating very focused and desired immune responses without any complicating factors from adjuvant, the UBI AD vaccine formulation is therefore finalized for further exploration in primates and humans for immunogenicity, specificity, functional properties related to the elicited antibodies, acute and chronic toxicity, and finally clinical efficacy as illustrated in the following Examples.

b. Preparation of UBI AD Vaccine Formulation for Immunogenicity, Acute Toxicity, Chronic Toxicity, Efficacy, and Clinical Safety, Tolerability and Efficacy Studies.

The ISC was prepared in water-for-injection with an equimolar mixture of the two Aβ peptide immunogen constructs (SEQ ID NOs: 64 and 65) which is further mixed with CpG at a molar charge ratio of peptides to CpG ODN of about equal. The CpG ODN in the UBI AD vaccine formulations are 100% bound to the peptide immunogen constructs in a process mediated by electrostatic neutralization of opposing charge, resulting in the formation of micron-sized particulates. The particulate form allows for a significantly reduced dosage of CpG ODN from the conventional use of CpG adjuvants, less potential for adverse innate immune responses, and facilitates alternative immunogen processing pathways including professional antigen presenting cells (APC). To the preformed ISC was sequentially added the aluminum mineral salt, a saline solution for tonicity and a preservative. Of the Aluminum mineral salts, aluminum phosphate was used instead of Alum gel based on the baboon immunogenicity study results for better sustenance of the immunogenicity.

c. Stability and Immunogenicity Study of the UBI AD Vaccine Formulation

UBI AD vaccine formulation prepared at 300 μg in 0.5 mL per dose with aluminum phosphate (ADJU-PHOS®) as the adjuvant with an overage of 20% was prepared as described above and filled in an 1 mL sterile glass vial and stored at 2-8° C. for 2 years. Samples were retrieved according to a stability testing protocol. All physical parameters met quality control (QC) specifications. The $A\beta_{1-14}$ peptide immunogen constructs were decomplexed from the CpG oligodeoxynucleotide (ODN) and the ADJU-PHOS® adjuvant and analyzed by HPLC according to the analytical specifications for each of the peptides. As shown in the lowest panel on the left of FIG. 2C the two $A\beta_{1-14}$ peptide immunogen constructs (SEQ ID NOs: 64 and 65) revealed an equimolar mixture of the two respective peptides at the expected elution time upon HPLC analysis.

Figure 7:
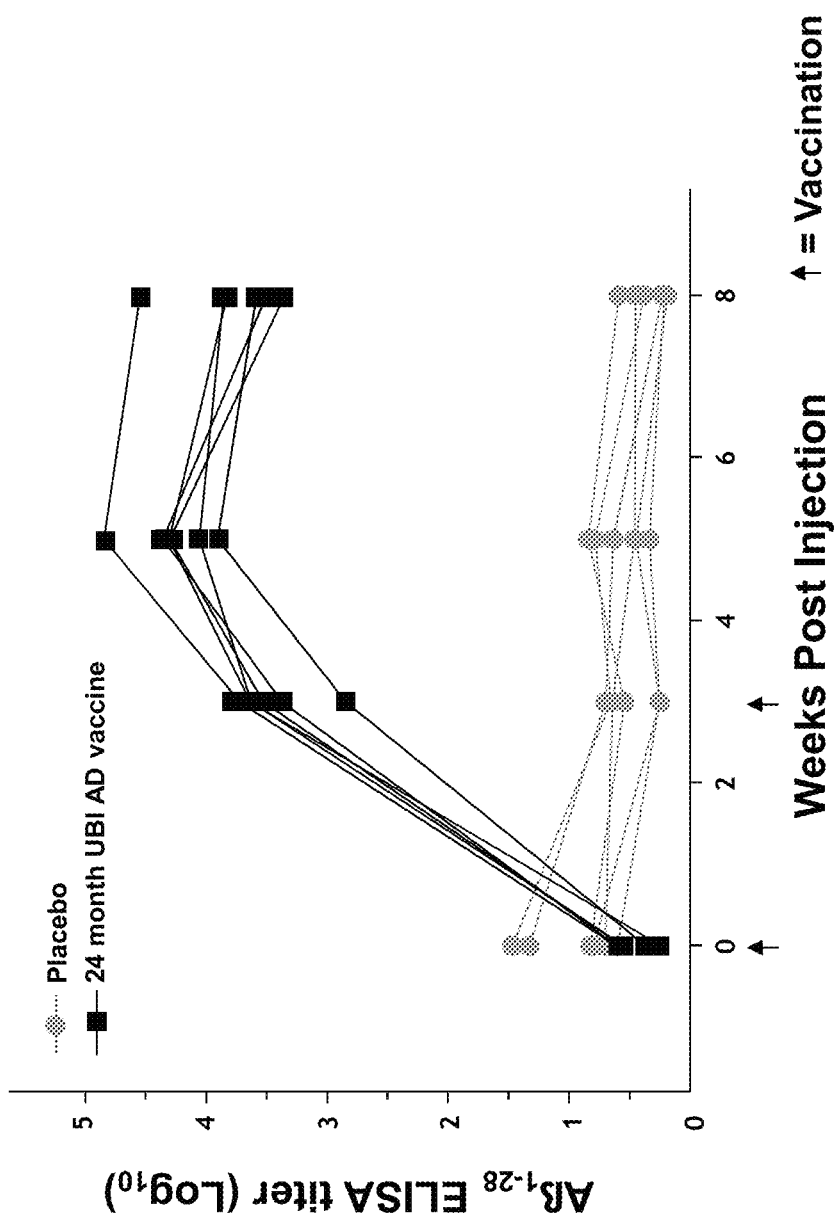
FIG. 7: Immunogenicity study in guinea pigs of UBI AD vaccine comprising Aβ peptide immunogen constructs (SEQ ID NOs: 64 and 65 at equimolar ratio) after a 2-year storage at 2 to 8° C. The UBI AD vaccine remained highly immunogenic and stable after a standard prime and boost (3 wpi) protocol.

Vials containing UBI AD vaccine formulation were retrieved for immunogenicity study in guinea pigs. Two groups, each having six animals, were tested with one being the vaccine group where 300 μg per dose was given at 0 and 3 wpi while the other group was given placebo vaccine formulation (i.e., the same formulation without the two peptide immunogen constructs). As shown in FIG. 7, significant immunogenicity was achieved by all animals upon single administration reaching a peak response by 5 wpi after a boost at 3 wpi Immune sera taken from 8 wpi were further tested for their reactivity with the respective Th peptides employed to provide the immunogenicity enhancement. As shown in Table 8, little if any reactivity was directed to the Th peptides to further confirm the "Immunosilent" nature of these two Th peptides thus allowing a very focused immune response directed towards exclusively to the N-terminus of the Aβ peptide. The UBI AD vaccine formulation is therefore comprised of well defined chemicals, away from the historic vaccine industry dealing exclusively with the not well characterized biological materials, generating focused immune response as designed, and is more broadly reactive than the monoclonal antibodies thus more effective in efficacy, yet far cleaner than the conventional peptide-carrier conjugated type of vaccines, thus commanding a high safety factor.

Example 10

Figure 8:
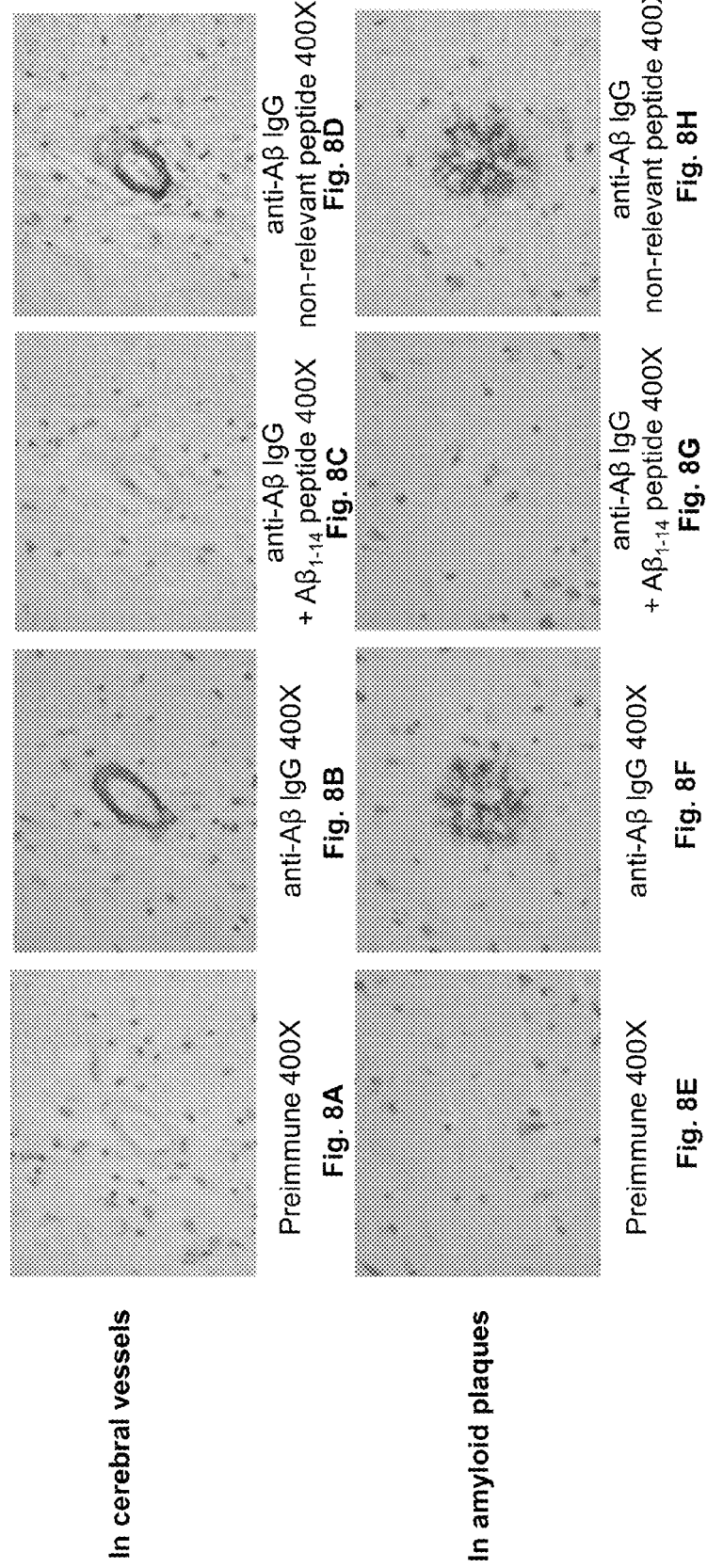
FIG. 8A: illustrates cerebral vessels from a human AD brain are not immunohistochemically stained with IgG fractions from preimmune baboon sera.
FIG. 8B: illustrates cerebral vessels from a human AD brain show immunohistochemical staining with purified IgG from hyperimmune sera from baboons immunized with an equimolar ratio of the Aβ peptide immunogen constructs SEQ ID NOs: 62 and 63.
FIG. 8C: illustrates cerebral vessels from a human AD brain are not immunohistochemically stained with the purified IgG from hyperimmune sera described for FIG. 8B that was preincubated with $A\beta_{1-14}$ peptide. This figure shows that preincubation with the $A\beta_{1-14}$ peptide absorbed out all immunoreactivity of cerebral vessels by the purified IgG from the hyperimmune sera, demonstrating the high specificity of the hyperimmune sera by vaccination with a vaccine formulation comprising Aβ peptide immunogen constructs (SEQ ID NOs: 62 and 63).
FIG. 8D: illustrates cerebral vessels from a human AD brain show immunohistochemical staining with purified IgG from hyperimmune sera described for FIG. 8B that was preincubated with a non-relevant peptide.
FIG. 8E: illustrates amyloid plaques from a human AD brain are not immunohistochemically stained with IgG fractions from preimmune baboon sera.
FIG. 8F: illustrates amyloid plaques from a human AD brain show immunohistochemical staining with purified IgG from hyperimmune sera from baboons immunized with an equimolar ratio of the Aβ peptide immunogen constructs SEQ ID NOs: 62 and 63.
FIG. 8G: illustrates amyloid plaques from a human AD brain are not immunohistochemically stained with the purified IgG from hyperimmune sera described for FIG. 8B that was preincubated with $A\beta_{1-14}$ peptide. This figure shows that preincubation with the $A\beta_{1-14}$ peptide absorbed out all immunoreactivity of cerebral vessels by the purified IgG from the hyperimmune sera, demonstrating the high specificity of the hyperimmune sera by vaccination with a vaccine formulation comprising Aβ peptide immunogen constructs (SEQ ID NOs: 62 and 63).
FIG. 8H: illustrates amyloid plaques from a human AD brain show immunohistochemical staining with purified IgG from hyperimmune sera described for FIG. 8B that was preincubated with a non-relevant peptide.

Immunohistochemical Staining of Human Brain with Alzheimer's Disease to Assess Serological Specificity and Safety of the UBI AD Vaccine Hyperimmune sera from Groups 3 and 4 baboons immunized with the Aβ peptide immunogen constructs (SEQ ID NOs: 62 and 63) at equimolar ratio described in EXAMPLE 7, were pooled with IgG fraction purified and tested for their reactivity with human AD brain. As shown in FIG. 8, staining with both cerebral vessels and amyloid plaques was found by purified IgG from hyper immune sera but not from similar IgG fractions from the preimmune sera. Preincubation of the immune sera with $A\beta_{1-14}$ peptide absorbed out all immunoreactivity with both cerebral vessels and amyloid plaques, but not by a non-relevant peptide, demonstrating the high specificity of the anti-Aβ antibody reactivity in the immune sera by vaccination with a vaccine formulation comprising Aβ peptide immunogen constructs (SEQ ID NOs: 62 and 63).

Another immunohistopathology study using preimmune and hyperimmune guinea pig IgG was performed on cryostat sections of adult normal human tissues in order to monitor for specificity and undesirable antibody autoreactivities. The panel of human tissues (N=32) was screened for immunoreactivity with purified anti-$A\beta_{1-14}$ IgG from guinea pigs immunized with the UBI AD immunotherapeutic vaccine and compared to preimmune purified IgG from the same animals. The immunostaining patterns observed on sections of adult normal tissues were reviewed by certified clinical pathologists at PhenoPath Laboratories. Except for weak positive immunoreactivity of some muscle tissues (e.g., endometrium), all adult human tissues tested were negative other than strong positive reactivity on senile plaques in one of three adult cerebrum specimens and positive immunostaining of cerebral fluid within spinal cord samples.

Example 11

Figure 9:
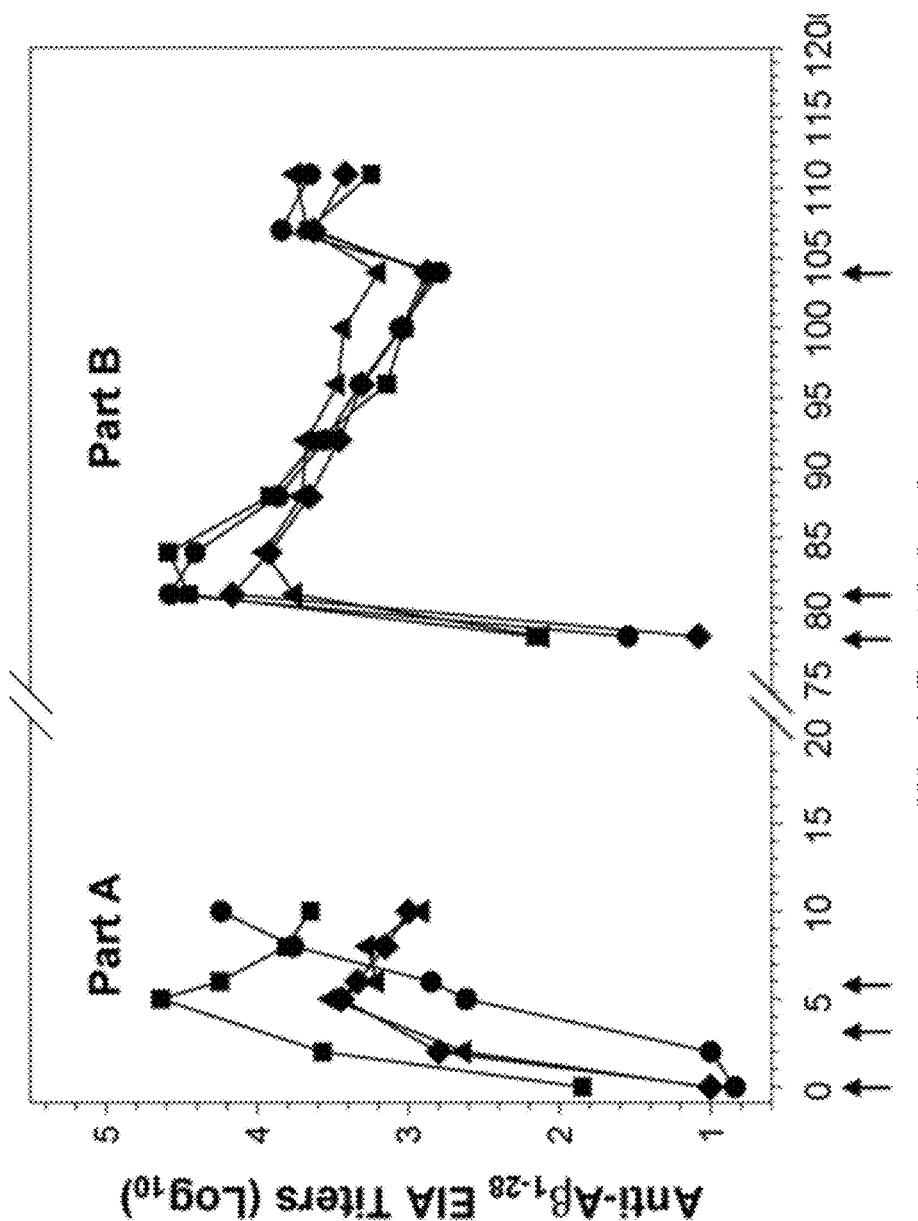
FIG. 9: Immunogenicity study of the UBI AD vaccine in adult baboons, *P. anubis*. (Part A) Individual baboons immunized at 0, 3, 6 weeks (arrows) with 300 μg per dose of the UBI AD vaccine formulated in mineral salts (♦, ▲, ●, ■) and assayed for anti-Aβ antibody titers by ELISA. Note that three of four baboons generated anti-Aβ antibody titers after the first immunization. (Part B) Individual baboons immunized after a 72 week rest period, at 78, 81 and 104 weeks (arrows), with 300 μg (low dose, ●, ■) or 1200 μg (high dose, ♦, ▲) of the UBI AD vaccine formulated in mineral salts and assayed for anti-Aβ antibody titers. Note that all four baboons developed strong anti-Aβ antibody responses after a single vaccine boost. At the end of the 2-year study period, all four baboons remained healthy and active.

Immunogenicity Studies of the Prototype UBI AD Vaccine Formulations in Adult Baboons In Part A of the protocol, four adult male baboons were immunized at 0, 3 and 6 weeks with $A\beta_{1-14}$ peptide immunogens (300 μg total peptide per dose) complexed into proprietary immunostimulatory complexes (ISC) and formulated with aluminum mineral salt adjuvants. The ISC/mineral salt formulations resulted in strong anti-Aβ antibody responses in all animals (FIG. 9A). No adverse injection site reactions were noted.

The aims for Part B of the protocol were: (1) to monitor safety and injection site reactogenicity of repeated exposure at the target clinical dose and at a four-fold higher dose, (2) to monitor immunogenicity in a dose escalation study and (3) to evaluate the kinetics of the recall antibody response. These animals were then rested for 72 weeks. In the interim, serum levels of anti-Aβ antibodies had diminished by 10-100-fold. At 78 and 81 weeks post-initial injection (FIG. 9B), four animals were administered vaccines in either 300 μg peptide doses to animal numbers 564 and 565 or 1200 μg doses to animal numbers 556 and 561. The recall responses rapidly restored peak antibody titers in all four baboons. By week 104, antibody titers had begun to decline and the animals were again restored to peak titers by booster doses at week 104. The kinetics of the serum anti-Aβ antibody responses were determined at weeks 0, 2, 5, 6, 8, 10, 78, 81, 84, 88, 92, 96, 100, 104, 107 and 111 by anti-$A\beta_{1-28}$ peptide ELISA. No injection site reactions were noted in animals receiving the 300 μg dose. However, some redness and inflammation were noted at the sites of injection for the baboons receiving the high dose (1200 μg) at week 78 only; this transient reaction was fully resolved within one week. No other adverse events or safety concerns were reported throughout the 2 years that the baboons were evaluated.

Example 12

In Vitro Neurotoxicity Assay for Inhibition of Fibrillogenesis and Protection from $A\beta_{1-40}$-Mediated Toxicity by Anti-$A\beta$ Antibody The neurotoxicity assays employed rat pheochromocytoma cell line, PC-12, and aged solutions of the $A\beta_{1-40}$ peptide, as previously described by Solomon B, et al. (Proc Natl Acad Sci USA 1997; 94:4109-4112). The peptide solution was characterized for fibrillar formation by Congo Red binding. On days 6 and 9 the solution bound equivalent amounts of the dye as shown by absorbance, $A_{540nm}$. This observation provided evidence for formation of toxic $A\beta_{1-40}$ aggregates; the day 9 preparation was tested for toxicity to PC-12 cells.

PC-12 cells were grown in tissue culture and suspended into assay medium and placed into the wells of a 96-well round bottom tissue culture plates, $5 \times 10^3$ cells/well in 100 µL. The toxicity of the 37° C.-incubated peptide (i.e., aggregated $A\beta_{1-40}$) and a freshly prepared peptide (i.e., non-aggregated) was tested at 25 and 6.5 µM in duplicates. Controls were PC-12 cells with assay medium only. The plates were incubated for 48 hour at 37° C. in a $CO_2$ incubator. Toxicity to the cells was determined by the Promega CYTOTOX 96® Cytotoxicity Assay (Non-Radioactive Cytotoxicity Assay is a colorimetric alternative to $51^{Cr}$ release cytotoxicity assays). Lysis was determined by absorbance, $A_{492nm}$ and results were presented as the percentage of cytotoxicity compared to 100% lysis.

In Vitro Evaluation of UBI AD Vaccine for Functional Immunogenicity

The neurotoxicity assay using rat pheochromocytoma cell line, PC-12, and aged solutions of the $A\beta_{1-40}$ peptide characterized to be toxic were used to evaluate the functional efficacy of the antibody response to the UBI AD vaccine. Aged $A\beta_{1-40}$ peptide solution was tested for toxicity on PC-12 cells following a one-hour pre-incubation in the presence of guinea pig or baboon anti-$A\beta$ sera from the animal immunization protocols. The anti-$A\beta$ sera were tested at 1:30 and 1:90 dilutions. Final results were presented as percentage inhibition of $A\beta_{1-40}$ fibril aggregation and percentage protection of PC-12 cells from $A\beta_{1-40}$ fibril-mediated cytotoxicity. The preimmune sera from week 0 of both immunization experiments were included as controls. The immune guinea pig sera and baboon sera from weeks 5 and 8, at both the 1:30 and 1:90 dilutions, provided significant inhibition (50 to 70% for guinea pig sera for bleeds collected at both 5 and 8 weeks at both 1:30 and 1:90 dilutions respectively) when compared to the background 5 to 10% inhibition for the preimmune sera at corresponding dilutions; and (75 and 50% for baboon sera for bleeds collected at both 5 and 8 weeks at 1:30 and 1:90 dilutions respectively) when compared to the 15% background inhibition for the preimmune baboon sera in the inhibition of fibrillogenesis assay. Similarly, protection of PC-12 cells from the $A\beta_{1-40}$-mediated toxicity in the range of 60 to 80% was found for these conditions, in comparison to the background results obtained from the preimmune sera from both guinea pigs and baboons. These results establish functional neutralizing activity against toxic $A\beta_{1-40}$ peptide for the antibodies evoked by immunization with UBITH® amyloid-β peptide immunogens. UBITH® represents a collection of promiscuous Th epitopes that either were directly derived from highly antigenic proteins of pathogens such as measles virus fusion protein (MVF), hepatitis B virus surface antigen (HB-sAg), tetanus toxin (TT), and pertussis toxin (PT) or were adapted from these pathogens and designed to hold idealized Th motifs (Wang C Y, Walfield A M., Vaccine 2005; 23 (17-19):2049-2056).

Example 13

Effects of UBI AD Vaccine in a Preventative Mode on Brain Morphology and Amyloid-β Peptide ($A\beta_{1-42}$) Concentration in Brain Samples of Young Transgenic Mice Overexpressing hAPP751

We evaluated the effects of UBI AD Vaccine in a preventative mode on brain morphology and amyloid-β peptide ($A\beta_{1-42}$) concentration in brain samples of young transgenic (tg+) mice over-expressing hAPP751 with the Swedish and the London mutations and in their non-transgenic (ntg) littermates (Rockenstein E M, et al., 1995 and 2001).

Young transgenic (tg+) mice were immunized with the UBI AD Vaccine at ~14 weeks of age in a prevention mode. When brain tissues were immunohistochemically stained with anti-$A\beta_{1-42}$ antibodies for determination of amyloid plaques, the results for these responsive young tg+ mice showed that the plaque load was reduced. When the brain tissues of vaccinated young tg+ mice were biochemically extracted and evaluated for $A\beta_{1-42}$ levels by quantitative assay, results from the young tg+ responder mice indicated a reduction in $A\beta$ deposition. Both of these parameters indicate that reduction of $A\beta_{1-42}$ load is correlated with antibody response to the UBI AD Vaccine.

In addition, the determinations of percent relative microglial cell activation using anti-CD11b antibody and of T cell infiltration using anti-CD3 antibody revealed no evidence for increased immune cell activation in the brains of the AD vaccine-treated young tg+ animals when compared with the untreated tg+ control animals.

a. Overall Purpose:

To assess the effects of intramuscular vaccinations over a 12 to 16 week period with the UBI AD Immunotherapeutic Vaccine on brain amyloid deposition and brain plaque load, as well as human amyloid-β peptide ($A\beta_{1-42}$) levels in plasma.

The transgenic animals constitutively over-express human amyloid precursor protein (hAPP) with the London (717) and the Swedish (670/671) mutations under the regulatory control of the murine Thy-1 promoter (Rockenstein E M, et al., 1995, and 2001). The $A\beta_{1-42}$ deposition occurs as early as 3 to 4 months of age with the appearance of mature plaques in the frontal cortex and at 5 to 7 months of age, plaque formation extends to the hippocampus, thalamus and cortical projections areas of the olfactory stream in the hAPP751 tg+ mice.

b. Protocol Summary for Prevention Mode

The hAPP751 transgenic (tg+) mice and their non-transgenic (ntg) littermates (14+2 weeks) were selected to evaluate the effects of the UBI AD vaccine on brain $A\beta$ deposition, and brain $A\beta$ plaque load. A total of 33 tg+ mice and 10 ntg mice were separated into 4 groups: tg+ placebo control mice (n=10) were injected with the adjuvant only; tg+ experimental mice (n=13) were injected with the UBI AD vaccine (90 µg per 150 µL dose); untreated tg+ control mice (n=10); and untreated ntg control mice (n=10). A total of three doses were administered at 0, 3, 12 weeks and an additional dose was administered at week 16. At week 25.5, all mice were monitored for spatial learning by the Morris water maze test. The mice were followed for an additional 4 weeks and then sacrificed.

c. Determination of Anti-$A\beta_{1-28}$ Antibody Titer

All tg+ and ntg mice were bled at weeks 0, 3, 6, 9, 12, 16, 19, 22, and 29. Serum was separated for determination of anti-Aβ$_{1-28}$ antibody titers using the Aβ$_{1-28}$ ELISA. None of the placebo-treated tg+ mice and untreated tg+ mice had detectable anti-Aβ$_{1-28}$ antibody titers. However, young tg+ mice that received at least two UBI AD vaccine injections had detectable antibody titers.

d. Brain Morphology and Analysis of Amyloid Deposition and Plaque Load

Figure 10A:
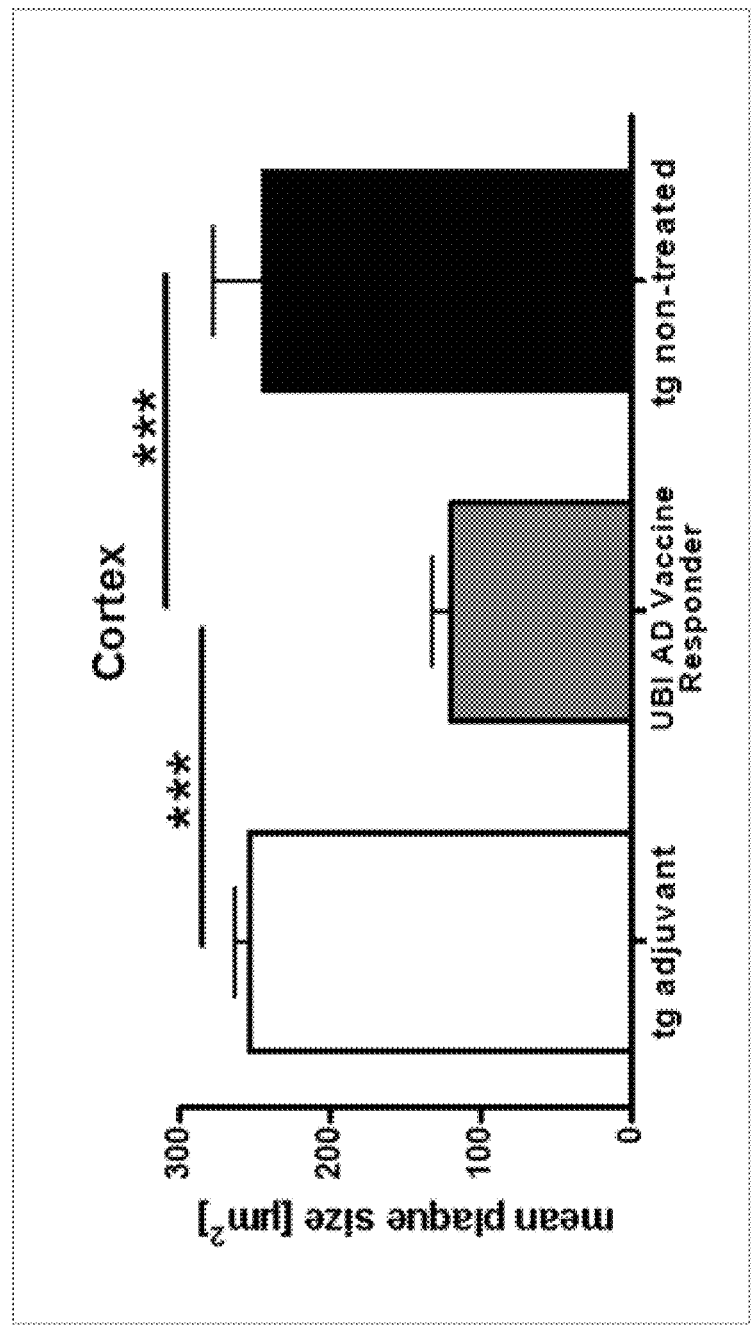
FIG. 10A: illustrates effect of UBI AD vaccine in a prevention mode on brain morphology of the cortex from young transgenic mice overexpressing hAPP751. Brain samples obtained from transgenic mice treated with adjuvant alone, Responders from mice treated with UBI AD vaccine, and the non-treated mice were analyzed for amyloid beta plaque load and found reduced number of plaques and "lower mean plaque size per um$^2$" in UBI AD treated Responder mice when compared to the untreated and those treated with adjuvant alone.
Figure 10B:
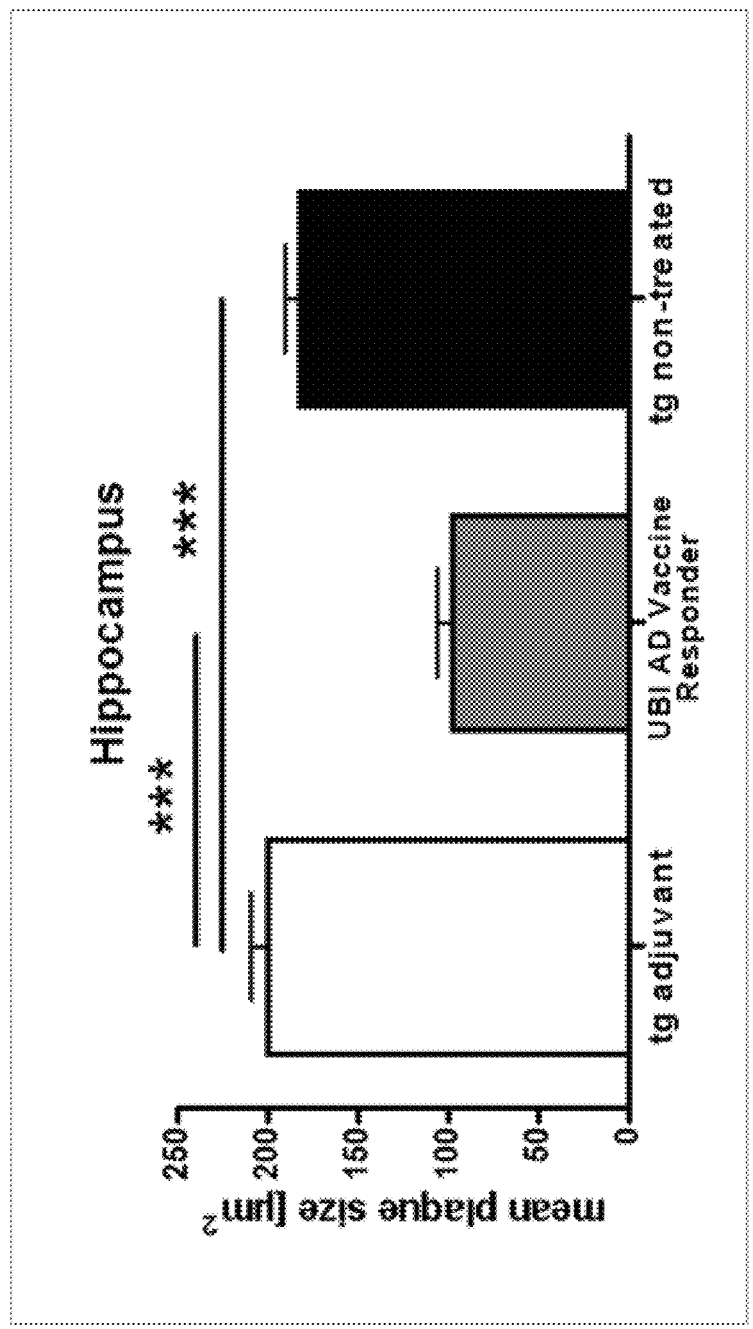
FIG. 10B: illustrates effect of UBI AD vaccine in a prevention mode on brain morphology of the hippocampus from young transgenic mice overexpressing hAPP751. Brain samples obtained from transgenic mice treated with adjuvant alone, Responders from mice treated with UBI AD vaccine, and the non-treated mice were analyzed for amyloid beta plaque load and found reduced number of plaques and "lower mean plaque size per um$^2$" in UBI AD treated Responder mice when compared to the untreated and those treated with adjuvant alone.

At the end of the in life study, at termination, mice were transcardially perfused with physiological (0.9%) saline, the brains were rapidly removed, hemisected, and prepared for further analysis. The left hemispheres were frozen and later analyzed as described in Section e below. The right hemispheres were immersion fixed in fresh 4% paraformaldehyde in PBS, pH 7.4 for one hour. The hemispheres were then transferred to a 15% sucrose solution for cryoprotection. The next day, brains were frozen on dry ice and stored at −80° C. until used for histological investigations. Cryostat sections (10 nm thickness) were stained with H&E, recorded and assessed for neuronal layer integrity and gross morphology. Cryocut tissue sections were evaluated using monoclonal antibody 4G8 (anti-Aβ$_{17-24}$) to determine Aβ deposition and plaque load in the cortex and hippocampus. The number of plaques and area covered by plaques were quantified and the mean value of nine tissue slices from 5 different layers across the sagittal brain of each animal built the statistically relevant value for an animal. Seven tg+ mice in the UBI AD vaccine treated group and seven tg+ mice in the untreated control group were evaluated. The results are expressed as the percent Aβ$_{1-28}$ plaque load of UBI AD vaccine treated (n=7) versus untreated (n=7) animals (FIGS. 10A, 10B) and represent the average relative plaque load detected in 9 tissue sections by immunohistochemistry. A comparison of the UBI AD vaccine responder tg+ mice versus the untreated animals are also included in the brain cortex (0.22% vs. 0.32%) and in the hippocampus (0.20% vs. 0.29%); reduced mean plaque load is noted in the highly responsive vaccine-treated animals.

e. Determination of Aβ$_{1-42}$ by Biochemical Fractionation of Brain Tissue

The animals were terminated and the brains were prepared as described in the section below. The left brain hemisphere was frozen separately and later the soluble fractions from four brain extractions were evaluated for Aβ$_{1-42}$ peptide levels using high sensitivity Aβ$_{1-42}$ ELISA kits for antigen detection manufactured by The GENETICS Company, Switzerland; the Aβ$_{1-42}$ levels were determined in comparison to the standard provided by the manufacturer. The results obtained in the four brain fractions are given as ng/g wet brain. The left-brain hemisphere (including the *bulbus olfactorius*) of each animal was extracted with TRIS-buffered saline (TB S), Triton X-100 detergent, SDS detergent, and formic acid (FA) for characterization and evaluation of Aβ$_{1-42}$ and the fractions were tested in duplicate. Briefly, the TBS extract contains the water-soluble Aβ$_{1-40}$ and Aβ$_{1-42}$ fraction of the brain tissue. To dissolve the remaining beta amyloid peptides, detergents and acids are necessary. Triton X-100 is an oligo-ethylene glycol derivative with two properties; the iso-octyl residue with the benzene ring destroys the apolaric van der Waal forces and the repeated —O—CH$_2$—CH$_2$— residues disintegrate hydrogen bonds. SDS has a similar two-sided effect but it is stronger and disrupts the entire secondary structure; the Aβ peptide will get linear and the peptide chain is stretched. Formic acid is the strongest solvent and disrupts mainly hydrogen bonds. It can be assumed that TBS solubilizes oligomeric structures. Triton solubilizes smaller polymers, like protofibrils. SDS disrupts the whole remaining structures and the remaining proportion comprising strongly complexed insoluble fibrils can be separated in FA, mainly as monomers. Therefore, to assess the beta amyloid polymerization status and the efficacy of an anti-amyloidogenic test compound all four fractions are investigated.

Figure 11A:
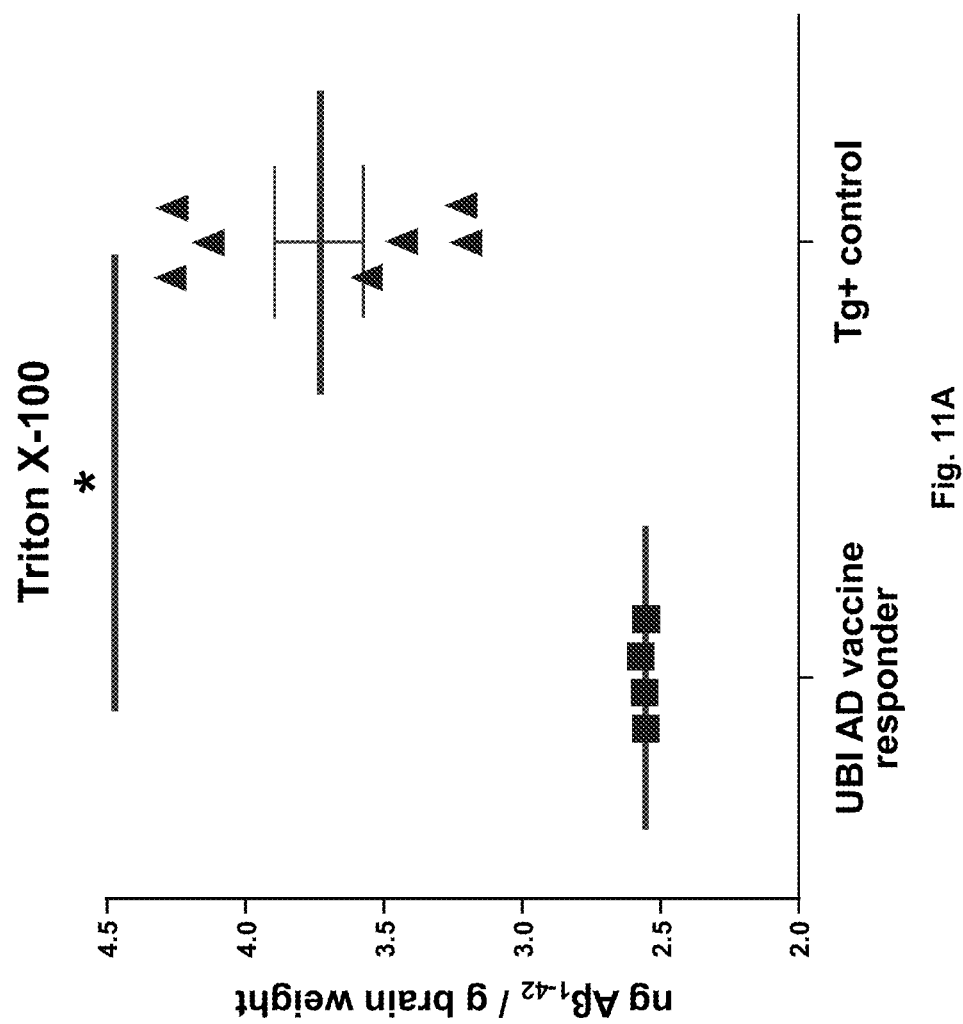
FIG. 11A: illustrates effect of UBI AD vaccine in a preventative mode on amyloid β-peptide ($A\beta_{1-42}$) concentration in brain tissue extracts from young transgenic mice overexpressing hAPP751. Small protofibrils were obtained from the Triton X-100 fraction of biochemical extractions of the brain tissues. Transgenic Responder mice treated with UBI AD vaccine were found to have far less protofibrils when compared to the brain tissue extractions resulting from the Triton X-100 fractions from untreated transgenic mice.
Figure 11B:
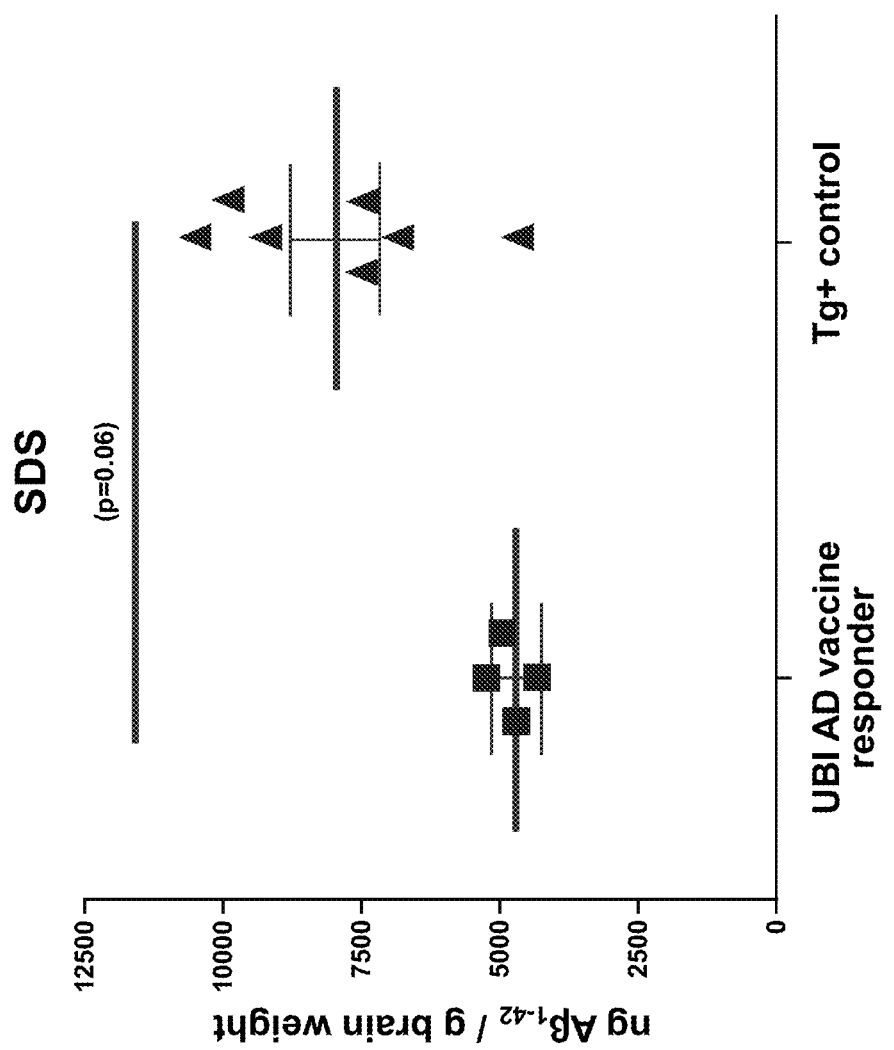
FIG. 11B: illustrates effect of UBI AD vaccine in a preventative mode on amyloid β-peptide ($A\beta_{1-42}$) concentration in brain tissue extracts from young transgenic mice overexpressing hAPP751. Large oligomers and fibrils were obtained from the SDS detergent fraction of biochemical extractions of the brain tissues. Transgenic Responder mice treated with UBI AD vaccine were found to have far less large oligomers and fibrils when compared to the brain tissue extractions resulting from SDS fractions from untreated transgenic mice.

The Aβ quantitative ELISA and the biochemical extractions test whether or not the anti-Aβ antibody response of the vaccine-treated (UBI AD vaccine) responder tg+ mice is associated with a reduced Aβ load when compared to the untreated tg+ mice. Of particular note is the reduced overall levels of Aβ$_{1-42}$ in the UBI AD vaccine responder tg+ mice when the Aβ$_{1-42}$ levels in each of the four biochemical extractions of brain tissue are compared to the results from the untreated tg+ control animals (FIGS. 11A, 11B).

f. Determination of Microglial Cell Activation

Cryocut tissue sections were evaluated for activated microglial cells using the CD11b antibody; the mean object size was evaluated as a quotient of the area through the number of objects in each slice as a mean measure of clustering of microglial cells; the mean value of 9 slices from 5 different layers across the sagittal brain of each animal built the statistically relevant value for an animal.

The results of vaccine-treated tg+ mice (n=7) versus non-treated tg+ mice (n=7), expressed as the percent of CD11b-positive cell areas stained in the brain cortex and hippocampus, showed that the treated animals have lower average percent areas stained when compared to the non-treated tg+ control animals. These results indicate that the vaccine-treated animals do not show increased numbers of activated microglial cells when compared with the untreated transgenic mice.

g. Determination of T-Cell-Infiltration in Brain Tissue

Cryocut tissue sections were evaluated to detect the number of T-cells in brain cortex, hippocampus and within blood vessels and cells were exclusively counted. The mean value of nine tissue slices from 5 different layers across the sagittal brain of each animal build the statistically relevant value for an animal. The results of vaccine-treated tg+ mice (n=7) versus non-treated tg+ control mice (n=7), expressed as the number of CD3-positive T-cells stained in brain cortex and hippocampus and the number of T-cells stained within blood vessels, indicate that the vaccine-treated animals show a slight decrease in the mean number of immunostained T-cells counted in the brain cortex, hippocampus and blood vessels when compared to the untreated tg+ control animals.

h. Conclusions

The hAPP751 transgenic mice were injected 3 or 4 times by intramuscular route over a 16 week period with the UBI AD vaccine or a placebo vaccine. The animals had good overall tolerability to the UBI AD vaccine, especially considering the high concentration of the UBI Aβ$_{1-14}$ peptide immunogen constructs given per dose (90 µg/150 µL) to these animals. In the responders, reduced Aβ plaque load and reduced Aβ$_{1-42}$ levels were noted in the 4 brain tissue extractions from these animals. The reduced Aβ deposition and plaques were also shown by immunohistochemistry. There was no evidence of microglial cell activation or T-cell infiltration in the brains of vaccine-treated tg+hAPP751 mice.

Example 14

Epitope Mapping of Antibody Response to UBI AD Vaccine for Safety

ELISA tests using plates coated with Aβ$_{1-14}$ (SEQ ID NO: 4), Aβ$_{1-28}$ (SEQ ID NO: 3), Aβ$_{17-42}$ (SEQ ID NO: 67), MvF5 Th (SEQ ID NO: 46), HBsAg3 Th (SEQ ID NO: 47) peptides as the solid-phase antigens were evaluated for the specificity of the antibody response to the UBI AD vaccine in the sera from the immunized guinea pigs and baboons. High titer anti-A3 antibodies evoked by the vaccine were detected with the $A\beta_{1-14}$ and $A\beta_{1-28}$ antigens (Table 1); however, there was concern that the $A\beta_{1-28}$ peptide was also detecting additional antibodies due to "B cell epitope spreading" beyond amino acid 14, a source of potentially adverse cross-reactivities.

To address this concern, hyperimmune guinea pig antisera and hyperimmune baboon antisera were also tested with $A\beta_{17-42}$ peptide by ELISA. The ELISA titers indicate that epitope spreading was not detected in the hyperimmune samples tested. The hyperimmune sera showed enhanced binding to the $A\beta_{1-28}$ peptide but did not react with $A\beta_{17-42}$. The hyperimmune sera did not react with either MvF5 Th (SEQ ID NO: 46) or HBsAg3 Th (SEQ ID NO: 47) peptide domains. In a fine epitope mapping method to localize the predominant antibody binding site(s) to specific residues within the target region, 24 overlapping 10-mer peptides were synthesized around the N-terminal aspartic acid residue "D" of the $A\beta_{1-14}$ peptide sequence and the adjacent region of the human amyloid-β peptide precursor protein (hAPP), to cover the entire length of $A\beta_{1-14}$ plus adjoining hAPP positions (Table 9). These nested peptides were used individually to coat microtiter wells as solid-phase immunoadsorbents for ELISA tests. The positive control ELISA plate was coated with $A\beta_{1-28}$. They were tested for antibody binding with the sera from the four immunized baboons, from weeks 0, 10, 84 and 111. Baboon sera were serially diluted and assayed on plates coated with a 10-mer peptide at 5 ug/mL. As expected, peptide (DAEFRHDSGY) with SEQ ID NO: 6 representing the N-terminus 10-mer of $A\beta_{1-14}$ (SEQ ID NO: 4) reacted strongly with immune sera from all four baboons. The "D" in position 1 of $A\beta_{1-14}$ was key to the antibody specificity. Deletion of "D" or modification of position 1 to "E" (glutamic acid) resulted in severely reduced binding to the 10-mer peptides, indicating the high specificity of the baboon antibodies for $A\beta_{1-10}$ (SEQ ID NO: 6) and the low likelihood for the occurrence of antibody recognition sites cross-reactive to the Aβ peptide immunogen constructs elsewhere on $A\beta_{1-42}$ peptide or its precursor. In addition, epitope mapping for fine specificity recognized by the immune sera was further confirmed by competitive inhibition ELISA as shown in Table 10. In sum, these antibody epitope findings demonstrated that the antibodies induced by the UBI AD immunotherapeutic vaccine candidate were directed specifically to the N-terminal domain of Aβ, not to sites beyond residue 14 and not to the MvF5 Th nor HBsAg 3 Th domains.

Example 15

Antibody Response and Aβ1-40 Levels in Serum and CSF from Cynomolgus Macaques Received Multiple Immunizations with UBI AD Vaccine The kinetics of the vaccine response showed that four of six macaques in the low dose Group 2 (150 µg per 0.25 mL) and all six macaques in the high dose Group 3 (750 µg per 1.25 mL) generated antibody against the $A\beta_{1-14}$ peptide immunogen constructs cross-reactive with $A\beta_{1-42}$ after the first immunization.

As shown in Table 11, both low dose and high dose animals sustained high titer antibody for the duration of the study (through week 27). The fine specificity of the antibody response through epitope mapping (Table 12) with sera from four macaques per group, immunized three times (9 WPI) and five times (15 WPI) with either high (750 µg) or low (150 µg) doses of the UBI AD vaccine indicated a strong specificity for N-terminal $A\beta_{1-10}$ peptide (DAEFRHDSGY) (SEQ ID NO: 6) in all four animals per group, similar to that observed with immune sera from the earlier baboon study (Table 9). Unlike the reactivity pattern observed in baboons, some modest reactivities were observed with all four animals for peptides with SEQ ID NOs: 20 to 22 surrounding residues RHD at positions 4, 5 and 6 of the N-terminus of the $A\beta_{1-42}$ peptide. No additional reactivities to other 10-mer peptides outside the four mentioned above are noted for any of the macaque samples tested.

The effects of UBI AD vaccine on $A\beta_{1-40}$ levels in sera and CSF were determined using commercially available immunoassay kits. As shown in Table 13, the concentration of $A\beta_{1-40}$ after vaccination was determined in serum at 0, 15, 21 and 25.5 weeks and in CSF at the time of sacrifice (week 15+1 day or week 27). The $A\beta_{1-40}$ levels in serum were elevated in macaques receiving the UBI AD vaccine but normal levels were noted in animals receiving the placebo vaccine. In contrast, $A\beta_{1-40}$ levels maintained a steady state in the cerebral spinal fluid (CSF) of macaques receiving either the placebo or UBIAD vaccine. These results support the "Peripheral Sink Hypothesis" as the action mode for anti-Aβ antibodies whereby the antibodies promote the efflux of Aβ peptides from the brain to the peripheral circulatory system.

Example 16

Cellular Immune Response from Cynomolgus Macaques Received Multiple Immunizations with UBI AD Vaccine Peripheral blood mononuclear cell (PBMC) samples were isolated from whole blood collected at 15, 21 and 25.5 weeks and then cultured in the presence of various Aβ peptides. As shown in Table 14, no proliferation responses by lymphocytes were observed when $A\beta_{1-14}$ peptide was added to culture medium. However, positive proliferation responses were noted when the $A\beta_{1-42}$ or $A\beta_{17-42}$ (SEQ ID NO: 67) peptide was added to some PBMC cultures.

The PBMC samples collected at 15, 21 and 25.5 weeks were also tested for cytokine secretion in the presence of Aβ peptides or PHA mitogen. As shown in Table 15, three cytokines (IL-2, IL-6, TNF-α) showed detectable secretion in response to the full-length $A\beta_{1-42}$ peptide but not to the $A\beta_{1-14}$ peptide; up-regulation of cytokine secretion was not detected in the UBI AD vaccine-treated samples when compared to the placebo vaccine samples. Three other cytokines (IL-10, IL-13, IFN-γ) tested in the presence of the Aβ peptides were below the assay detection limit in all PBMC cultures.

The macaques were immunized with the UBI AD vaccine having only the N-terminal $A\beta_{1-14}$ peptide immunogens with foreign T helper epitopes, without the $A\beta_{17-42}$ peptide domain, indicating that the positive proliferation results noted in the PBMC cultures in the presence of $A\beta_{1-42}$ peptide were not related to the UBI AD vaccine response, but rather were a background response to native Aβ.

These results support the safety of the UBI AD vaccine that has only $A\beta_{1-14}$ and foreign T helper epitopes, showing that it does not generate potentially inflammatory anti-self cell-mediated immune responses to Aβ peptides in the normal macaques. In contrast, the adverse events associated with encephalitis in the clinical trial studies of the AN-1792 vaccine were attributed in part, to the inclusion of T cell epitopes within the fibrillar/aggregated $A\beta_{1-42}$ immunogen of that vaccine.

Example 17

Comparison of Immunogencity of UBI AD Vaccine at Different Levels in Guinea Pigs, Macaques and Baboons After extensive testing of the various Aβ peptide immunogen constructs for their suitability as key ingredients of the AD vaccine, peptide constructs with SEQ ID NOs: 64 and 65 were selected to devise and design vaccine formulations. The selected vaccine formulation comprising the two peptide immunogen constructs forming immunostimulatory complexes with CpG oligomers and supplemented with mineral salts of ADJU-PHOS® (UBI AD vaccine), was tested extensively as described in Examples 8 to 15 to calibrate its immunogenicity in multiple species (guinea pigs, macaques, and baboons) and dosing regimes in preparation for its use in clinical trials. Table 16 summarizes the peptide dose vs responder rate (number of animals with positive titers/total number of animals tested) after one or two doses, and body weight of each species for assessment of the dosing schedules of the UBI AD vaccine. From the analysis, it is preferably to set the per dose level at higher than 100 μg, based on data from all species concerned, to arrive at a respectable response rate after single shot which, upon boost, would allow high or near full response rate. The 300 μg per 0.5 mL dose of UBI AD vaccine was selected for studies in human subjects. In the Phase I clinical studies, individuals were immunized at 0, 4, 12 weeks. Four weeks post one dose, 2 of 19 enrolled subjects had positive anti-Aβ antibody titers; four weeks post two doses at 8 weeks, 17 of 19 subjects were positive; and four week post three doses at 16 weeks, all 19 subjects were positive and remained positive to the end of the Phase I study at weeks 24-26.

Example 18

Phase I Clinical Trial Suggests Therapeutic Effect by UBI AD Vaccine (UB-311)

The Aβ peptide is a major therapeutic target in AD based on pathological, biochemical and genetic evidence that supports its role in the disease process. The goal for an active Aβ immunotherapy, such as UBI AD vaccine (UB-311), is to stimulate an immune response to generate robust anti-Aβ antibodies that captures excess Aβ peptides from circulation and prevents or slows cognitive decline.

The UB-311 phase I clinical trial entitled "A Phase I, Open-label Study to Evaluate the Safety, Tolerability and Immunogenicity of the UBI AD Immunotherapeutic Vaccine (UB-311) in Patients with Mild to Moderate Alzheimer's Disease" was conducted based on the approved final clinical protocol. A total of 19 patients with mild to moderate AD were enrolled. Each patient received three intramuscular injections of the study drug (UB-311) at weeks 0, 4 and 12. The total study duration was 24-26 weeks.

In addition to the evaluation of safety, tolerability, immunogenicity and efficacy data collected from the UB-311 phase I clinical trial, research analyses of antibody binding epitope, Aβ peptide levels, and immune functions of the study subjects for exploratory purposes are described. The results from blood collected before and after UB-311 immunization at weeks 0, 4, 8, 12, 16, and 24/26 for isolation of Peripheral Blood Mononuclear Cells (PBMC) and serum/plasma samples for serological and immunogenicity analyses include (1) anti-Aβ antibody titers, (2) epitope mapping, (3) plasma $Aβ_{1-40}$ levels, and (4) in vitro lymphocyte proliferation and cytokine analysis.

A total of 19 subjects with mild to moderate Alzheimer's disease (AD) were enrolled in the study and received three intramuscular injections of the UBI AD Immunotherapeutic Vaccine (UB-311) at weeks 0, 4 and 12.

UB-311 demonstrated satisfying safety and tolerability profiles when administered to patients with clinically documented mild to moderate AD. The incidence of adverse events (AEs), which were definitely, probably or possibly related to UB-311, was designed as a primary endpoint for evaluating the safety of UB-311 treatment. During the study period, 16 treatment-related AE episodes were reported in 9 of 19 subjects. Among treatment-related AEs were mild injection site reactions (5 subjects), moderate agitation (2 subjects), and mild red blood cell sedimentation rate increase (2 subjects). All treatment-related AEs were rated as grade 1 (mild) or 2 (moderate) in severity and no action was taken for these episodes. One subject with a medical history of ankylosing spondylitis and diabetes mellitus reported a serious adverse event (SAE) of herpes zoster during the follow-up period. The subject was immediately hospitalized at the occurrence of the event and appropriate treatments were provided. The SAE was judged as unlikely in causality and the subject was discharged from hospital two weeks later due to his improved condition.

The tolerability of UB-311 was assessed. All 19 subjects completed the treatment and none withdrew early from the study despite AE occurrences. The tolerability was thus 100%.

Example 19

Figure 12:
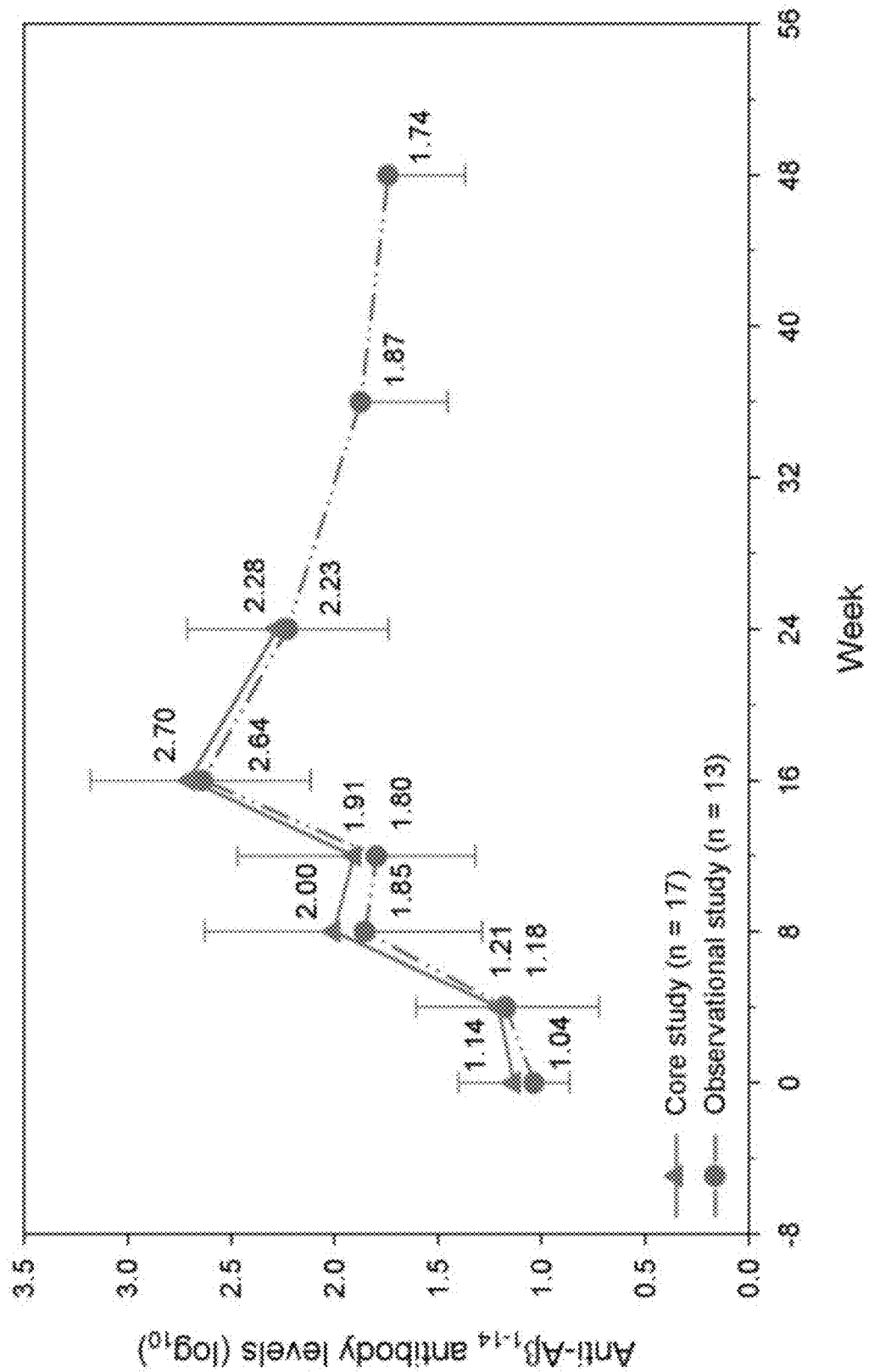
FIG. 12: illustrates mean anti-$A\beta_{1-14}$ antibody titers following UBI AD vaccine treatment in patients. Two sets of data were plotted with one from data obtained between weeks 0 and 24/26 (n=17, solid line) during the trial period and the other from data obtained including the follow-up observational period (n=13, dashed line) between weeks 0 and 48. The $A\beta_{1-14}$ antibody $\log_{10}$ titers decreased over time but remained positive in all subjects at the end of study (week 48).

Administration of UB-311 Vaccine Elicited Antibodies with Specificity to N-Terminus of $Aβ_{1-14}$ Domain in all Subjects As shown in FIG. 12, the change in anti-$Aβ_{1-14}$ antibody levels was measured at weeks 0, 4, 8, 12, 16 and 24-26 to evaluate the immunogenicity of UB-311 vaccine. The mean value of anti-$Aβ_{1-14}$ antibody levels transformed to $log_{10}$ for all subjects at week 0 (pre-treatment) was 1.14, slightly increased to 1.21 at week 4, increased markedly to 2.00 and 1.91 at weeks 8 and 12, peaked at 2.70 at week 16 (4 weeks post third immunization), and decreased to 2.28 at weeks 24-26.

The antibody titers were $Log_{10}$ transformed and their values at week 0 were used as the baseline. A comparable trend was observed for all three specific antibody titers. The mean value of change of antibody titers slightly increased at week 4, except for anti-$Aβ_{1-42}$ monomer antibodies, at the time when the subjects had already received the first dose of UB-311 at week 0, but prior to the second dose. The antibody titers also increased at week 8 after the second dose was given to subjects at week 4. After administration of the third dose at week 12, the peak mean change of antibody titers was detected at week 16.

Example 20

Figure 13:
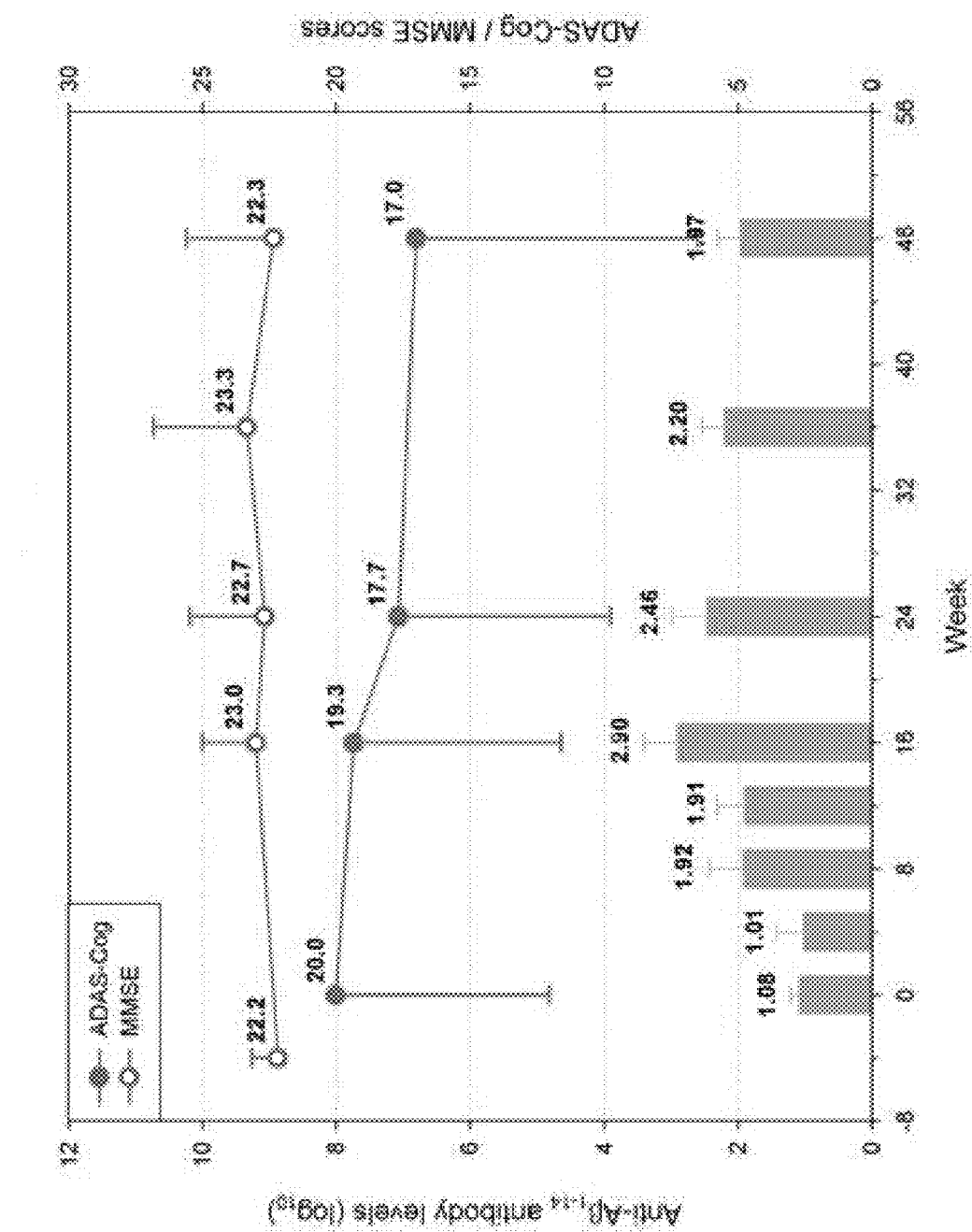
FIG. 13: illustrates mean ADAS-Cog (solid circle), MMSE (open circle) scores and anti-$A\beta_{1-14}$ antibody titers (solid bars) between weeks 0 and 48 in Subjects >60 years of age and with baseline MMSE score >20 undergoing the UBI AD vaccine trial.

Neurological, Cognitive and Functional Tests Assess Efficacy of UB-311 Vaccine in Mild to Moderate Alzheimer's Disease The efficacy of UB-311 was evaluated through measuring the changes of ADAS-Cog score, MMSE score, and ADCS- CGIC in 19 patients. The ADAS-Cog score and ADCS-CGIC were assessed at week 0 (V2), week 16 (V7) and weeks 24-26. The MMSE score was measured at prescreen (V1), week 16 and weeks 24-26. Among the subjects, increases of 1.42 and 0.79 in ADAS-Cog score were observed from week 0 to week 16 and from week 16 to weeks 24-26, respectively. The mean ADAS-Cog score at baseline was 26.26 among the subjects, increased to 27.68 at week 16 and slightly increased to 28.47 at weeks 24-26. Furthermore, reductions of 0.32 and 0.79 in MMSE score were found from prescreen visit to week 16 and from week 16 to weeks 24-26 (FIG. 13).

The mean MMSE score of the subjects at prescreen visit was 19.16. The score decreased to 18.84 at week 16, and to 18.05 at weeks 24-26 the last visit. Notably, despite the mean scores of the two scales altered, the distribution of the scores for individual subjects was quite dispersed, and therefore the trends of the two scales seemed to be stable.

As to the ADCS-CGOC rating, more than 35% of subjects demonstrated improvements at week 16, 4 weeks after the last treatment (third dose). These improvement rates decreased to no more than 18% in the patient population after a longer cessation of treatment at weeks 24-26. At week 16, slightly less than half of the subjects had no change in ADCS-CGIC, and this category of subjects increased mildly to more than 50% of the total subjects after another 8 to 10 weeks no-treatment follow-up period after week 16. Comparing subject proportion with improvement versus worsening, positive results were shown at week 16 in favor of the investigational product, but not at week 24-26 (12 weeks after last vaccine dose).

Figure 14:
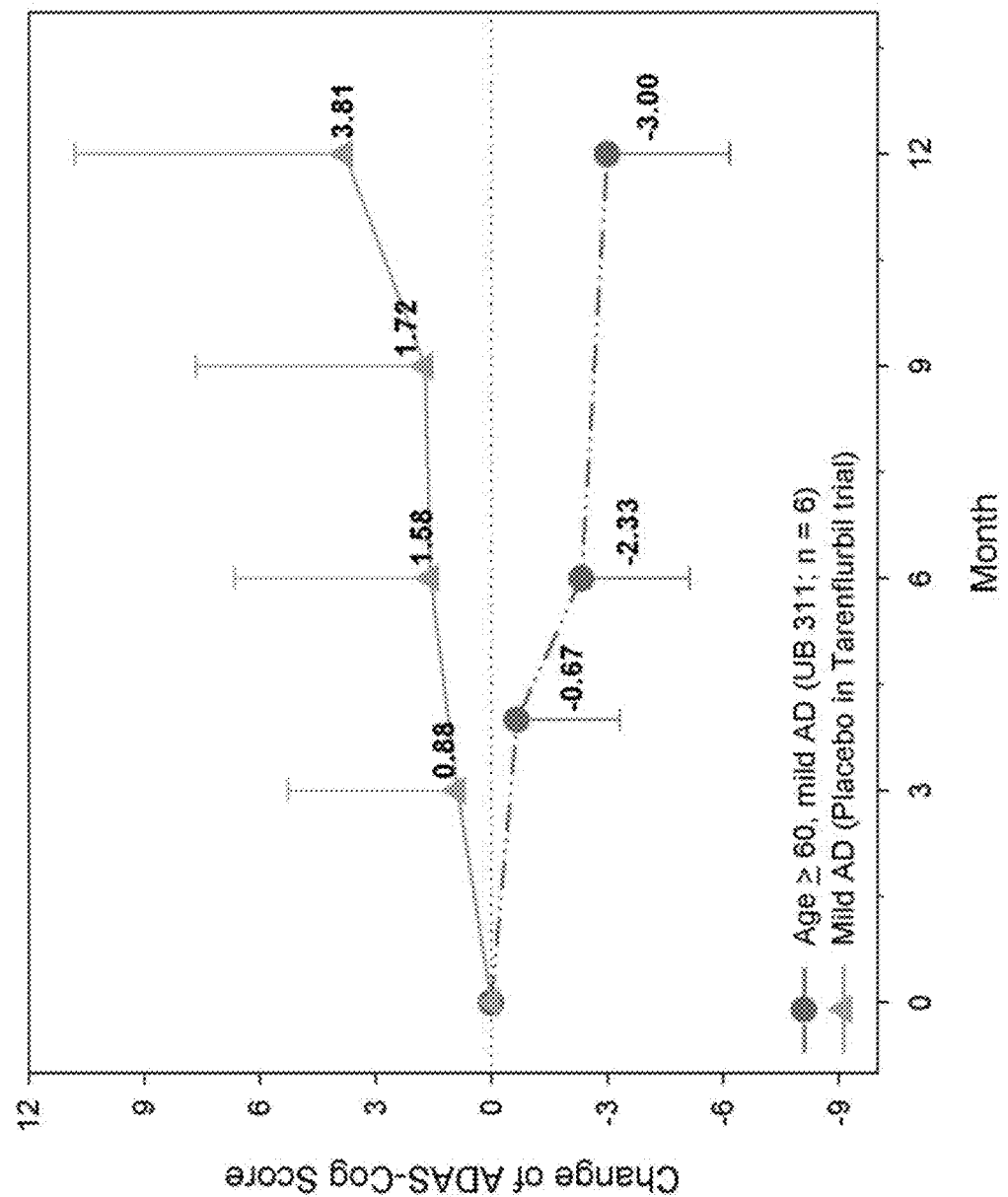
FIG. 14: illustrates a change in the mean ADAS-Cog scores over a 12-month period between UBI AD vaccinees with mild AD and older than 60 years of age (solid circle) and those from a placebo group with mild AD in a Tarenflurbil trial (solid triangle). Six subjects >60 years of age with mild AD showed improvement with decreased scores when evaluated at 4, 6, 12 months (−3.00 change) after immunization with UBI AD vaccine at weeks 0, 4, 12 in comparison to subjects with mild AD who received a placebo in the Tarenflurbil trial (Green et al., *JAMA* 2009; 302(23):257-2564) and showed a poor response with increased scores (3.81 change) over the same time period.

In the subgroup analyses, results demonstrated that older subjects with mild AD (aged>60 years and baseline MMSE>20) had a better response to the UB-311 vaccine by showing (1) a decrease of 3 points in mean ADAS-Cog (compared to an increase of 3.81 points in the placebo group from Tarenflurbil Phase II trial over a 12-month period), (2) a stable average MMSE score (compared to a decrease of 2.04 points in the placebo group from Tarenflurbil Phase II trial over a 12-month period), as shown in FIG. 14, and (3) a higher proportion with improvement and no rate change in ADCS-CGIC. Such improvement in three out of three cognition scores in patients with mild AD with age>60 years has never been reported and is most enthusiastically received.

Example 21

Enzyme Immunoassay (ELISA) for Detection of Human Antibodies to $A\beta_{1-28}$ Monomers, $A\beta_{1-42}$ Monomers or $A\beta_{1-42}$ Oligomers Study of Alzheimer's disease has demonstrated that Aβ aggregates and Aβ-derived oligomers play a central role in AD pathogenesis. Binding of Aβ oligomers to neurons expressing the N-methyl-D-aspartate (NMDA)-type glutamate receptor (NMDA-R) subunits NR1 and NR2B has been reported by Lacor P N in *Current Genomics* 2007; 8:486-508. When Aβ oligomers bind to NR1 and NR2B on hippocampal neuronal cells, this ligand-receptor binding results in significant decrease in the number of synaptic terminals, which is associated with memory and cognitive deficits and dementia. Recently, results of in vitro study in cells and clinical trials indicated that anti-Aβ oligomer antibodies are able to block this binding and protect neurons from Aβ oligomer toxicity. UBI AD vaccine (UB-311) contains two peptide immunogens each peptide includes a short N-terminal Aβ peptide ($A\beta_{1-14}$) synthetically linked to a different Th2-biased N-terminal peptide epitope. To evaluate the immunogenicity of the UBI AD vaccine response, an anti-Aβ antibody enzyme immunoassay (ELISA) test was developed for in vitro detection of antibodies to $A\beta_{1-28}$ monomers, $A\beta_{1-42}$ monomers and $A\beta_{1-42}$ oligomers.

The $A\beta_{1-28}$ monomers, $A\beta_{1-42}$ monomers or $A\beta_{1-42}$ oligomers were pre-coated onto the wells of microplates as immobile antigens. During the course of the assay, the serum sample was 1:10 serially diluted from 1:100 to 1:100,000 and added to the pre-coated microplates. The anti-$A\beta_{1-28}$, anti-$A\beta_{1-42}$ monomer or oligomer antibodies, if present, bind to the immobile antigens. After washing the wells to remove unbound antibodies and other serum components, a standardized preparation of horseradish peroxidase-conjugated recombinant protein A/G was added to each well and allowed to react with bound antibodies. The unbound conjugate was removed by washing the wells and a substrate solution containing 3,3',5,5'-tetramethylbenzidine (TMB) and hydrogen peroxide was added to each well. A yellow color developed in proportion to the amount of Aβ-specific antibodies present, if any, in the serum samples tested. The enzyme-substrate reaction was terminated by the addition of a diluted sulfuric acid solution. The color changes that occur in each well were then determined by spectrophotometric measurement of Absorbance in a microplate reader at a wavelength of 450 nm ($A_{450}$). UBI® ELISA Titer calculation program was used to calculate the relative antibody titer.

Figure 15A:
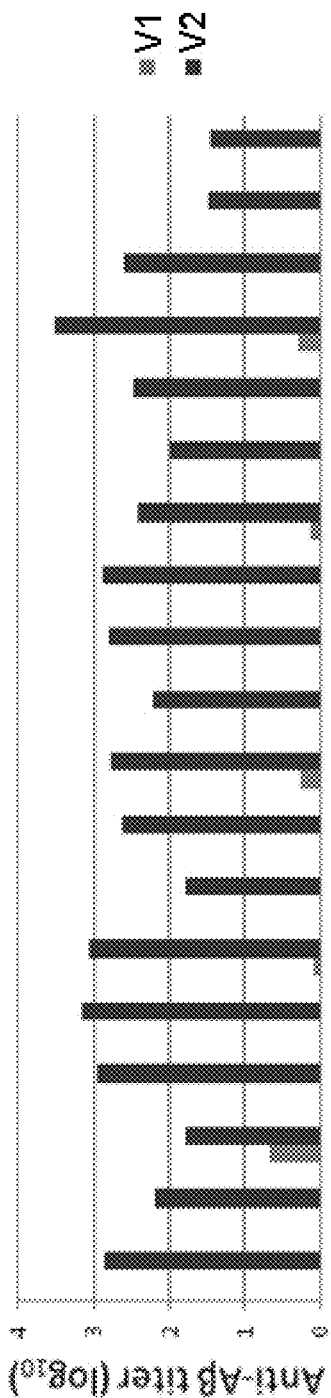
FIG. 15A: illustrates immunogenicity study in Patients receiving UBI AD vaccine in a Phase I Clinical Trial. Serum samples from all 19 individuals with mild to moderate Alzheimer's disease were evaluated pre-treatment (V1/V2; light gray bars) and post-immunization at week 16 (V7; black bars) for anti-Aβ antibodies. Antibody titers ($\log_{10}$) to the $A\beta_{1-28}$ monomer were evaluated by ELISA test using serum samples collected at pre-treatment visit and week 16, 4 weeks after the last of three vaccinations of UBI AD vaccine delivered at 0, 4, and 12 weeks. Little or no antibody reactivity was found in pre-treatment samples (thus seeing no bars in most of the paired data comparison). All individuals generated high titer anti-Aβ antibodies after treatment to the $A\beta_{1-28}$ monomer that are localized at the N-terminus of Aβ peptide as illustrated in FIG. 16.
Figure 15B:
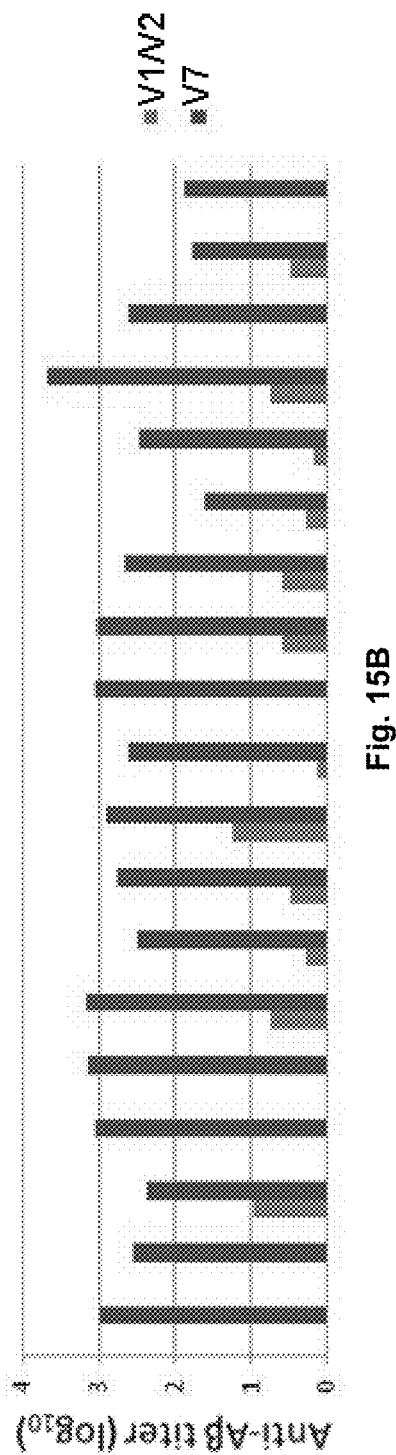
FIG. 15B: illustrates immunogenicity study in Patients receiving UBI AD vaccine in a Phase I Clinical Trial. Serum samples from all 19 individuals with mild to moderate Alzheimer's disease were evaluated pre-treatment (V1/V2; light gray bars) and post-immunization at week 16 (V7; black bars) for anti-Aβ antibodies. Antibody titers ($\log_{10}$) to the $A\beta_{1-42}$ monomer were evaluated by ELISA test using serum samples collected at pre-treatment visit and week 16, 4 weeks after the last of three vaccinations of UBI AD vaccine delivered at 0, 4, and 12 weeks. Little or no antibody reactivity was found in pre-treatment samples (thus seeing no bars in most of the paired data comparison). All individuals generated high titer anti-Aβ antibodies after treatment to the $A\beta_{1-42}$ monomer that are localized at the N-terminus of Aβ peptide as illustrated in FIG. 16.
Figure 15C:
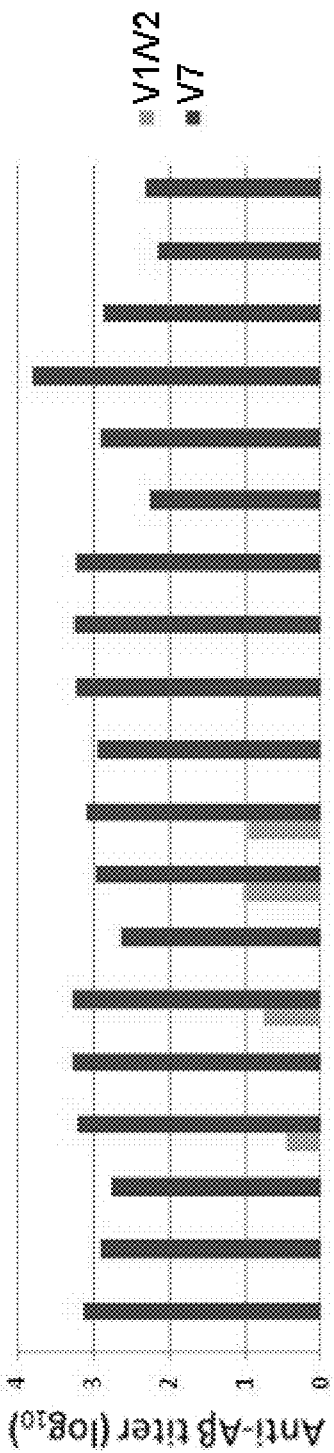
FIG. 15C: illustrates immunogenicity study in Patients receiving UBI AD vaccine in a Phase I Clinical Trial. Serum samples from all 19 individuals with mild to moderate Alzheimer's disease were evaluated pre-treatment (V1/V2; light gray bars) and post-immunization at week 16 (V7; black bars) for anti-Aβ antibodies. Antibody titers ($\log_{10}$) to the $A\beta_{1-42}$ oligomers were evaluated by ELISA test using serum samples collected at pre-treatment visit and week 16, 4 weeks after the last of three vaccinations of UBI AD vaccine delivered at 0, 4, and 12 weeks. Little or no antibody reactivity was found in pre-treatment samples (thus seeing no bars in most of the paired data comparison). All individuals generated high titer anti-Aβ antibodies after treatment to the $A\beta_{1-42}$ oligomers that are localized at the N-terminus of Aβ peptide as illustrated in FIG. 16.

Aβ oligomers are shown to be most toxic to neurons compared to Aβ monomers or amyloid plaques. The goal for active immunotherapy is not only to induce production of antibodies specific for Aβ monomers but also for Aβ oligomers. Serum samples collected from 19 patients with mild to moderate AD at weeks 0 (baseline), 4, and 12 before each UB 311 injection and at weeks 8, 16 and 24 were analyzed for anti-Aβ antibody titers. FIG. 15 depicts the antibody titers of anti-$A\beta_{1-28}$ monomer, anti-$A\beta_{1-42}$ monomer and anti-$A\beta_{1-42}$ oligomer at screening visit (V1/V2) and at week 16 (V7), four weeks after the last UB-311 immunization for each of the 19 enrolled subjects.

Example 22

Epitope Mapping: Competitive Binding Inhibition Enzyme Immunoassay (EIA) for Detection of Human Antibodies to the N-Terminal Peptide Epitope mapping was used to identify the binding sites or epitopes of anti-$A\beta_{1-14}$ antibodies on linear, overlapping 10-mer amino acid sequences of Aβ peptide (between residues −9 and 24 on Aβ) by ELISA tests. Clinical serum samples from the 19 subjects were evaluated. Results at week 16, after 3 immunizations at 0, 4 and 12 weeks, are shown below (FIG. 16).

Synthetic $A\beta_{1-28}$ peptide was chosen as an immobile antigen and pre-coated at the concentration of 2 μg/mL onto the wells of microplates. Before the experiment, each serum sample was diluted at 1:50, 1:100, 1:200 and 1:400 and tested to determine the optimal dilution. The optimally diluted anti-Aβ serum samples were mixed with designed 10-mer peptides individually as a liquid phase immunosorbent. The mixture was diluted 1:5 serially with optimal diluted serum prior to transfer to an $A\beta_{1-28}$ pre-coated plate. The optimally diluted anti-Aβ serum alone was used as a control. During the course of the assay, 10-mer peptides specifically bound to predominant antibody binding site, and competitively inhibited the binding of anti-Aβ antibody and the immobile antigen. After washing the wells to remove unbound antibodies and other serum components, a standardized preparation of horseradish peroxidase-conjugated recombinant protein A/G was added to each well and allowed to react with bound antibodies. After washing the wells to remove unbound conjugate, a substrate solution containing hydrogen peroxide and 3,3',5,5'-tetramethylbenzidine (TMB) was added to each well. A yellow color developed in proportion to the amount of Aβ-specific antibodies present, if any, in the serum samples tested. The enzyme-substrate reaction was terminated by the addition of a diluted sulfuric acid solution. The color changes that occur in each well were then measured spectrophotometrically in a microplate reader at the wavelength of 450 nm ($A_{450}$) by using $IC_{50}$ 5× program (Molecular devices). The binding of anti-Aβ antibodies and the immobile antigen in control well represented the maximal binding (100%) and the half maximal inhibitory concentration ($IC_{50}$) of 10-mer peptide was used as an indication of epitope specificity.

Example 23

Figure 16:
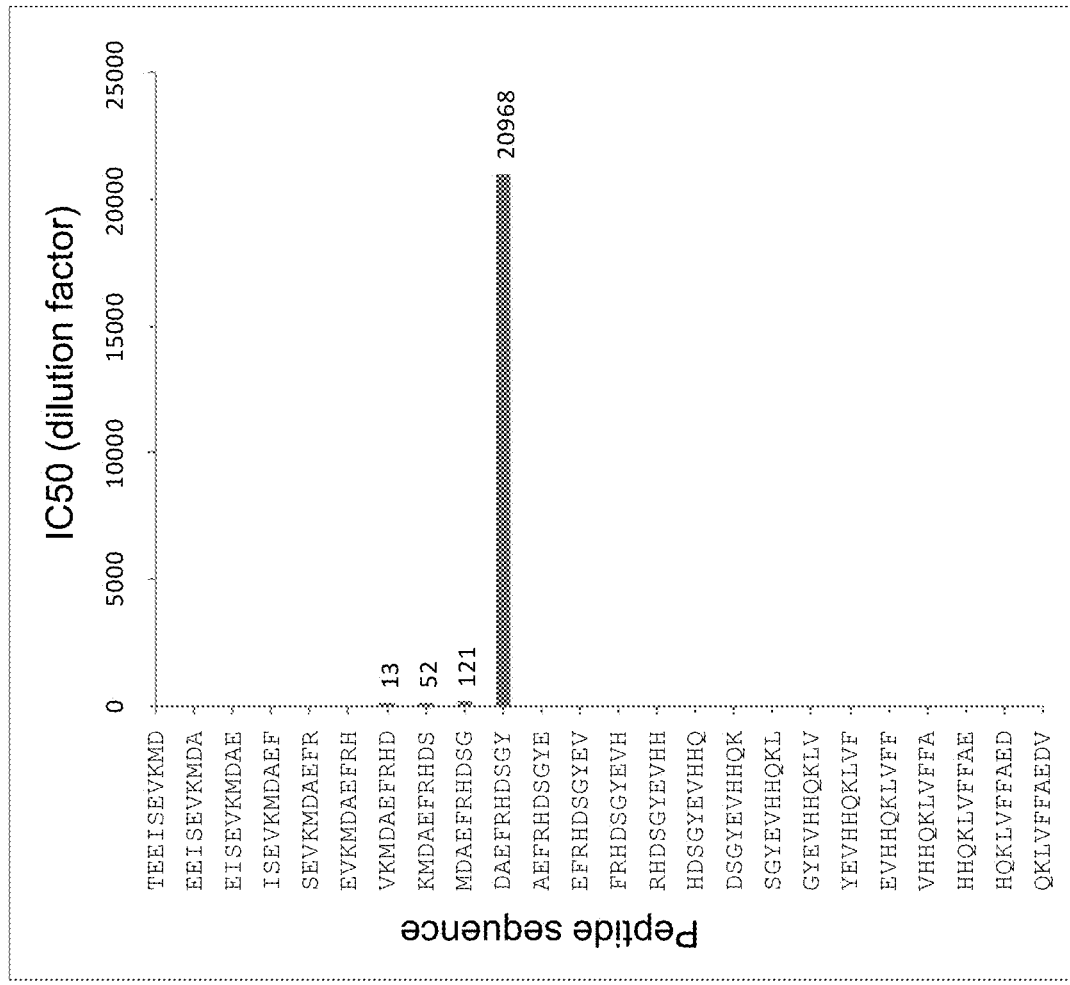
FIG. 16: illustrates epitope Mapping for Fine Specificity Analysis at the N-terminus of $A\beta_{1-42}$ by sera from immunized patients with Alzheimer's disease. The predominant epitope recognized by antibodies in the serum samples collected at week 16 from patients immunized with UBI AD vaccine is specific to the $A\beta_{1-10}$ peptide. This graph represents a typical positive epitope-mapping response from one individual (P210) who received three doses of UBI AD vaccine and generated an anti-Aβ antibody $\log_{10}$ titer of 2.198 to $A\beta_{1-14}$ peptide. Serum was diluted 1:50 for epitope mapping. Peak height indicates the half maximal inhibitory concentration ($IC_{50}$) of the subject's sample to different 10-mer Aβ peptides (SEQ ID NOs: 6, 8 to 30). A single major peak is observed, corresponding to immunoreactivity highly specific to the amino-terminal Aβ sequence, SEQ ID NO: 6 ($A\beta_{1-10}$: DAEFRHDSGY).

Predominant Epitope Recognized by Antibodies in Serum Samples from UB-311 Immunized Patients was Specific to the $Aβ_{1-10}$ Peptide In a fine epitope mapping method to localize the predominant antibody binding sites to specific residues within the target region (Table 17), 24 overlapping 10-mer peptides (SEQ ID NOs: 6, 8 to 30) were synthesized along the $Aβ_{1-14}$ peptide sequence (SEQ ID No 4) and the adjacent region of the human amyloid-β precursor protein (hAPP), to cover the entire length of $Aβ_{1-14}$ starting at N-terminal aspartic acid residue "D" plus the adjoining hAPP positions (FIG. 16). The serum samples collected from the 19 subjects were tested before immunization and at week 16 after receiving three doses of UB-311. The pretreatment samples were at baseline anti-Aβ antibody levels (data not shown). As expected, the predominant antibody response in all of the 19 samples for which positive epitope maps were generated was directed to the free amino terminus of Aβ (SEQ ID No 6), as shown in FIG. 16 and Table 17. More specifically, peptide DAEFRHDSGY, representing the N-terminus 10-mer of $Aβ_{1-14}$, reacted most strongly with immunized sera from all 19 patients. Additional antibody responses with weak reactivity to other Aβ 10-mer peptides were detected in 8 of the 19 subjects. The serum samples collected at weeks 4, 8, 12 and 24-26 from some but not all subjects were also tested and showed consistent results (data not shown). In summary, these data demonstrate that the majority of antibodies induced by UB-311 were directed specifically to the N-terminal domain of Aβ, and not to the sites beyond residue 14.

Example 24

$Aβ_{1-40}$ Peptide Elevated in Plasma after Three Immunizations of UBI AD Vaccine (UB-311)

At present, the change in plasma concentration of $Aβ_{1-40}$ (SEQ ID NO: 2), $Aβ_{1-42}$ (SEQ ID No: 1), or the $Aβ_{1-42}$:$Aβ_{1-40}$ ratio has not been found significantly associated with treatment response either in the setting of clinical trials of disease-modifying treatments or in patients with AD treated with cholinesterase inhibitors. Nevertheless, plasma Aβ levels have been proposed as a possible biomarker of AD.

In our previous study, the $Aβ_{1-40}$ levels in serum were elevated in macaques receiving the UBI AD vaccine but normal levels were noted in animals receiving the placebo vaccine. These results indicated that the "Peripheral Sink Hypothesis" might be the action mode for anti-Aβ antibodies. This phenomenon was also observed in the present study although the anti-Aβ antibody titers were much higher in the macaques after six UB-311 immunizations than the antibody titers in human subjects after three immunizations. As shown in Table 18, the plasma $Aβ_{1-40}$ levels of 12 paired cases with $Aβ_{1-40}$ plasma samples tested before UB-311 treatment and at week 16 (four weeks after the third immunization) were compared to the serum $Aβ_{1-28}$ antibody concentrations at week 16. All antibody titers were negative before UB-311 immunization. Eight individuals with anti-$Aβ_{1-28}$ antibody titers above $log_{10}$ 2.4 had elevated $Aβ_{1-40}$ titers after receiving the UBI AD Vaccine (UB-311); whereas, three of 4 individuals with antibody levels below $log_{10}$ 2.0 were not elevated post-treatment. The increased $Aβ_{1-40}$ levels were small in most cases, with one exception (Subject P109), which showed an unusually high $Aβ_{1-40}$ level in plasma before immunization and a significantly higher level (1031.9 pg/mL) after immunization. The reason for the very high $Aβ_{1-40}$ remains unclear. None of the subjects had measurable levels of $Aβ_{1-42}$ peptide in the plasma.

Example 25

UB-311 Immunization does not Stimulate Human Lymphocytes (PBMC) in the Presence of $Aβ_{1-14}$ or $Aβ_{1-42}$ Peptides The advent of new vaccines and the increasing number of highly publicized reports that claim a link between certain immunizations and autoimmune disease have led to the public concern over the risk of immunization. Lymphocyte proliferation and cytokine production in response to antigen stimulation can be used to assess whether the immune system is hyper-activated following a vaccination, and which pathway(s), if any, to be involved. The purpose of the present study was to evaluate the safety of the immunogen ($Aβ_{1-14}$) of UB-311 by measuring the Stimulation Index (SI) of lymphocyte proliferation in the absence or presence of Aβ peptides or PHA mitogen as positive control as well as the cytokine concentration in cultured lymphocytes from patients with AD before and after three UB 311 immunizations at week 16.

Peripheral blood mononuclear cells (PBMC) from patients with AD were isolated by Ficoll-hypaque gradient centrifugation. For peptide-induced proliferation and cytokine production, cells ($2.5×10^5$ per well) were cultured in triplicate alone or with individual peptide domains added (at a final concentration of 10 μg/mL), including $Aβ_{1-14}$ (SEQ ID NO: 4), $Aβ_{1-16}$ (SEQ ID NO: not included), $Aβ_{1-28}$ (SEQ ID NO: 3), $Aβ_{17-42}$ (SEQ ID NO: not included), $Aβ_{1-42}$ (SEQ ID NO: 1) and a non-relevant 38-mer peptide (p1412). Cultures were incubated at 37° C. with 5% $CO_2$ for 72 hours, and then 100 μL of supernatant was removed from each well and frozen at −70° C. for cytokine analysis. Ten μL of culture medium containing 0.5 μCi of $^3$H-thymidine ($^3$H-TdR, Amersham, Cat No. TRK637) was added to each well and incubated for 18 hr, followed by detection of radioisotope incorporation by liquid scintillation counting. The mitogen phytohemagglutinin (PHA) was used as a positive control for lymphocyte proliferation. Cells cultured alone without Aβ peptide or PHA mitogen were used as the negative and positive controls. The stimulation index (SI) was calculated as mean counts per min (cpm) of triplicate experimental cultures with Aβ peptide divided by mean cpm of triplicate negative control cultures; a SI>3.0 was considered a significant proliferation response.

Peripheral blood mononuclear cell samples were isolated from whole blood collected at week 0 (baseline) and week 16 (4 weeks after the third dose) and then cultured in the absence or presence of various Aβ peptides. As shown in Table 19, no significant proliferation response by lymphocytes was observed when Aβ$_{1-14}$, other Aβ peptides or p1412 (a non-relevant control peptide) were added to the culture medium. As expected, positive proliferation responses were noted when PHA mitogen was added to culture medium. The observation of similar responses to PHA before and after UB 311 immunization (p=0.87) suggests no significant alteration in study subjects' immune functions (Table 19).

Example 26

UB-311 Immunization does not Stimulate Human Cytokines in the Presence of Aβ$_{1-14}$ Peptide Cytokine analyses (IL-2, IL-6, IL-10, TNF-α, IFN-γ) from the PBMC cultures were performed on aliquots of culture medium with cells alone or in the presence of Aβ peptide domains or PHA. Human-specific cytokine sandwich ELISA kits (U-CyTech Biosciences, Utrecht, The Netherlands) were used to determine the concentrations (pg/mL) of individual cytokines following the manufacturer's instructions. The PBMC samples collected at week 0 and week 16 were also tested for cytokine secretion either with cells alone (negative control) or in the presence of Aβ peptides, p1412 (non-relevant peptide) or PHA mitogen (positive control) after being cultured for 3 days. The quantifiable range of the kit is between 5 and 320 pg/mL. Any measured concentration below 5 pg/mL or above 320 pg/mL was indicated as below quantification limit (BQL) or above quantification limit (AQL), respectively. However, for statistical considerations, BQL or AQL was replaced with the lower (5 pg/mL) or upper (320 pg/mL) quantifiable limit, respectively. The mean concentrations of each cytokine at week 0 and week 16 are shown in Table 20. As expected, there were significant increases in cytokine production in the presence of PHA, the positive control, except for IL-2. The production of cytokines in response to the stimulation with Aβ$_{1-14}$, or other Aβ peptides was observed at baseline (week 0) and week 16, but most values appeared similar to the corresponding negative controls (cells alone).

In order to assess the change of cell-mediated immune response after immunization, the change of mean cytokine concentrations from baseline to week 16 was compared with that of the negative controls and examined by paired Wilcoxon signed-rank test. Four cytokines (IFN-γ, IL-6, IL-10, TNF-α) showed notable increase in secretion in response to full-length Aβ$_{1-42}$ peptide; this observation may be due to the conformational epitopes of Aβ$_{1-42}$ aggregates. Up-regulation of cytokine secretion was not detected in Aβ$_{1-14}$ or other Aβ peptides.

Summary: UBI AD vaccine contains two peptide immunogens each with a free N-terminal Aβ$_{1-14}$ peptide synthetically linked to MvF5 Th and HBsAg3 Th epitopes respectively. In vitro lymphocyte proliferation and cytokine analysis were used to evaluate the impact of immunization of UBI AD vaccine on the cellular immune response. No proliferation responses by lymphocytes were observed when the Aβ$_{1-14}$ peptide or any other Aβ peptides was added to culture medium as shown in Table 19. Up-regulation of cytokine secretion by lymphocytes of UBI AD vaccine-immunized patients was not detected upon treatment with the Aβ$_{1-14}$ and other Aβ peptides except for Aβ$_{1-42}$, which elicited appreciable increase of four cytokines (IFN-γ, IL-6, IL-10, TNF-α) after UB 311 immunization at week 16 when compared to week 0 levels before treatment (Table 20). The increase of cytokine release through Th2 type T cell response is more likely unrelated to the UBI AD vaccine response since no up-regulation detected with Aβ$_{1-14}$ alone. The response to Aβ$_{1-42}$ is suspected to be a background response to native A3 that may be related to native T helper epitopes identified on Aβ$_{1-42}$. The lack of IL-2 production in response to PHA was observed, which is consistent with the findings reported by Katial R K, et al. in *Clin Diagn Lab Immunol* 1998; 5:78-81, under similar experimental conditions with normal human PBMC. In conclusion, these results showed that the UBI AD vaccine did not generate potentially inflammatory anti-self, cell-mediated immune responses in patients with mild to moderate Alzheimer's disease who participated in the phase I clinical trial, thus further demonstrating the safety of the UBI AD Vaccine (UB-311).

TABLE 1

Aβ$_{1-42}$ Peptide and Segments Thereof Employed in Serological Assays

| Amino Acid positions within Aβ$_{1-42}$ or APP | SEQ ID NO: | Sequence |
|---|---|---|
| Aβ$_{1-42}$ or APP 770 (D672-A713) | 1 | DAEFR HDSGY EVHHQ KLVFF AEDVG SNKGA IIGLM VGGVV IA |
| Aβ$_{1-40}$ or APP 770 (D672-V711) | 2 | DAEFR HDSGY EVHHQ KLVFF AEDVG SNKGA IIGLM VGGVV |
| Aβ$_{1-28}$ or APP 770 (D672-K699) | 3 | DAEFR HDSGY EVHHQ KLVFF AEDVG SNK |
| A4$_{1-14}$ or APP 770 (D672-H685) | 4 | DAEFR HDSGY EVHH |
| Aβ$_{1-12}$ or APP 770 (D672-Y683) | 5 | DAEFR HDSGY EV |
| Aβ$_{1-10}$ or APP 770 (D672-Y681) | 6 | DAEFR HDSGY |
| Aβ$_{15-42}$ or APP 770 (Q686-A711) | 7 | QKLVF AEDV GSNKG AIIGL MVGGV VIA |
| Aβ$_{-9-1}$ or APP 770 (T663-D672) | 8 | TEEIS EVKMD |
| Aβ$_{-8-2}$ or APP 770 (E664-A673) | 9 | EEISE VKMDA |
| Aβ$_{-7-3}$ or APP 770 (E665-E674) | 10 | EISEV KMDAE |
| Aβ$_{-6-4}$ or APP 770 (I666-F675) | 11 | ISEVK MDAEF |

TABLE 1-continued

Aβ$_{1-42}$ Peptide and Segments Thereof Employed in Serological Assays

| Amino Acid positions within Aβ$_{1-42}$ or APP | SEQ ID NO: | Sequence |
|---|---|---|
| Aβ$_{-5-5}$ or APP 770 (S667-R676) | 12 | SEVKM DAEFR |
| Aβ$_{-4-6}$ or APP 770 (E668-H677) | 13 | EVKMD AEFRH |
| Aβ$_{-3-7}$ or APP 770 (V669-D678) | 14 | VKMDA EFRHD |
| Aβ$_{-2-8}$ or APP 770 (K670-S679) | 15 | KMDAE FRHDS |
| Aβ$_{-1-9}$ or APP 770 (M671-R680) | 16 | MDAEF RHDSG |
| Aβ$_{1-10}$ or APP 770 (D672-Y681) | 6 | DAEFR HDSGY |
| Aβ$_{2-11}$ or APP 770 (A673-E682) | 17 | AEFRH DSGYE |
| Aβ$_{3-12}$ or APP 770 (E674-V683) | 18 | EFRHD SGYEV |
| Aβ$_{4-13}$ or APP 770 (F675-H684) | 19 | FRHDS GYEVH |
| Aβ$_{5-14}$ or APP 770 (R676-H685) | 20 | RHDSG YEVHH |
| Aβ$_{6-15}$ or APP 770 (H677-Q686) | 21 | HDSGY EVHHQ |
| Aβ$_{7-16}$ or APP 770 (D678-K687) | 22 | DSGYE VHHQK |
| Aβ$_{8-17}$ or APP 770 (S679-L688) | 23 | SGYEV HHQKL |
| Aβ$_{9-18}$ or APP 770 (G680-V689) | 24 | GYEVH HQKLV |
| Aβ$_{10-19}$ or APP 770 (Y681-F690) | 25 | YEVHH QKLVF |
| Aβ$_{11-20}$ or APP 770 (E682-F691) | 26 | EVHHQ KLVFF |
| Aβ$_{12-21}$ or APP 770 (V683-A692) | 27 | VHHQK LVFFA |
| Aβ$_{13-22}$ or APP 770 (H684-E693) | 28 | HHQKL VFFAE |
| Aβ$_{14-23}$ or APP 770 (H685-D694) | 29 | HQKLV FFAED |
| Aβ$_{15-24}$ or APP 770 (Q686-V695) | 30 | QKLVF FAEDV |
| Aβ$_{16-22}$ or APP 770 (D687-E693) | 31 | KLVFFAE |
| Spacer A | 32 | εK-KKK |
| Aβ$_{1-16}$ or APP 770 (D672-K687) | 66 | DAEFR HDSGY EVHHQ K |
| Aβ$_{17-42}$ or APP 770 (L688-A713) | 67 | LVFF AEDVG SNKGA IIGLM VGGVV IA |

TABLE 2

Selected Promiscuous T Helper Epitopes for Employment in the Design of Aβ$_{1-42}$ Derived Peptide Immunogen Constructs

| Description | SEQ ID NO: | Sequence |
|---|---|---|

TABLE 2-continued

Selected Promiscuous T Helper Epitopes for Employment in the Design of Aβ$_{1-42}$ Derived Peptide Immunogen Constructs

| Description | SEQ ID NO: | Sequence |
|---|---|---|
| HBsAg1 Th | 43 | KKKLFLLTKLLTLPQSLD<br>   RRRIKII RII I L IR<br>     VRVV  VV V I V<br>     F FF   FF F V F<br>               F |
| MvF4 Th | 44 | ISISEIKGVIVHKIETILF<br> T   RT    TR |
| HBsAg2 Th | 45 | KKKIITITRIITIPQSLD<br>      FFLL   L  ITTI |
| MvF5 Th | 46 | ISITEIKGVIVHRIETILF |
| HBsAg3 Th | 47 | KKKIITITRIITIITTID |

TABLE 3

Immunogenicity Enhancement of Aβ$_{1-14}$ peptide by Pathogen Protein derived Th epitopes including Idealized Artificial Th epitopes for Elicitation of Specific Antibodies towards the N-terminus of the Aβ$_{1-42}$ peptide in the Design of Aβ Peptide Immunogen Constructs

| Description | SEQ ID NO: | Sequence |
|---|---|---|
| Aβ$_{1-14}$-εK-*Clostridium tetani*1 Th | 48 | DAEFRHDSGYEVHH-εK-KKQYIKANSKFIGITEL |
| Aβ$_{1-10}$-εK-MvF1 Th | 49 | DAEFRHDSGY-εK-LSEIKGVIVHRLEGV |
| Aβ$_{1-12}$-εK-MvF1 Th | 50 | DAEFRHDSGYEV-εK-LSEIKGVIVHRLEGV |
| Aβ$_{1-14}$-εK-MvF1 Th | 51 | DAEFRHDSGYEVHH-εK-LSEIKGVIVHRLEGV |
| Aβ$_{1-14}$-εK-*Bordetella pertussis* Th | 52 | DAEFRHDSGYEVHH-εK-GAYARCPNGTRALTVAELRGNAEL |
| Aβ$_{1-14}$-εK-*Clostridium tetani*2 Th | 53 | DAEFRHDSGYEVHH-εK-WVRDIIDDFTNESSQKT |
| Aβ$_{1-14}$-εK-Diphtheria Th | 54 | DAEFRHDSGYEVHH-εK-DSETADNLEKTVAALSILPGHGC |
| Aβ$_{1-14}$-εK-*Plasmodium falciparum* Th | 55 | DAEFRHDSGYEVHH-εK-DHEKKHAKMEKASSVENVVNS |
| Aβ$_{1-14}$-εK-*Schistosoma mansoni* Th | 56 | DAEFRHDSGYEVHH-εK-KWFKTNAPNGVDEKHRH |
| Aβ$_{1-14}$-εK-Cholera Toxin Th | 57 | DAEFRHDSGYEVHH-εK-ALNIWDRFDVFCTLGATTGYLKGNS |
| Aβ$_{1-14}$-εK-MvF2 Th | 58 | DAEFRHDSGYEVHH-εK-ISEIKGVIVHKIEGI |
| Aβ$_{1-14}$-εK-KKKMvF3 Th | 59 | DAEFRHDSGYEVHH-εK-KKK-ISISEIKGVIVHKIEGILF<br>                                T   RT    TR  T |
| Aβ$_{1-14}$-εK-HBsAg1 Th | 60 | DAEFRHDSGYEVHH-εK-KKKLFLLTKLLTLPQSLD<br>                              RRRIKII RII I L IR<br>                                VRVV  VV V I V<br>                                F FF   FF F V F<br>                                       F |
| (Aβ$_{1-14}$)$_4$-(εK)$_2$-εK-MvF1 Th | 61 | (DAEFRHDSGYEVHH)$_4$-εK$_2$-εK-LSEIKGVIVHRLEGV |
| Aβ$_{1-14}$-εK-KKK-MvF4 Th | 62 | DAEFRHDSGYEVHH-εK-KKK-ISISEIKGVIVHKIETILF<br>                                T   RT    TR |
| Aβ$_{1-14}$-εK-KKK-HBsAg2 Th | 63 | DAEFRHDSGYEVHH-εK-KKK-IITITRIITIPQSLD<br>                                 FFLL   L  ITTI |
| Aβ$_{1-14}$-εK-KKK-MvF5 Th | 64 | DAEFRHDSGYEVHH-εK-KKK-ISITEIKGVIVHRIETILF |
| Aβ$_{1-14}$-εK-HBsAg3 Th | 65 | DAEFRHDSGYEVHH-εK-KKK-IITITRIITIITTID |

TABLE 4

Assessment of Immogenicity in Guinea Pigs upon Prime (0 wpi) and boost (4 wpi) with vaccine formulations comprising various Aβ derived peptide immunogen constructs

| Group No. | Description of Aβ derived peptide immunogen construct in the vaccine formulation | SEQ ID NO: | Animal ID | 0 wpi $A\beta_{1-42}$ ELISA ELISA $Log_{10}$ Titer | 4 wpi $A\beta_{1-42}$ ELISA ELISA $Log_{10}$ Titer | 6 wpi $A\beta_{1-42}$ ELISA ELISA $Log_{10}$ Titer | 8 wpi $A\beta_{1-42}$ ELISA ELISA $Log_{10}$ Titer |
|---|---|---|---|---|---|---|---|
| 1 | $A\beta_{1-42}$ peptide | 1 | 2723 | 0.438 | 3.574 | 3.460 | 3.744 |
|  |  |  | 2724 | 0.570 | 2.582 | 2.684 | 2.649 |
|  |  |  | 2725 | 0.630 | 3.232 | 3.279 | 2.958 |
|  |  |  | Geomean | 0.540 | 3.101 | 3.123 | 3.084 |
| 2 | $A\beta_{1-28}$ peptide | 3 | 2726 | 0.330 | 3.768 | 3.572 | 3.369 |
|  |  |  | 2727 | 0.440 | 3.690 | 3.688 | 3.759 |
|  |  |  | 2728 | 0.350 | 3.683 | 3.879 | 3.960 |
|  |  |  | Geomean | 0.370 | 3.713 | 3.711 | 3.688 |
| 3 | $A\beta_{1-14}$ peptide | 4 | 2729 | 0.620 | 1.235 | 1.212 | 1.241 |
|  |  |  | 2730 | 0.570 | 1.142 | 1.113 | 1.151 |
|  |  |  | 2731 | 0.420 | 1.211 | 1.114 | 1.189 |
|  |  |  | Geomean | 0.529 | 1.195 | 1.145 | 1.193 |
| 4 | $A\beta_{1-14}$-εK-*Clostridium tetani*1 Th | 48 | 2763 | 0.591 | 1.736 | 2.532 | 2.920 |
|  |  |  | 2764 | 0.582 | 1.943 | 0.968 | 1.511 |
|  |  |  | 2765 | 0.514 | 0.890 | 1.591 | 2.435 |
|  |  |  | Geomean | 0.561 | 1.443 | 1.574 | 2.207 |
| 6 | $A\beta_{1-10}$-εK-MVF1 Th | 49 | 2757 | 0.424 | 4.124 | 4.622 | 4.523 |
|  |  |  | 2758 | 0.649 | 4.034 | 4.322 | 4.372 |
|  |  |  | 2759 | 0.753 | 4.275 | 4.555 | 4.364 |
|  |  |  | Geomean | 0.592 | 4.143 | 4.498 | 4.419 |
| 7 | $A\beta_{1-12}$-εK-MVF1 Th | 50 | 2760 | 0.342 | 4.356 | 4.732 | 4.534 |
|  |  |  | 2761 | 0.563 | 4.574 | 4.352 | 4.623 |
|  |  |  | 2762 | 0.733 | 4.356 | 4.623 | 4.733 |
|  |  |  | Geomean | 0.521 | 4.427 | 4.566 | 4.629 |
| 5 | $A\beta_{1-14}$-εK-MVF1 Th | 51 | 2766 | 0.342 | 4.744 | 4.854 | 4.878 |
|  |  |  | 2767 | 0.647 | 4.500 | 5.337 | 4.777 |
|  |  |  | 2768 | 0.182 | 5.074 | 4.791 | 4.601 |
|  |  |  | Geomean | 0.343 | 4.767 | 4.988 | 4.751 |
| 8 | $A\beta_{1-14}$-εK-*Bordetella pertussis* Th | 52 | 2769 | 0.648 | 2.235 | 3.571 | 2.686 |
|  |  |  | 2770 | 0.415 | 2.284 | 4.203 | 3.799 |
|  |  |  | 2771 | 0.488 | 1.331 | 2.541 | 2.202 |
|  |  |  | Geomean | 0.508 | 1.894 | 3.366 | 2.822 |
| 9 | $A\beta_{1-14}$-εK-*Clostridium tetani* 2 Th | 53 | 2772 | 0.714 | 1.843 | 2.818 | 2.761 |
|  |  |  | 2773 | 1.165 | 3.370 | 1.297 | 1.828 |
|  |  |  | 2774 | 0.886 | 1.398 | 3.112 | 3.165 |
|  |  |  | Geomean | 0.903 | 2.055 | 2.249 | 2.518 |
| 10 | $A\beta_{1-14}$-εK-Diphtheria Th | 54 | 2775 | 0.314 | 3.674 | 4.675 | 4.358 |
|  |  |  | 2776 | 0.233 | 0.780 | 1.587 | 1.695 |
|  |  |  | 2777 | 0.780 | 3.629 | 4.473 | 3.718 |
|  |  |  | Geomean | 0.385 | 2.183 | 3.214 | 3.017 |
| 11 | $A\beta_{1-14}$-εK-*Plasmodium falciparum* Th | 55 | 2778 | 0.868 | 3.941 | 3.856 | 3.382 |
|  |  |  | 2779 | 0.464 | 1.926 | 2.549 | 2.633 |
|  |  |  | 2780 | 0.627 | 4.350 | 3.723 | 3.218 |
|  |  |  | Geomean | 0.632 | 3.208 | 3.320 | 3.060 |
| 12 | $A\beta_{1-14}$-εK-*Schistosoma mansoni* Th | 56 | 2781 | 0.968 | 0.395 | 2.475 | 2.583 |
|  |  |  | 2782 | 0.754 | 1.101 | 2.554 | 2.692 |
|  |  |  | 2783 | 0.680 | 1.882 | 0.881 | 1.250 |
|  |  |  | Geomean | 0.792 | 0.935 | 1.773 | 2.056 |
| 13 | $A\beta_{1-14}$-εK-Cholera Toxin Th | 57 | 2784 | 0.836 | 4.218 | 4.735 | 4.287 |
|  |  |  | 2785 | 1.111 | 4.704 | 5.357 | 5.347 |
|  |  |  | 2786 | 0.497 | 4.252 | 4.698 | 4.600 |
|  |  |  | Geomean | 0.773 | 4.386 | 4.921 | 4.724 |
| 14 | $A\beta_{1-14}$-εK-MVF2 Th | 58 | 2787 | 1.333 | 5.347 | 5.398 | 4.791 |
|  |  |  | 2788 | 0.546 | 5.495 | 5.409 | 4.931 |
|  |  |  | 2789 | 0.705 | 5.658 | 5.745 | 4.822 |
|  |  |  | Geomean | 0.801 | 5.498 | 5.515 | 4.848 |
| 15 | $A\beta_{1-14}$-εK-MVF3 Th | 59 | 2790 | 0.701 | 4.943 | 5.678 | 5.569 |
|  |  |  | 2791 | 0.360 | 3.468 | 5.745 | 5.658 |
|  |  |  | 2792 | 0.494 | 4.759 | 5.319 | 5.347 |
|  |  |  | Geomean | 0.500 | 4.337 | 5.577 | 5.523 |
| 16 | $A\beta_{1-14}$-εK-HBsAg1 Th | 60 | 2793 | 0.880 | 3.199 | 4.561 | 4.431 |
|  |  |  | 2794 | 0.911 | 4.817 | 4.303 | 4.788 |
|  |  |  | 2795 | 0.761 | 4.567 | 5.328 | 5.495 |
|  |  |  | Geomean | 0.848 | 4.129 | 4.711 | 4.885 |
| 17 | $(A\beta_{1-14})_4$-$(εK)_2$-εK-MVF1 Th | 61 | 2796 | 0.479 | 5.041 | 5.585 | 4.696 |
|  |  |  | 2797 | 0.973 | 4.385 | 4.831 | 4.751 |
|  |  |  | 2798 | 0.345 | 3.919 | 4.698 | 3.922 |
|  |  |  | Geomean | 0.544 | 4.425 | 5.023 | 4.439 |

TABLE 5

Assessment of Immogenicity in Guinea Pigs upon Prime (0 wpi) and boost (4 wpi) with vaccine formulations comprising two $A\beta_{1-14}$ derived peptide immunogen constructs and combination thereof

| Group No. | Description of $A\beta_{1-14}$ peptide immunogen construct in the vaccine formulation | SEQ ID NO: | Animal ID | 0 wpi $A\beta_{1-42}$ ELISA ELISA $Log_{10}$ Titer | 3 wpi $A\beta_{1-42}$ ELISA ELISA $Log_{10}$ Titer | 5 wpi $A\beta_{1-42}$ ELISA ELISA $Log_{10}$ Titer | 8 wpi $A\beta_{1-42}$ ELISA ELISA $Log_{10}$ Titer |
|---|---|---|---|---|---|---|---|
| 1 | $A\beta_{1-14}$-εK-KKK-MvF4 Th | 62 | 1935 | 0.587 | 4.362 | 4.579 | 4.447 |
|   |   |   | 1936 | 0.414 | 3.684 | 4.543 | 4.217 |
|   |   |   | 1937 | 0.390 | 4.393 | 3.652 | 4.358 |
|   |   |   | 1938 | 0.179 | 3.768 | 3.648 | 4.283 |
|   |   |   | 1939 | 0.331 | 3.726 | 3.673 | 4.163 |
|   |   |   | 1940 | 0.350 | 3.732 | 4.787 | 3.813 |
|   |   |   | Geomean | 0.354 | 3.932 | 4.117 | 4.208 |
| 2 | $A\beta_{1-14}$-εK-HBsAg2 Th | 63 | 1929 | 0.288 | 2.720 | 3.502 | 3.596 |
|   |   |   | 1930 | 0.507 | 2.817 | 3.559 | 3.653 |
|   |   |   | 1931 | 0.721 | 2.860 | 3.575 | 3.696 |
|   |   |   | 1932 | 0.548 | 2.315 | 3.776 | 3.681 |
|   |   |   | 1933 | 0.619 | 2.322 | 3.742 | 3.836 |
|   |   |   | 1934 | 0.234 | 2.687 | 3.459 | 3.744 |
|   |   |   | Geomean | 0.450 | 2.610 | 3.600 | 3.700 |
| 3 | $A\beta_{1-14}$-εK-KKK-MvF4 Th + $A\beta_{1-14}$-εK-HBsAg2 Th at equal molar ratio | 62 + 63 | 1923 | 0.298 | 4.759 | 4.880 | 4.803 |
|   |   |   | 1924 | 0.554 | 4.619 | 4.979 | 4.702 |
|   |   |   | 1925 | 0.299 | 4.835 | 4.791 | 4.955 |
|   |   |   | 1926 | 0.635 | 4.831 | 4.710 | 5.150 |
|   |   |   | 1927 | 0.911 | 5.097 | 4.278 | 4.313 |
|   |   |   | 1928 | 0.890 | 5.188 | 4.721 | 5.206 |
|   |   |   | Geomean | 0.542 | 4.884 | 4.721 | 4.845 |

TABLE 6

Assessment of Antibodies Directed against the Th peptides or Carrier Protein Element of the Immunogens upon Prime (0 wpi) and boost (4 wpi) with Vaccine Formulations comprising two $A\beta_{1-14}$ derived peptide Immunogen Constructs and Combination thereof in Guinea Pigs

| Group No. | Description of $A\beta_{1-14}$ peptide construct in the vaccine formulation | SEQ ID NO: | Animal ID | 8 wpi $A\beta_{1-42}$ ELISA (SEQ ID NO: 1) ELISA $Log_{10}$ Titer | MvF4 Th ELISA (SEQ ID NO: 44) ELISA $Log_{10}$ Titer | HBsAg2 Th ELISA (SEQ ID NO: 45) ELISA $Log_{10}$ Titer | KLH-ELISA ELISA $Log_{10}$ Titer |
|---|---|---|---|---|---|---|---|
| 1 | $A\beta_{1-14}$-εK-KKK-MvF4 Th | 62 | 1935 | 4.447 | 0.268 | 0.288 | N/A |
|   |   |   | 1936 | 4.217 | 0.216 | 0.504 | N/A |
|   |   |   | 1937 | 4.358 | 0.196 | 0.621 | N/A |
|   |   |   | 1938 | 4.283 | 0.179 | 0.360 | N/A |
|   |   |   | 1939 | 4.163 | 0.332 | 0.519 | N/A |
|   |   |   | 1940 | 3.813 | 0.286 | 0.233 | N/A |
|   |   |   | Geomean | 4.208 | 0.240 | 0.397 | N/A |
| 2 | $A\beta_{1-14}$-εK-HBsAg2 Th | 63 | 1929 | 3.596 | 0.575 | 0.431 | N/A |
|   |   |   | 1930 | 3.653 | 0.423 | 0.257 | N/A |
|   |   |   | 1931 | 3.696 | 0.380 | 0.345 | N/A |
|   |   |   | 1932 | 3.681 | 0.279 | 0.563 | N/A |
|   |   |   | 1933 | 3.836 | 0.336 | 0.365 | N/A |
|   |   |   | 1934 | 3.744 | 0.425 | 0.354 | N/A |
|   |   |   | Geomean | 3.700 | 0.393 | 0.375 | N/A |
| 3 | $A\beta_{1-14}$-εK-KKK-MvF4 Th + $A\beta_{1-14}$-εK-HBsAg2 Th at equal ratio by weight | 62 + 63 | 1923 | 4.803 | 0.350 | 0.631 | N/A |
|   |   |   | 1924 | 4.702 | 0.724 | 0.350 | N/A |
|   |   |   | 1925 | 4.955 | 0.324 | 0.391 | N/A |
|   |   |   | 1926 | 5.150 | 0.394 | 0.452 | N/A |
|   |   |   | 1927 | 4.313 | 0.520 | 0.368 | N/A |
|   |   |   | 1928 | 5.206 | 0.528 | 0.364 | N/A |
|   |   |   | Geomean | 4.845 | 0.455 | 0.417 | N/A |
| 4 | KLH-(C)-$A\beta_{1-14}$ | 4 | 1968 | 3.626 | N/A | N/A | 7.006 |
|   |   |   | 1969 | 3.981 | N/A | N/A | 7.167 |
|   |   |   | 1970 | 2.227 | N/A | N/A | 4.658 |
|   |   |   | 1971 | 3.005 | N/A | N/A | 5.593 |
|   |   |   | 1974 | 2.527 | N/A | N/A | 7.000 |
|   |   |   | 1975 | 2.599 | N/A | N/A | 7.000 |
|   |   |   | Geomean | 2.931 | N/A | N/A | 6.326 |

TABLE 7

Assessment of Immunogenicity in Baboons upon Prime (0 wpi) and Boosts (3 and 6 wpi) with vaccine formulations comprising varying amounts of $A\beta_{1-14}$ derived peptide immunogen constructs (SEQ ID NOs: 62 + 63) in ISA51 w/o Emulsion and in Alum

| Group No. | Description of vaccine formulation | Animal ID | 0 wpi $A\beta_{1-42}$ ELISA $Log_{10}$ Titer | 5 wpi $A\beta_{1-42}$ ELISA $Log_{10}$ Titer | 8 wpi $A\beta_{1-42}$ ELISA $Log_{10}$ Titer | 10 wpi $A\beta_{1-42}$ ELISA $Log_{10}$ Titer | 14 wpi $A\beta_{1-42}$ ELISA $Log_{10}$ Titer |
|---|---|---|---|---|---|---|---|
| 1 | SEQ ID NO: 62 + SEQ ID NO: 63 at equal molar ratio @100 µg in 0.5 mL Alum (alhydrogel) (ALHYDROGEL ®) | X798 | 1.397 | 2.463 | 2.985 | 2.337 | 1.478 |
| 2 | SEQ ID NO: 62 + SEQ ID NO: 63 at equal molar ratio @25 µg in 0.5 mL ISA51 (w/o) emulsion | X1498 | 1.394 | 3.462 | 3.236 | 2.422 | 1.774 |
| 3 | SEQ ID NO: 62 + SEQ ID NO: 63 at equal molar ratio @100 µg in 0.5 mL ISA51 (w/o) emulsion | X299 | 1.140 | 3.038 | 3.427 | 3.345 | 2.205 |
|   |   | X1098 | 1.610 | 3.987 | 4.460 | 4.662 | 3.666 |
|   |   | X398 | 1.541 | 3.926 | 4.353 | 4.095 | 2.972 |
|   |   | Geomean | 1.414 | 3.623 | 4.052 | 3.997 | 2.885 |
| 4 | SEQ ID NO: 62 + SEQ ID NO: 63 at equal molar ratio @400 µg in 0.5 mL ISA51 (w/o) emulsion | X1198 | 1.696 | 3.696 | 5.051 | 5.115 | 4.531 |

TABLE 8

Assessment of Antibodies (from 8 wpi sera in guinea pigs) Directed against the Th peptides of the $A\beta$ peptide Immunogen constructs upon Prime (0 wpi) and boost (4 wpi) with Vaccine Formulation comprising two $A\beta_{1-14}$ Peptide Immunogen Constructs

| Group No. | Description of $A\beta_{1-14}$ peptide construct in the vaccine formulation | SEQ ID No: | Animal ID | 8 wpi $A\beta_{1-42}$ ELISA (SEQ ID NO: 1) ELISA $Log_{10}$ Titer | 8 wpi MvF 5 Th ELISA (SEQ ID NO: 46) ELISA $Log_{10}$ Titer | 8 wpi HBsAg3 Th ELISA (SEQ ID NO: 47) ELISA $Log_{10}$ Titer |
|---|---|---|---|---|---|---|
| 1 | $A\beta_{1-14}$-εK-KKK-MvF5 Th + $A\beta_{1-14}$-εK-HBsAg3 Th at equimolar ratio | 64 + 65 | 2123 | 4.683 | 0.210 | 0.314 |
|   |   |   | 2124 | 3.884 | 0.325 | 0.421 |
|   |   |   | 2125 | 3.923 | 0.433 | 0.311 |
|   |   |   | 2126 | 3.578 | 0.542 | 0.554 |
|   |   |   | 2127 | 3.348 | 0.520 | 0.381 |
|   |   |   | 2128 | 3.482 | 0.403 | 0.415 |
|   |   |   | Geomean | 3.792 | 0.387 | 0.392 |

TABLE 9

Epitope Mapping for Fine Specificity Analysis at the N-terminus of $A\beta_{1-42}$ by sera from vaccinated baboons collected over the period of immunization (from 0 to 111 wpi)

| Peptide SEQ ID NO: | Peptide Sequence | ELISA Titer titers ($Log_{10}$) Weeks post immunization | | | |
|---|---|---|---|---|---|
| | | 0 | 10 | 84 | 111 |
| 8 | TEEISEVKMD | 0.23 | 0.26 | 0.16 | 0.15 |
| 9 | EEISEVKMDA | 0.24 | 0.30 | 0.21 | 0.22 |
| 10 | EISEVKMDAE | 0.23 | 0.25 | 0.16 | 0.14 |
| 11 | ISEVKMDAEF | 0.20 | 0.20 | 0.15 | 0.13 |
| 12 | SEVKMDAEFR | 0.21 | 0.24 | 0.16 | 0.13 |
| 13 | EVKMDAEFRH | 0.19 | 0.23 | 0.16 | 0.14 |
| 14 | VKMDAEFRHD | 0.27 | 0.46 | 0.48 | 0.55 |

TABLE 9-continued

Epitope Mapping for Fine Specificity Analysis at the N-terminus of Aβ$_{1-42}$ by sera from vaccinated baboons collected over the period of immunization (from 0 to 111 wpi)

| Peptide SEQ ID NO: | | Peptide Sequence | ELISA Titer titers (Log$_{10}$) Weeks post immunization | | | |
|---|---|---|---|---|---|---|
| | | | 0 | 10 | 84 | 111 |
| 15 | | KMDAEFRHDS | 0.26 | 0.36 | 0.41 | 0.51 |
| 16 | | MDAEFRHDSG | 0.26 | 0.32 | 0.16 | 0.17 |
| 6 | | DAEFRHDSGY | 0.26 | 3.26 | 3.65 | 3.21 |
| 17 | | AEFRHDSGYE | 0.25 | 0.35 | 0.25 | 0.19 |
| 18 | | EFRHDSGYEV | 0.24 | 0.30 | 0.18 | 0.18 |
| 19 | | FRHDSGYEVH | 0.20 | 0.40 | 0.22 | 0.30 |
| 20 | | RHDSGYEVHH | 0.23 | 0.34 | 0.27 | 0.41 |
| 21 | | HDSGYEVHHQ | 0.21 | 0.40 | 0.18 | 1.14 |
| 22 | | DSGYEVHHQK | 0.32 | 0.78 | 0.64 | 0.76 |
| 23 | | SGYEVHHQKL | 0.13 | 0.49 | 0.51 | 0.78 |
| 24 | | GYEVHHQKLV | 0.13 | 0.27 | 0.19 | 0.12 |
| 25 | | YEVHHQKLVF | 0.16 | 0.43 | 0.15 | 0.22 |
| 26 | | EVHHQKLVFF | 0.17 | 0.26 | 0.13 | 0.13 |
| 27 | | VHHQKLVFFA | 0.16 | 0.23 | 0.12 | 0.11 |
| 28 | | HHQKLVFFAE | 0.19 | 0.22 | 0.13 | 0.12 |
| 29 | | HQKLVFFAED | 0.18 | 0.21 | 0.13 | 0.13 |
| 3 | Aβ$_{1-28}$ | DAEFRHDSGYEVHHQKLVFFAEDVGSNK | 0.12 | 3.26 | 3.57 | 3.32 |

TABLE 10

Epitope Mapping by Competitive Inhibition ELISA with Hyperimmune Sera from Baboons

| Peptide concentration μg/mL | Percent (%) Inhibition ELISA after peptide pre-absorption of sera | | | | | |
|---|---|---|---|---|---|---|
| | Aβ$_{1-28}$ (SEQ ID NO: 3) | Aβ$_{1-10}$ (SEQ ID NO: 6) | Aβ$_{[-1]-9}$ (SEQ ID NO: 16) | Aβ$_{2-11}$ (SEQ ID NO: 17) | Aβ$_{3-12}$ (SEQ ID NO: 18) | Aβ17$_{-43}$ (SEQ ID NO: 67) |
| 32 | 99 | 97 | 39 | 19 | 3 | 7 |
| 8 | 93 | 93 | 17 | 6 | 0 | 0 |
| 2 | 72 | 82 | 8 | 0 | 0 | 5 |
| 1 | 63 | 72 | 4 | 0 | 0 | 10 |
| 0.5 | 50 | 55 | 9 | 0 | 1 | 9 |
| 0.25 | 34 | 37 | 8 | 3 | 1 | 5 |
| 0 | 0 | 0 | 0 | 0 | 0 | 0 |

50% inhibition of Aβ$_{1-10}$ peptide is about 0.3 μg/mL. Specificity of baboon anti-Aβ antibody predominately targets the N-terminal aspartic acid (D).
Epitope Mapping Using 10-mer Aβ Peptides of Human Amyloid Precursor Protein (hAPP) detected by Baboon Immune Serum Samples show Specificity to N-terminus Aβ$_{1-10}$ Peptide.

TABLE 11

Effect of Repeat Doses of UBI AD Vaccine on Antibody Titers (Log$_{10}$) in Cynomolgus Macaques

| Group μg/dose | Time (Week) | | | | | | | |
|---|---|---|---|---|---|---|---|---|
| | 0 | 3 | 6 | 9 | 12 | 15 | 21 | After 27 |
| 0 | 0.838 ± 0.410 | 1.249 ± 0.190 | 1.169 ± 0.206 | 1.790 ± 0.408 | 1.382 ± 0.392 | 1.199 ± 0.261 | 1.068 ± 0.142 | 0.860 ± 0.257 |
| 150 | 1.056 ± 0.186 | 2.252 ± 0.702 | 3.507 ± 0.493 | 3.714 ± 0.461 | 3.287 ± 0.577 | 3.905 ± 0.669 | 3.580 ± 0.315 | 3.644 ± 1.403 |
| 750 | 0.829 ± 0.185 | 3.169 ± 0.487 | 4.217 ± 0.415 | 4.316 ± 0.416 | 3.784 ± 0.278 | 3.977 ± 0.125 | 4.027 ± 0.222 | 3.596 ± 0.080 |

N = 6 macaques per group (weeks 0, 3, 6, 9, 12 and 15);
N = 3 macaques per group (weeks 21, 27)

TABLE 12

Specificity Analyses of Antisera Collected at Weeks 9 and 15 from Cynomolgus Macaques Immunized with the Placebo Vaccine (0 μg/dose) or UBI AD Vaccine (150 μg/dose or 750 μg/dose)

| SEQ ID NO: | Sequence | | 0 μg/dose 9 WPI | 0 μg/dose 15 WPI | 150 μg/dose 9 WPI | 150 μg/dose 15 WPI | 750 μg/dose 9 WPI | 750 μg/dose 15 WPI |
|---|---|---|---|---|---|---|---|---|
| 8 | TEEISEVKMD | | 0.065 | 0.054 | 0.075 | 0.084 | 0.061 | 0.078 |
| 9 | EEISEVKMDA | | 0.061 | 0.060 | 0.082 | 0.092 | 0.081 | 0.076 |
| 10 | EISEVKMDAE | | 0.053 | 0.070 | 0.060 | 0.056 | 0.064 | 0.053 |
| 11 | ISEVKMDAEF | | 0.059 | 0.055 | 0.055 | 0.058 | 0.063 | 0.062 |
| 12 | SEVKMDAEFR | | 0.045 | 0.047 | 0.056 | 0.053 | 0.054 | 0.050 |
| 13 | EVKMDAEFRH | | 0.047 | 0.041 | 0.046 | 0.047 | 0.054 | 0.047 |
| 14 | VKMDAEFRHD | | 0.050 | 0.043 | 0.068 | 0.053 | 0.061 | 0.054 |
| 15 | KMDAEFRHDS | | 0.056 | 0.055 | 0.065 | 0.031 | 0.069 | 0.062 |
| 16 | MDAEFRHDSG | | 0.049 | 0.041 | 0.056 | 0.061 | 0.051 | 0.056 |
| 6 | DAEFRHDSGY N-terminus | | 0.051 | 0.053 | 0.691 | 0.725 | 0.972 | 1.682 |
| 17 | AEFRHDSGYE | | 0.045 | 0.054 | 0.058 | 0.059 | 0.054 | 0.060 |
| 18 | EFRHDSGYEV | | 0.054 | 0.046 | 0.047 | 0.060 | 0.042 | 0.052 |
| 19 | FRHDSGYEVH | | 0.051 | 0.060 | 0.085 | 0.076 | 0.066 | 0.096 |
| 20 | RHDSGYEVHH | | 0.054 | 0.060 | 0.296 | 0.400 | 0.453 | 0.461 |
| 21 | HDSGYEVHHQ | | 0.059 | 0.052 | 0.266 | 0.494 | 0.419 | 0.332 |
| 22 | DSGYEVHHQK | | 0.042 | 0.051 | 0.270 | 0.289 | 0.405 | 0.197 |
| 23 | SGYEVHHQKL | | 0.051 | 0.048 | 0.097 | 0.071 | 0.077 | 0.082 |
| 24 | GYEVHHQKLV | | 0.042 | 0.047 | 0.055 | 0.067 | 0.052 | 0.059 |
| 25 | YEVHHQKLVF | | 0.042 | 0.036 | 0.092 | 0.069 | 0.069 | 0.058 |
| 26 | EVHHQKLVFF | | 0.034 | 0.034 | 0.044 | 0.051 | 0.042 | 0.044 |
| 27 | VHHQKLVFFA | | 0.037 | 0.039 | 0.046 | 0.082 | 0.057 | 0.083 |
| 28 | HHQKLVFFAE | | 0.038 | 0.040 | 0.044 | 0.052 | 0.046 | 0.032 |
| 29 | HQKLVFFAED | | 0.048 | 0.051 | 0.050 | 0.058 | 0.047 | 0.050 |
| 30 | QKLVFFAEDV | | 0.044 | 0.047 | 0.043 | 0.055 | 0.062 | 0.059 |
| 3 | Aβ$_{1-28}$ | DAEFRHDSGYEVHHQKLVFFAEDVGSNK | NA | 0.087 | NA | 3.107 | NA | 3.069 |

NA = Not available

TABLE 13

Aβ$_{1-40}$ Concentration (pg/mL) from Cynomolgus Macaques Before and After UBI AD Vaccine in Serum (upper panel) and Cerebral Spinal Fluid (lower panel)

| | Aβ$_{1-40}$ Serum | | | |
|---|---|---|---|---|
| Vaccine Dose | 0 wpi (n = 6) | 15 wpi (n = 6) | 21 wpi (n = 3) | 26 wpi (n = 3) |
| 0 μg (control) | 61.7 ± 12.7 | 63.0 ± 16.8 | 63.7 ± 12.2 | 52.7 ± 2.5 |
| 150 μg | 53.9 ± 6.3 | 127.4 ± 23.8 | 144.8 ± 17.3 | 158.0 ± 38.1 |
| 750 μg | 56.8 ± 7.7 | 138.2 ± 18.9 | 144.5 ± 22.5 | 118.0 ± 20.9 |

| | Aβ$_{1-40}$ Cerebral Spinal Fluid | |
|---|---|---|
| Vaccine Dose | 15 wpi (n = 3) | 28 wpi (n = 3) |
| 0 μg (control) | 56.4 ± 6.0 | 59.7 ± 5.9 |
| 150 μg | 63.9 ± 6.5 | 67.6 ± 5.4 |
| 750 μg | 57.5 ± 5.9 | 54.3 ± 2.9 |

TABLE 14

Proliferation Expressed as Stimulation Index by Peripheral Blood Mononuclear Cells in Cynomolgus Macaque upon Coculture with Various Aβ peptides

| | Stimulation Index (S.I.) [positive S.I. > 4.0] | | |
|---|---|---|---|
| Peptide Domain | Group 1 Placebo Vaccine Control | Group 2 UBITh® AD Vaccine (Low dose) | Group 3 UBITh® AD Vaccine (High dose) |
| Aβ$_{1-14}$ | -- (1.5) | -- (0.2) | -- (1.2) |
| Aβ$_{1-16}$ | ++ (12.7) | + (7.8) | + (7.9) |
| Aβ$_{17-42}$ | ++++ (83.7) | ++++ (46.9) | ++++ (56.6) |
| Aβ$_{1-42}$ | ++ (16.0) | ++ (15.1) | ++ (15.5) |

Aβ$_{1-14}$ (SEQ ID NO: 4) DAEFRHDSGYEVHH
Aβ$_{1-16}$ (SEQ ID NO: 66) DAEFRHDSGYEVHHQK
Aβ$_{17-42}$ (SEQ ID NO: 67) LVFFAEDVGSNKGAIIGLMVGGVVIA
Aβ$_{1-42}$ (SEQ ID NO: 1) DAEFRHDSGYEVHHQKLVFFAEDVGSNKGAIIGLMVGGVVIA

TABLE 15

Measurement of Cytokine Concentration in Cynomolgus Macaque Peripheral Blood Mononuclear Cells (PBMCs) upon Stimulation with Aβ$_{1-14}$, Aβ$_{1-42}$ peptides or PHA (Phytohemagglutin) Mitogen[a]

| | | Cytokine concentration[b] (pg/mL) | | |
|---|---|---|---|---|
| Cytokine | Vaccine dose | Aβ$_{1-14}$ | Aβ$_{1-42}$ | PHA |
| IL-2 | Placebo | BDL[c] | 23.3 ± 13.1 | 90.6 ± 12.4 |
| | 150 μg | BDL | 19.4 ± 9.7 | 96.1 ± 13.3 |
| | 750 μg | BDL | 25.2 ± 11.8 | 97.5 ± 6.6 |
| IL-6 | Placebo | BDL | 23.1 ± 11.7 | 69.1 ± 12.0 |
| | 150 μg | BDL | 15.0 ± 9.1 | 70.6 ± 15.7 |
| | 750 μg | BDL | 23.4 ± 10.5 | 66.2 ± 7.3 |
| TNF-α | Placebo | BDL | 9.2 ± 5.3 | 91.0 ± 29.1 |
| | 150 μg | BDL | 7.9 ± 4.8 | 96.1 ± 22.2 |
| | 750 μg | BDL | 7.8 ± 5.9 | 89.0 ± 13.7 |

[a]Peripheral blood mononuclear cells (PBMC) from six Cynomolgus macaques were cultured 24 hour after the last immunization (15 wpi) in the absence or presence of Aβ peptides or PHA mitogen. Culture supernatants were tested for detectable concentrations of each cytokine (IL2, IL6 and TNFα) by commercial ELISA tests (U-CyTech Biosciences, Utrecht, The Netherlands).
[b]Result was shown as mean ± standard deviation.
[c]BDL, below detection level.

TABLE 16

Comparison of Immunogenicity of UBI AD vaccine at Difference Dose Levels in Guinea Pigs, Rhesus Macaques and Baboons

| | | | Antibody titer Log$_{10}$ >2[3] | |
|---|---|---|---|---|
| | Peptide dose (μg)[2] | | 3 weeks post | 3 weeks post |
| Species [BW] | per animal | per kg BW | 1 dose | 2 doses |
| Guinea pig [300-400 grams] | 1 | 2.5-3.3 | 0/3[4] | 0/3 |
| | 3 | 7.5-10 | 0/3 | 0/3 |
| | 10 | 25-33 | 0/6 | 5/6 |
| | 30 | 75-100 | 1/6 | 6/6 |
| | 100 | 250-333 | 2/3 | 3/3 |
| | 300 | 750-1000 | 2/3 | 3/3 |
| Macaque [4-5 kg] | 150 | 30-37.5 | 4/6 | 6/6 |
| | 750 | 150-187.5 | 6/6 | 6/6 |
| Baboon [10-15 kg] | 300-A[1] | 20-30 | 3/4 | 4/4 |
| | 300-B[1] | 20-30 | 2/2 | 2/2 |
| | 1200 | 80-120 | 2/2 | 2/2 |

[1]Baboons immunized in Part A at 0 and 3 weeks and in Part B at 78 and 81 weeks (after 72 week rest period).
[2]Each 1 mL dose consists of 600 μg peptide.
[3]Log$_{10}$ values >2 are scored as positive anti-Aβ titers.
[4]Numbers represent number of animals with positive titers/total number of animals tested.
BW: body weight;

TABLE 17

Epitope Mapping for Fine Specificity Analysis at the N-terminus of Aβ$_{1-42}$ by Sera (16 wpi) from all vaccinated patients

| SEQ ID NO: | Peptide Sequence | Aβ Position | P101 | P102 | P103 | P104 | P105 | P106 | P107 | P108 | P109 |
|---|---|---|---|---|---|---|---|---|---|---|---|
| 8 | TEEISEVKMD | -9 to 1 | 0 | 0 | 0 | 0 | 0 | 0 | 0 | 0 | 0 |
| 9 | EEISEVKMDA | -8 to 2 | 0 | 0 | 0 | 0 | 0 | 0 | 0 | 0 | 0 |
| 10 | EISEVKMDAE | -7 to 3 | 0 | 0 | 0 | 0 | 0 | 0 | 0 | 0 | 0 |
| 11 | ISEVKMDAEF | -6 to 4 | 0 | 0 | 0 | 0 | 0 | 0 | 0 | 0 | 0 |
| 12 | SEVKMDAEFR | -5 to 5 | 10 | 0 | 0 | 0 | 0 | 0 | 0 | 0 | 0 |
| 13 | EVKMDAEFRH | -4 to 6 | 1 | 0 | 0 | 0 | 0 | 0 | 0 | 0 | 0 |
| 14 | VKMDAEFRHD | -3 to 7 | 31 | 0 | 0 | 0 | 0 | 0 | 0 | 0 | 0 |
| 15 | KMDAEFRHDS | -2 to 8 | 94 | 0 | 0 | 0 | 0 | 0 | 0 | 0 | 0 |
| 16 | MDAEFRHDSG | -1 to 9 | 420 | 12 | 0 | 0 | 0 | 0 | 0 | 0 | 0 |
| 6 | DAEFFHDSGY N-terminus | 1 to 10 | 1983 | 1669 | 36 | 1721 | 3840 | 5193 | 2838 | 948 | 1675 |

TABLE 17-continued

Epitope Mapping for Fine Specificity Analysis at the N-terminus
of Aβ$_{1-42}$ by Sera (16 wpi) from all vaccinated patients

| | | | | | | | | | | | |
|---|---|---|---|---|---|---|---|---|---|---|---|
| 17 | AEFRHDSGYE | 2 to 11 | 2 | 0 | 0 | 0 | 0 | 0 | 0 | 0 | 0 |
| 18 | EFRHDSGYEV | 3 to 12 | 0 | 0 | 0 | 0 | 0 | 0 | 0 | 0 | 0 |
| 19 | FRHDSGYEVH | 4 to 13 | 0 | 0 | 0 | 0 | 0 | 0 | 0 | 0 | 0 |
| 20 | RHDSGYEVHH | 5 to 14 | 0 | 0 | 0 | 0 | 0 | 0 | 0 | 0 | 0 |
| 21 | HDSGYEVHHQ | 6 to 15 | 0 | 0 | 0 | 0 | 0 | 0 | 0 | 0 | 0 |
| 22 | DSGYEVHHQK | 7 to 16 | 214 | 0 | 0 | 0 | 0 | 0 | 0 | 0 | 0 |
| 23 | SGYEVHHQKL | 8 to 17 | 0 | 0 | 0 | 0 | 0 | 0 | 0 | 0 | 0 |
| 24 | GYEVHHQKLV | 9 to 18 | 0 | 0 | 0 | 0 | 0 | 0 | 0 | 0 | 0 |
| 25 | YEVHHQKLVF | 10 to 19 | 0 | 0 | 0 | 0 | 0 | 0 | 0 | 0 | 0 |
| 26 | EVHHQKLVFF | 11 to 20 | 0 | 0 | 0 | 0 | 0 | 0 | 0 | 0 | 0 |
| 27 | VHHQKLVFFA | 12 to 21 | 0 | 0 | 0 | 0 | 0 | 0 | 0 | 0 | 0 |
| 28 | HHQKLVFFAE | 13 to 22 | 0 | 0 | 0 | 0 | 0 | 0 | 0 | 0 | 0 |
| 29 | HQKLVFFAED | 14 to 23 | 0 | 0 | 0 | 0 | 0 | 0 | 0 | 0 | 0 |
| 30 | QKLVFFAEDV | 15 to 24 | 0 | 0 | 0 | 0 | 0 | 0 | 0 | 0 | 0 |
| 3 | DAEFRHDSGYEVHHQKLVFFAEDVGSNK | 1 to 28 | 685 | 161 | 220 | 295 | 450 | 715 | 1163 | 478 | 430 |

| SEQ ID NO: | Subjects | | | | | | | | | |
|---|---|---|---|---|---|---|---|---|---|---|
| | P201 | P202 | P203 | P204 | P205 | P206 | P207 | P208 | P209 | P210 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 0 | 0 | 0 | 0 | 0 | 0 | 0 | 0 | 0 | 0 |
| 12 | 0 | 0 | 0 | 0 | 0 | 0 | 0 | 0 | 0 | 0 |
| 13 | 58 | 0 | 0 | 0 | 0 | 0 | 1 | 0 | 0 | 0 |
| 14 | 0 | 0 | 0 | 1 | 0 | 0 | 0 | 0 | 0 | 13 |
| 15 | 2 | 7 | 0 | 12 | 0 | 0 | 0 | 0 | 0 | 52 |
| 16 | 9 | 116 | 0 | 17 | 0 | 0 | 2 | 6 | 0 | 121 |
| 6 | 1034 | 42313 | 1284 | 274 | 81 | 1797 | 6024 | 4093 | 27596 | 20968 |
| 17 | 3 | 0 | 0 | 0 | 0 | 0 | 0 | 0 | 0 | 0 |
| 18 | 0 | 0 | 0 | 0 | 0 | 0 | 0 | 0 | 0 | 0 |
| 19 | 0 | 0 | 0 | 0 | 0 | 0 | 0 | 0 | 0 | 0 |
| 20 | 0 | 0 | 0 | 0 | 0 | 0 | 0 | 0 | 0 | 0 |
| 21 | 0 | 0 | 0 | 0 | 0 | 0 | 0 | 0 | 0 | 0 |
| 22 | 0 | 0 | 0 | 0 | 0 | 0 | 0 | 0 | 0 | 0 |
| 23 | 0 | 0 | 0 | 0 | 0 | 0 | 0 | 0 | 0 | 0 |
| 24 | 0 | 0 | 0 | 0 | 0 | 0 | 16 | 0 | 0 | 0 |
| 25 | 0 | 0 | 0 | 0 | 0 | 0 | 10 | 0 | 0 | 0 |
| 26 | 0 | 0 | 0 | 0 | 0 | 0 | 0 | 0 | 0 | 0 |
| 27 | 0 | 0 | 0 | 0 | 0 | 0 | 27 | 0 | 0 | 0 |
| 28 | 0 | 0 | 0 | 0 | 0 | 0 | 0 | 0 | 0 | 0 |
| 29 | 0 | 0 | 0 | 0 | 0 | 0 | 0 | 0 | 0 | 0 |
| 30 | 0 | 0 | 0 | 0 | 0 | 0 | 0 | 0 | 0 | 0 |
| 3 | 339 | 509 | 279 | 284 | 39 | 226 | 906 | 1157 | 893 | 1321 |

TABLE 18

Analysis of Aβ$_{1-40}$ concentrations (pg/mL) in Plasma of AD patients Before and After Immunization with UBI AD Vaccine and Correlation with Anti-Aβ$_{1-28}$ Antibody Titer (Log$_{10}$) in Decreasing Order

| Subject ID (n = 12) | Anti-Aβ$_{1-28}$ Ab (Log$_{10}$) Week 16 | Aβ$_{1-40}$ (pg/mL) Week 0 | Aβ$_{1-40}$ (pg/mL) Week 16 | Aβ$_{1-40}$ (pg/mL) Week16-Week0 |
|---|---|---|---|---|
| P207 | 3.504 | 72.6 | 114.5 | 41.9 |
| P105 | 3.164 | 53.5 | 75.1 | 21.6 |
| P106 | 3.048 | 124.9 | 145.8 | 20.9 |
| P109 | 2.778 | 492.9 | 1031.9 | 639.0 |
| P108 | 2.622 | 29.3 | 44.4 | 15.1 |
| P208 | 2.594 | 85.2 | 129.9 | 44.7 |
| P206 | 2.462 | 90.2 | 102.1 | 11.9 |
| P204 | 2.420 | 30.7 | 45.1 | 14.4 |

TABLE 18-continued

Analysis of $A\beta_{1-40}$ concentrations (pg/mL) in Plasma of AD patients Before and After Immunization with UBI AD Vaccine and Correlation with Anti-$A\beta_{1-28}$ Antibody Titer ($Log_{10}$) in Decreasing Order

| Subject ID (n = 12) | Anti-$A\beta_{1-28}$ Ab ($Log_{10}$) Week 16 | $A\beta_{1-40}$ (pg/mL) Week 0 | $A\beta_{1-40}$ (pg/mL) Week 16 | $A\beta_{1-40}$ (pg/mL) Week16-Week0 |
|---|---|---|---|---|
| P205 | 1.989 | 77.7 | 72.0 | −5.7 |
| P107 | 1.790 | 147.0 | 92.7 | −54.3 |
| P209 | 1.467 | 58.6 | 87.7 | 29.1 |
| P210 | 1.449 | 44.4 | 32.6 | −11.8 |

Data in bold type have increased levels of $A\beta_{1-40}$ at week 16 after immunizations of UBI AD vaccine at weeks 0, 4 and 12.

TABLE 19

Mean Stimulation Indexes by Peripheral Blood Mononuclear Cells (PBMCs) from Patient Subjects Collected at Week 0 and Week 16 Upon Coculture with Various Aβ peptides

| Peptide (SEQ ID NO:) | Week 0 mean (SD) | Week 16 mean (SD) | Difference mean (SD) | Paired t-test p value |
|---|---|---|---|---|
| $A\beta_{1-14}$ (SEQ ID NO: 4) | 0.93 (0.36) | 0.90 (0.22) | −0.03 (0.39) | 0.73 |
| $A\beta_{1-16}$ (SEQ ID NO: 66) | 0.92 (0.30) | 0.98 (0.25) | 0.06 (0.40) | 0.54 |
| $A\beta_{1-28}$ (SEQ ID NO: 3) | 0.96 (0.30) | 1.04 (0.34) | 0.08 (0.56) | 0.55 |
| $A\beta_{17-42}$ (SEQ ID NO: 67) | 0.96 (0.34) | 1.04 (0.29) | 0.08 (0.49) | 0.47 |
| $A\beta_{1-42}$ (SEQ ID NO: 1) | 0.97 (0.38) | 1.08 (0.49) | 0.10 (0.53) | 0.40 |
| p1412* | 0.87 (0.22) | 0.99 (0.33) | 0.11 (0.34) | 0.18 |
| PHA | 28.73 (14.24) | 27.75 (32.85) | −0.98 (26.57) | 0.87 |

*p1412 is a non-relevant control peptide.
Statistical analyses: The differences in lymphocyte proliferations between week 0 and week 16 were examined by the paired t-test. The differences between the change of mean cytokine concentrations (week 16 vs. week 0) in response to Aβ peptides and controls were examined by paired Wilcoxon signed-rank test. Statistical significance levels were determined by 2-tailed tests ($p < 0.05$). R (version 2.13.0) was used for all statistical analyses.

TABLE 20

Mean Cytokine Concentrations (SD) (pg/mL)[1] Produced by Peripheral Blood Mononuclear Cells (PBMCs) from Patient Subjects Collected at Week 0 and Week 16 upon Coculture with Various Aβ peptides

| Peptide (SEQ ID NO:) | Th1 IL-2 | | Th1 IFN-γ | | Th2 IL-6 | | Th2 IL-10 | | Both TNF-α | |
|---|---|---|---|---|---|---|---|---|---|---|
| | Week 0 | Week 16 | Week 0 | Week 16 | Week 0 | Week 16 | Week 0 | Week 16 | Week 0 | Week 16 |
| $A\beta_{1-14}$ (4) | 31.06 (32.48) | 31.20 (24.29) | 13.52 (16.88) | 16.07 (12.88) | 31.34 (29.67) | 50.74 (51.97) | 5.67 (1.56) | 5.62 (1.58) | 36.82 (62.84) | 39.84 (51.69) |
| $A\beta_{1-16}$ (66) | 31.42 (31.38) | 35.98 (23.93) | 14.95 (16.14) | 13.76 (14.19) | 52.50 (31.68) | 50.35 (42.63) | 5.70 (1.63) | 5.81 (1.78) | 47.42 (72.17) | 47.25 (69.73) |
| $A\beta_{1-28}$ (3) | 36.73 (34.29) | 40.55 (27.99) | 15.99 (23.57) | 20.68 (24.39) | 31.74 (25.38) | 42.27 (41.84) | 5.61 (1.52) | 6.17 (2.46) | 41.59 (66.53) | 51.20 (67.78) |
| $A\beta_{17-42}$ (67) | 24.59 (−25.68) | 29.15 (21.17) | 9.67 (9.74) | 13.58 (15.63) | >44.55 (70.86)[3] | 46.90 (51.30) | 5.34 (0.86) | 5.56 (1.54) | 15.60 (18.44) | 24.78 (39.26) |
| $A\beta_{1-42}$ (1) | 23.06 (17.65) | 27.34 (16.86) | 13.42 (16.12) | >44.84 (77.34) | >141.25 (130.11)[4] | >202.02 (121.32)[5] | 11.13 (22.68) | 31.90 (50.21) | >31.63 (71.46)[3] | >88.78[6] (132.91) |
| p1412 | 30.88 (27.42) | 39.96 (25.97) | 14.40 (18.39) | 21.72 (29.89) | 31.81 (52.12) | 60.69 (95.80) | 5.25 (0.64) | 5.18 (0.53) | 17.14 (23.50) | 20.85 (29.26) |
| PHA | 10.38[7] (11.34) | 12.84[7] (6.49) | >320.00 (0.00)[2] | >318.91 (4.77)[2] | >320.00 (0.00)[2] | >320.00 (0.00)[2] | 173.83 (84.75) | >162.77 (99.70) | >313.01 (30.48)[2] | >300.87 (46.51)[2] |
| Cell control | 33.36 (24.91) | 38.83 (33.08) | 13.81 (12.29) | 17.84 (18.24) | 45.86 (41.93) | 65.31 (76.54) | 5.88 (2.45) | 5.73 (1.59) | 44.32 (70.90) | 46.72 (67.76) |

[1] Quantifiable range of the assay is between 5 and 320 pg/mL.
[2] Concentrations of 90% or more subjects were above upper quantification limit (AQL), i.e., 320 pg/mL.
[3] One patient had an AQL value.
[4] Six patients had AQL values.
[5] Eight patients had AQL values.
[6] Four patients had AQL values.
[7] The lack of IL-2 production observed in response to PHA mitogen is consistent with findings reported by Katial et. Al, et al 1998 under similar experimental conditions.

The invention claimed is:

1. A composition comprising a combination of Aβ peptide immunogen constructs consisting of the amino acid sequences of SEQ ID NOs:62 and 63.

2. The composition of claim 1, further comprising a CpG oligodeoxynucleotide (ODN).

3. The composition of claim 2, further comprising an adjuvant.

4. A pharmaceutical composition comprising:
   a) the combination of Aβ peptide immunogen constructs of claim 1;
   b) a CpG oligodeoxynucleotide (ODN); and
   c) a pharmaceutically acceptable delivery vehicle and/or adjuvant.

5. The pharmaceutical composition of claim 4, wherein the combination of Aβ peptide immunogen constructs are present in an equal molar ratio and wherein the Aβ peptide immunogen constructs and the CpG oligodeoxynucleotide (ODN) are in the form of a stabilized immunostimulatory complex.

6. The pharmaceutical composition of claim 5, wherein the pharmaceutically acceptable delivery vehicle and/or agent is aluminum phosphate (AlPO$_4$).

7. A pharmaceutical composition consisting essentially of:
   a) the combination of Aβ peptide immunogen constructs of claim 1;
   b) a CpG oligodeoxynucleotide (ODN); and
   c) a pharmaceutically acceptable delivery vehicle and/or adjuvant.

8. A pharmaceutical composition consisting essentially of:
   a) the combination of Aβ peptide immunogen constructs of claim 1 in an equal molar ratio;
   b) a CpG oligodeoxynucleotide (ODN); and
   c) a pharmaceutically acceptable delivery vehicle and/or adjuvant,
   wherein the Aβ peptide immunogen constructs in (a) and the CpG oligodeoxynucleotide (ODN) in (b) are in the form of a stabilized immunostimulatory complex and wherein the pharmaceutically acceptable delivery vehicle and/or agent in (c) is aluminum phosphate (AlPO$_4$).

9. A method for producing antibodies that recognize the N-terminus of β-amyloid (Aβ) in a host comprising:
   administering to the host the pharmaceutical composition of claim 4.

10. A method for treating a patient with Alzheimer's Disease (AD) comprising:
  administering to the patient the pharmaceutical composition of claim 4.

11. A composition comprising a combination of Aβ peptide immunogen constructs consisting of the amino acid sequences of SEQ ID NOs:64 and 65.

12. The composition of claim 11, further comprising a CpG oligodeoxynucleotide (ODN).

13. The composition of claim 12, further comprising an adjuvant.

14. A pharmaceutical composition comprising:
  a) the combination of Aβ peptide immunogen constructs of claim 11;
  b) a CpG oligodeoxynucleotide (ODN); and
  c) a pharmaceutically acceptable delivery vehicle and/or adjuvant.

15. The pharmaceutical composition of claim 14, wherein the combination of Aβ peptide immunogen constructs are present in an equal molar ratio and wherein the Aβ peptide immunogen constructs and the CpG oligodeoxynucleotide (ODN) are in the form of a stabilized immunostimulatory complex.

16. The pharmaceutical composition of claim 15, wherein the pharmaceutically acceptable delivery vehicle and/or agent is aluminum phosphate (AlPO$_4$).

17. A pharmaceutical composition consisting essentially of:
  a) the combination of Aβ peptide immunogen constructs of claim 11;
  b) a CpG oligodeoxynucleotide (ODN); and
  c) a pharmaceutically acceptable delivery vehicle and/or adjuvant.

18. A pharmaceutical composition consisting essentially of:
  a) the combination of Aβ peptide immunogen constructs of claim 11 in an equal molar ratio;
  b) a CpG oligodeoxynucleotide (ODN); and
  c) a pharmaceutically acceptable delivery vehicle and/or adjuvant, wherein the Aβ peptide immunogen constructs in (a) and the CpG oligodeoxynucleotide (ODN) in (b) are in the form of a stabilized immunostimulatory complex and
  wherein the pharmaceutically acceptable delivery vehicle and/or agent in (c) is aluminum phosphate (AlPO$_4$).

19. A method for producing antibodies that recognize the N-terminus of β-amyloid (Aβ) in a host comprising:
  administering to the host the pharmaceutical composition of claim 14.

20. A method for treating a patient with dementia of the Alzheimer's type comprising:
  administering to the patient the pharmaceutical composition of claim 14.

* * * * *